US011453701B2

(12) United States Patent
Tanaka et al.

(10) Patent No.: US 11,453,701 B2
(45) Date of Patent: Sep. 27, 2022

(54) TAU AGGREGATION PEPTIDE INHIBITORS

(71) Applicant: ADRX, INC., Thousand Oaks, CA (US)

(72) Inventors: Shiho Tanaka, Redondo Beach, CA (US); Ashley Wright, Los Angeles, CA (US); James Treanor, Lake Sherwood, CA (US); Marcin Apostol, Malibu, CA (US); Matthew A. G. Graf, Ventura, CA (US)

(73) Assignee: ADRX, INC., Thousand Oaks, CA (US)

( * ) Notice: Subject to any disclaimer, the term of this patent is extended or adjusted under 35 U.S.C. 154(b) by 20 days.

(21) Appl. No.: 16/637,567

(22) PCT Filed: Aug. 20, 2018

(86) PCT No.: PCT/US2018/047108
§ 371 (c)(1),
(2) Date: Feb. 7, 2020

(87) PCT Pub. No.: WO2019/036725
PCT Pub. Date: Feb. 21, 2019

(65) Prior Publication Data
US 2020/0216495 A1    Jul. 9, 2020

Related U.S. Application Data

(60) Provisional application No. 62/547,586, filed on Aug. 18, 2017.

(51) Int. Cl.
*C07K 7/06* (2006.01)
*G01N 33/68* (2006.01)
*A61K 38/00* (2006.01)

(52) U.S. Cl.
CPC ........... *C07K 7/06* (2013.01); *G01N 33/6896* (2013.01); *A61K 38/00* (2013.01); *G01N 2500/02* (2013.01)

(58) Field of Classification Search
None
See application file for complete search history.

(56) References Cited

U.S. PATENT DOCUMENTS

| 2004/0034191 | A1 | 2/2004 | Manoharan et al. |
| 2015/0099259 | A1 | 4/2015 | Franco |
| 2015/0299259 | A1* | 10/2015 | Funke ............... C07K 7/08 424/1.69 |

FOREIGN PATENT DOCUMENTS

| WO | WO 2014108475 | * | 7/2014 |
| WO | WO-2014/182961 A9 | | 6/2015 |

OTHER PUBLICATIONS

Reitz "Toward precision medicine in Alzheimer's disease" Ann Transl Med 2016;4(6):107 (Year: 2016).*
Stanford "Alzheimer's Prevention, Treatment and Research—A Q&A with Dr. Frank Longo Jan. 29, 2016" accessed from stanfordhealthcare.org on May 3, 2016 (Year: 2016).*
Webster "isolated" accessed from merriam-webster.com on Sep. 17, 2021 (Year: 2021).*
Neu "The Dipeptide Arg-Gln Inhibits Retinal Neovascularization in the Mouse Model of Oxygen-Induced Retinopathy" Investigative Ophthalmology & Visual Science, Jul. 2006, vol. 47, No. 7 (Year: 2006).*
Jaseja "Conformational studies of antimetastatic laminin-1 derived peptides in different solvent systems, using solution NMR spectroscopy" J. Peptide Res., 2003, 61, 24-39. (Year: 2003).*
Mohamed "Tau-Derived-Hexapeptide 306VQIVYK311 Aggregation Inhibitors: Nitrocatechol Moiety as A Pharmacophore in Drug Design" ACS Chem. Neurosci. 2013, 4, 1559-1570 (Year: 2013).*
Esteras-Chopo et al., New Strategy for the Germination of Specific d-Peptide Amyloid Inhibitors, J. Molec. Biol., 377(5):1372-1381 (2008).
Sievers et al., Structure-based design of non-natural amino-acid inhibitors of amyloid fibril formation, Nature, 475(7354):96-110 (2011).
International Search Report and Written Opinion of the International Search Authority, PCT/US2018/047108, dated Feb. 20, 2019.
International Preliminary Report on Patentability, PCT/US2018/047108, dated Feb. 18, 2020.

* cited by examiner

*Primary Examiner* — Adam Weidner
(74) *Attorney, Agent, or Firm* — Marshall, Gerstein & Borun LLP

(57) ABSTRACT

This invention relates to the field of tau aggregation inhibitors. More specifically, the invention relates to amyloid therapeutics. More specifically, the invention provides pharmaceutical compositions and methods of treating aggregation associated conditions or diseases with certain peptides.

30 Claims, 1 Drawing Sheet

Specification includes a Sequence Listing.

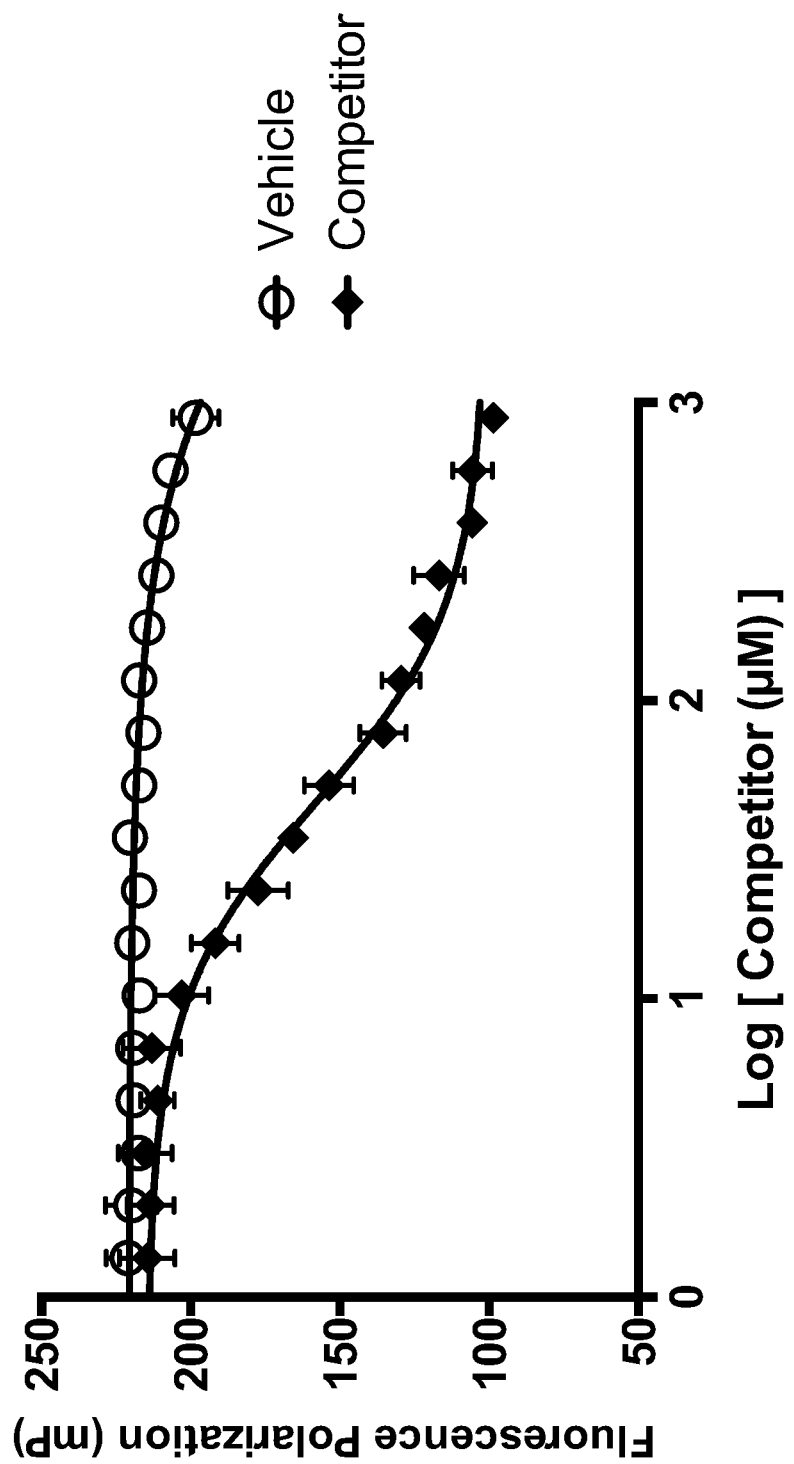

TAU AGGREGATION PEPTIDE INHIBITORS

CROSS-REFERENCE TO RELATED APPLICATIONS

This application is the U.S. national stage of International Application No. PCT/US2018/047108, which claims priority benefit under 35 USC § 119 of U.S. Provisional Application No. 62/547,586, filed on Aug. 18, 2017.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: Filename: 52336A_Seqlisting.txt; Size: 23,024 bytes; Created: Aug. 20, 2018.

FIELD OF THE INVENTION

This invention relates to the field of tau aggregation inhibitors. More specifically, the invention relates to anti-amyloid therapeutics. More specifically, the invention provides pharmaceutical compositions and methods of treating aggregation associated conditions or diseases with certain peptides.

BACKGROUND

Amyloid diseases are associated with the transformation of normally soluble proteins into amyloid fibrils, which are elongated, unbranched protein aggregates. In Alzheimer's disease patients, two distinct types of fibrillar aggregates are commonly found in brain samples: amyloid plaques comprising deposits of amyloid beta protein (API) and neurofibrillary tangles consisting of the microtubule-associated protein tau. The association of tau with several diseases including Alzheimer's disease and senile dementia makes it an important target for disrupting fibrillation. There remains a need in the art for improved inhibitors of fibril formation.

SUMMARY

The present invention provides peptides that exhibit activity in inhibiting aggregation of the tau protein and uptake of aggregation-inducing tau amyloid. This application relates, e.g., to peptides which bind to tau or tau fibrils.

The present invention provides peptides that efficiently bind to the zipper region of tau protein. The present invention thus provides peptides and their use in treating aggregation-related conditions.

The present invention provides peptides that efficiently bind to the VQIINK (SEQ ID NO: 1; PEPTIDE ID NO: 192) region of tau protein.

The present invention provides peptides that efficiently bind to the VQIVYK (SEQ ID NO: 2; PEPTIDE ID NO: 191) region of tau protein.

The present invention is based on the identification of highly potent peptides that bind tau protein. The present invention thus provides, in an aspect, a recombinant or synthetic peptide comprising or consisting of the amino-acid sequence set forth in any one of PEPTIDE ID NOs: 1-176, 184-190, and 193-475. The invention also provides peptides that are analogs and variants of such sequences, as described below in greater detail.

One aspect of the invention is an aggregation inhibitory peptide comprising or consisting of an amino acid sequence represented by Formula I-XVIII, as defined below in greater detail. The invention also provides peptides that are analogs and variants of such sequences, as described below in greater detail. Inhibitory peptides of the invention, including the active variants, are sometimes referred to herein as "inhibitory peptides of the invention."

In one aspect, the peptides of the present invention can be used to identify agents that reduce or increase a level of tau aggregates in a cell. Methods of identifying such agents can be useful for identifying new therapies for tau aggregate-related diseases. In one aspect, a method includes: contacting aggregate fibrils with a peptide inhibitor of tau aggregation (the "probe") to form a pre-formed fibril-probe complex, contacting said fibril-probe complex with a test compound; and detecting or measuring a level of probe displacement.

The present disclosure moreover includes pharmaceutical compositions comprising peptides that comprise or consist of amino acid sequences PEPTIDE ID NOs 1-176, 184-190, and 193-475, analogs and derivatives thereof described herein, and a pharmaceutically acceptable excipient, as well as a method of treating or preventing a disease or medical condition (e.g., Alzheimer's Disease) in a patient. The method comprises administering to the patient a presently disclosed peptide or peptide variant, optionally formulated into a pharmaceutical composition, in an amount effective to treat the disease or medical condition. Relatedly, the invention includes use of peptides of the invention for treating or preventing the disease or medical condition; and use of the peptide in the manufacture of a medicament for treating or preventing the disease or medical condition. Other aspects of the invention will be apparent from the detailed description, drawing, and claims that follow.

BRIEF DESCRIPTION OF THE DRAWINGS

FIG. 1. Shows the results of the competition assay utilizing the binding of Tau40 with a peptide probe. In this case a peptide was conjugated with TAMRA fluorescent label on its N-terminus and incubated with Tau40 amyloid. The addition of the same unlabeled peptide "competitor" at concentrations given in the x-axis, shows how it competes for binding with the probe. As it competes the probe loses the fluoresence polarization signal it has when it is bound to the Tau amyloid.

DETAILED DESCRIPTION

In one aspect the disclosure provides peptides that therapeutically affect tau protein aggregation, more specifically Alzheimer's disease.

In one embodiment, the disclosure comprises a peptide of any of the amino acid sequences set forth in any one of PEPTIDE ID NO: 1-176, 184-190, and 193-475.

An embodiment comprises a peptide comprising or consisting of an amino acid sequence of the amino acid sequence of formula I (I)
(PEPTIDE ID NO: 1)
Xaa1-Xaa2-Xaa3-Xaa4-Xaa5-Xaa6-Xaa7-Xaa8

Wherein Xaa1 is absent, D-Phe, D-Arg, D-Leu, D-Tyr, D-Pro or D-Trp; Xaa2 is D-Arg, D-His, D-Thr, D-Gln, D-Glu, D-Ala, D-Ile, D-Asp, D-Leu, D-Phe, D-Pro, D-Trp, or D-Lys; Xaa3 is D-Leu, D-Val, D-Ile, D-Phe, D-Lys, D-Arg or D-Trp; Xaa4 is D-Phe, D-Leu, D-Glu, D-Gln, D-Gly, D-Val, D-Asp, D-Asn, D-Pro, D-His, D-Trp, D-Ile, D-Arg, or D-Lys; Xaa5 is D-His, D-Ile, D-Val, D-Ala, D-Gly, D-Phe, D-Gln, D-Arg, D-Lys, D-Leu or D-Trp; Xaa6 is D-His, D-Lys, D-Trp, D-Gln, D-Asn, D-Glu, D-Leu, D-Ala, D-Val or D-Arg; Xaa7 is D-Arg, D-His, D-Leu, D-Lys, D-Glu, D-Val, D-Gly, D-Tyr, D-Phe, D-Thr or D-Trp; and Xaa8 is absent, D-Arg, D-Trp, D-Leu, D-Ile, D-Val, D-His, D-Phe, or D-Tyr; provided the peptide is not llrllr or rlqlrw; or C-terminal acids or amides, or N-acetyl derivatives thereof; or pharmaceutically acceptable salts thereof.

An embodiment comprises a peptide of Formula I wherein Xaa1 is D-Phe, D-Arg, D-Leu, D-Tyr, D-Pro or D-Trp; Xaa2 is D-Arg, D-His, D-Thr, D-Gln, D-Glu, D-Asp, D-Leu, D-Phe, D-Ala, D-Ile, D-Pro, D-Trp, or D-Lys; Xaa3 is D-Leu, D-Val, D-Ile, D-Phe, D-Lys, D-Arg or D-Trp; Xaa4 is D-Phe, D-Leu, D-Glu, D-Gln, D-Gly, D-Val, D-Asp, D-Asn, D-Pro, D-His, D-Trp, D-Ile, D-Arg, or D-Lys; Xaa5 is D-His, D-Ile, D-Val, D-Ala, D-Gly, D-Phe, D-Gln, D-Arg, D-Lys, D-Leu or D-Trp; Xaa6 is D-His, D-Lys, D-Trp, D-Gln, D-Asn, D-Glu, D-Leu, D-Ala, D-Val or D-Arg; Xaa7 is D-Arg, D-His, D-Leu, D-Phe, D-Lys, D-Glu, D-Val, D-Gly, D-Tyr, D-Thr or D-Trp; and Xaa8 is D-Arg, D-Trp, D-Leu, D-Ile, D-Val, D-His, D-Phe, or D-Tyr; or C-terminal acids and amides, and N-acetyl derivatives thereof; or pharmaceutically acceptable salts thereof.

An embodiment comprises a peptide of Formula I wherein Xaa1 is D-Phe, D-Arg, D-Pro or D-Trp; Xaa2 is D-Arg, D-His, D-Thr, D-Gln, D-Glu, D-Leu, D-Ala, D-Ile, D-Pro, D-Trp, or D-Lys; Xaa3 is D-Leu, D-Val, D-Ile, D-Lys, D-Arg or D-Trp; Xaa4 is D-Phe, D-Leu, D-Glu, D-Gln, D-Gly, D-Trp, D-Ile, D-Arg, or D-Lys; Xaa5 is D-His, D-Ile, D-Val, D-Ala, D-Arg, D-Lys, D-Leu or D-Trp; Xaa6 is D-His, D-Lys, D-Trp, D-Glu, D-Leu, D-Ala, D-Val or D-Arg; Xaa7 is D-Arg, D-His, D-Leu, D-Phe, D-Thr or D-Trp; and Xaa8 is absent; or C-terminal acids and amides, and N-acetyl derivatives thereof; or pharmaceutically acceptable salts thereof.

An embodiment comprises a peptide of Formula I wherein Xaa1 is absent; Xaa2 is D-Arg, D-His, D-Thr, D-Gln, D-Glu, D-Ala, D-Ile, D-Pro, D-Trp, or D-Lys; Xaa3 is D-Leu, D-Val, D-Ile, D-Lys, D-Arg or D-Trp; Xaa4 is D-Phe, D-Leu, D-Glu, D-Gln, D-Gly, D-Trp, D-Ile, D-Arg, or D-Lys; Xaa5 is D-His, D-Ile, D-Val, D-Ala, D-Arg, D-Lys, D-Leu or D-Trp; Xaa6 is D-His, D-Lys, D-Trp, D-Glu, D-Leu, D-Ala, D-Val or D-Arg; Xaa7 is D-Arg, D-His, D-Leu, D-Phe, D-Thr or D-Trp; and Xaa8 is absent; or C-terminal acids and amides, and N-acetyl derivatives thereof; or pharmaceutically acceptable salts thereof.

In some embodiments a peptide according to the invention comprises or consists of any D-amino acid sequence listed in Table 1.

TABLE 1

| Sequence | PEPTIDE ID NO: |
|---|---|
| wkvqvrlw | (PEPTIDE ID NO: 2), |
| wrlkvrww | (PEPTIDE ID NO: 3), |
| frlkvrwf | (PEPTIDE ID NO: 4), |
| lelkikfw | (PEPTIDE ID NO: 5), |
| fklklwwf | (PEPTIDE ID NO: 6), |
| fwlrihwf | (PEPTIDE ID NO: 7), |
| wrfhihfy | (PEPTIDE ID NO: 8), |
| fklwlrwf | (PEPTIDE ID NO: 9), |
| frlwihwf | (PEPTIDE ID NO: 10), |
| wrlwihww | (PEPTIDE ID NO: 11), |
| wklwlrww | (PEPTIDE ID NO: 12), |
| wklklrww | (PEPTIDE ID NO: 13), |
| wklklwww | (PEPTIDE ID NO: 14), |
| fwlklrwf | (PEPTIDE ID NO: 15), |
| wrlriwww | (PEPTIDE ID NO: 16), |
| rwrwrw | (PEPTIDE ID NO: 17), |
| frlriwwf | (PEPTIDE ID NO: 18), |
| whlrirw | (PEPTIDE ID NO: 19), |
| wrlrihww | (PEPTIDE ID NO: 20), |
| wikirw | (PEPTIDE ID NO: 21), |
| rtlkivwr | (PEPTIDE ID NO: 22), |
| rlkirw | (PEPTIDE ID NO: 23), |
| riklrw | (PEPTIDE ID NO: 24), |
| wikirr | (PEPTIDE ID NO: 25), |
| rikirw | (PEPTIDE ID NO: 26), |
| rlrirw | (PEPTIDE ID NO: 27), |
| kiklkw | (PEPTIDE ID NO: 28), |
| wikiwr | (PEPTIDE ID NO: 29), |
| wwlrihww | (PEPTIDE ID NO: 30), |
| wikivr | (PEPTIDE ID NO: 31), |
| rtlkivw | (PEPTIDE ID NO: 32), |
| prirlhw | (PEPTIDE ID NO: 33), |
| klkikw | (PEPTIDE ID NO: 34), |
| fkiklkw | (PEPTIDE ID NO: 35), |
| rlrihw | (PEPTIDE ID NO: 36), |
| frlkirw | (PEPTIDE ID NO: 37), |
| rirlrw | (PEPTIDE ID NO: 38), |
| klklrw | (PEPTIDE ID NO: 39), |
| wrlrww | (PEPTIDE ID NO: 40), |
| rirlhw | (PEPTIDE ID NO: 41), |
| wrlrvw | (PEPTIDE ID NO: 42), |
| wwrfhwr | (PEPTIDE ID NO: 43), |
| rlwvrw | (PEPTIDE ID NO: 44), |
| tlkirw | (PEPTIDE ID NO: 45), |

TABLE 1-continued

| Sequence | PEPTIDE ID NO: |
|---|---|
| wlkvrw | (PEPTIDE ID NO: 46), |
| friklrw | (PEPTIDE ID NO: 47), |
| fklklww | (PEPTIDE ID NO: 48), |
| rlrivw | (PEPTIDE ID NO: 49), |
| rirwrw | (PEPTIDE ID NO: 50), |
| fklwlrw | (PEPTIDE ID NO: 51), |
| klkivw | (PEPTIDE ID NO: 52), |
| ilkivw | (PEPTIDE ID NO: 53), |
| tikivw | (PEPTIDE ID NO: 54), |
| rplkivw | (PEPTIDE ID NO: 55), |
| frirlrw | (PEPTIDE ID NO: 56), |
| fklklrwf | (PEPTIDE ID NO: 57), |
| frlrihwf | (PEPTIDE ID NO: 58), |
| plkivw | (PEPTIDE ID NO: 59), |
| fkikikw | (PEPTIDE ID NO: 60), |
| frikirw | (PEPTIDE ID NO: 61), |
| wviklt | (PEPTIDE ID NO: 62), |
| plrivw | (PEPTIDE ID NO: 63), |
| tlkihw | (PEPTIDE ID NO: 64), |
| rielhw | (PEPTIDE ID NO: 65), |
| kikikw | (PEPTIDE ID NO: 66), |
| tlkivr | (PEPTIDE ID NO: 67), |
| qlrihw | (PEPTIDE ID NO: 68), |
| irlywh | (PEPTIDE ID NO: 69), |
| frlrirw | (PEPTIDE ID NO: 70), |
| rialhw | (PEPTIDE ID NO: 71), |
| wlkirw | (PEPTIDE ID NO: 72), |
| twrlvl | (PEPTIDE ID NO: 73), |
| eirlhw | (PEPTIDE ID NO: 74), |
| ririrw | (PEPTIDE ID NO: 75), |
| tlkiaw | (PEPTIDE ID NO: 76), |
| tlkiww | (PEPTIDE ID NO: 77), |
| tlkivw | (PEPTIDE ID NO: 78), |
| wklvvw | (PEPTIDE ID NO: 79), |
| klklkw | (PEPTIDE ID NO: 80), |
| wwlklrww | (PEPTIDE ID NO: 81), |
| airlhw | (PEPTIDE ID NO: 82), |
| wlkivw | (PEPTIDE ID NO: 83), |
| tlklvw | (PEPTIDE ID NO: 84), |
| wiklrw | (PEPTIDE ID NO: 85), |
| elkivw | (PEPTIDE ID NO: 86), |
| tlkiew | (PEPTIDE ID NO: 87), |
| tlkivf | (PEPTIDE ID NO: 88), |
| wkvqvrw | (PEPTIDE ID NO: 89), |
| wklklrw | (PEPTIDE ID NO: 90), |
| wklwlrw | (PEPTIDE ID NO: 91), |
| wkvwvryw | (PEPTIDE ID NO: 92), |
| wkvwvrgw | (PEPTIDE ID NO: 93), |
| wkvkfqhw | (PEPTIDE ID NO: 94), |
| wkvnvrlw | (PEPTIDE ID NO: 95), |
| wkvwgkvw | (PEPTIDE ID NO: 96), |
| wkvpvryw | (PEPTIDE ID NO: 97), |
| wkvwgrvw | (PEPTIDE ID NO: 98), |
| wkvhiqhw | (PEPTIDE ID NO: 99), |
| wkvkiqyh | (PEPTIDE ID NO: 100), |
| wrlrihw | (PEPTIDE ID NO: 101), |
| wrvqvrw | (PEPTIDE ID NO: 102), |
| wrlriww | (PEPTIDE ID NO: 103), |
| wrirlryw | (PEPTIDE ID NO: 104), |
| wriwiryw | (PEPTIDE ID NO: 105), |
| wrvhfehw | (PEPTIDE ID NO: 106), |
| whvrirhv | (PEPTIDE ID NO: 107), |
| whvrinhl | (PEPTIDE ID NO: 108), |
| whlrlrhw | (PEPTIDE ID NO: 109), |
| wfkiklel | (PEPTIDE ID NO: 110), |
| wlrvqvkw | (PEPTIDE ID NO: 111), |
| wdlrlqyw | (PEPTIDE ID NO: 112), |
| fririhhf | (PEPTIDE ID NO: 113), |
| fririkhy | (PEPTIDE ID NO: 114), |
| fririhhw | (PEPTIDE ID NO: 115), |
| frlklrhw | (PEPTIDE ID NO: 116), |
| frlkirhw | (PEPTIDE ID NO: 117), |
| frvrirhw | (PEPTIDE ID NO: 118), |
| frvkiehw | (PEPTIDE ID NO: 119), |
| frvkiqhw | (PEPTIDE ID NO: 120), |
| friklkwh | (PEPTIDE ID NO: 121), |
| fkirihhy | (PEPTIDE ID NO: 122), |
| fklrlrhw | (PEPTIDE ID NO: 123), |

TABLE 1-continued

| Sequence | PEPTIDE ID NO: |
|---|---|
| fkihlrhw | (PEPTIDE ID NO: 124), |
| fklklrhw | (PEPTIDE ID NO: 125), |
| fklhlrhw | (PEPTIDE ID NO: 126), |
| fkihikhy | (PEPTIDE ID NO: 127), |
| fklhirhw | (PEPTIDE ID NO: 128), |
| fkielhwh | (PEPTIDE ID NO: 129), |
| fkirikwh | (PEPTIDE ID NO: 130), |
| fklhlkhy | (PEPTIDE ID NO: 131), |
| fklkikw | (PEPTIDE ID NO: 132), |
| felrlhwh | (PEPTIDE ID NO: 133), |
| felhikwh | (PEPTIDE ID NO: 134), |
| felklrwh | (PEPTIDE ID NO: 135), |
| felrikhy | (PEPTIDE ID NO: 136), |
| feleiewh | (PEPTIDE ID NO: 137), |
| fhirirhw | (PEPTIDE ID NO: 138), |
| fhirlewh | (PEPTIDE ID NO: 139), |
| fhlkirhh | (PEPTIDE ID NO: 140), |
| fhirlrhh | (PEPTIDE ID NO: 141), |
| lqfdlqyf | (PEPTIDE ID NO: 142), |
| lkirlhhw | (PEPTIDE ID NO: 143), |
| lkiklrhy | (PEPTIDE ID NO: 144), |
| lririkhy | (PEPTIDE ID NO: 145), |
| lrirlhhf | (PEPTIDE ID NO: 146), |
| lkirihyh | (PEPTIDE ID NO: 147), |
| lkihirhw | (PEPTIDE ID NO: 148), |
| lrlhlrhw | (PEPTIDE ID NO: 149), |
| lrlrikhf | (PEPTIDE ID NO: 150), |
| lhiklrwh | (PEPTIDE ID NO: 151), |
| lririrfh | (PEPTIDE ID NO: 152), |
| lhirlrhw | (PEPTIDE ID NO: 153), |
| lklkikhf | (PEPTIDE ID NO: 154), |
| lkiriehy | (PEPTIDE ID NO: 155), |
| lhiklkhf | (PEPTIDE ID NO: 156), |
| leikirhw | (PEPTIDE ID NO: 157), |
| lrieiewh | (PEPTIDE ID NO: 158), |
| yrvriewl | (PEPTIDE ID NO: 159), |
| yhvkfrhw | (PEPTIDE ID NO: 160), |
| yrvriqhi | (PEPTIDE ID NO: 161), |
| yrirlehv | (PEPTIDE ID NO: 162), |

TABLE 1-continued

| Sequence | PEPTIDE ID NO: |
|---|---|
| yririnhl | (PEPTIDE ID NO: 163), |
| rlrihww | (PEPTIDE ID NO: 164), |
| rlkvrw | (PEPTIDE ID NO: 165), |
| rlrvrw | (PEPTIDE ID NO: 166), and |
| tiklvw | (PEPTIDE ID NO: 167). |

In some embodiments a peptide according to the invention comprises or consists of any D-amino acid sequence listed in Table 2.

TABLE 2

| Sequence | PEPTIDE ID NO |
|---|---|
| lkirihyl | (PEPTIDE ID NO: 193), |
| lkiriryh | (PEPTIDE ID NO: 194), |
| wwrvklrw | (PEPTIDE ID NO: 195), |
| vrwwklrw | (PEPTIDE ID NO: 196), |
| wrlkvrwl | (PEPTIDE ID NO: 197), |
| wlkirihy | (PEPTIDE ID NO: 198), |
| lkvrwwwr | (PEPTIDE ID NO: 199), |
| wrldrw | (PEPTIDE ID NO: 200), |
| kvrwwlrw | (PEPTIDE ID NO: 201), |
| lwrlkvrw | (PEPTIDE ID NO: 202), |
| ukirihy | (PEPTIDE ID NO: 203), |
| vrwwwrlk | (PEPTIDE ID NO: 204), |
| twrlkvrw | (PEPTIDE ID NO: 205), |
| lkiriwyh | (PEPTIDE ID NO: 206), |
| kwrlkvrw | (PEPTIDE ID NO: 207), |
| lkirilyh | (PEPTIDE ID NO: 208), |
| gwrlkvrw | (PEPTIDE ID NO: 209), |
| lrlkvrwl | (PEPTIDE ID NO: 210), |
| lkirfhy | (PEPTIDE ID NO: 211), |
| lkiwikyh | (PEPTIDE ID NO: 212), |
| hrlkvrwh | (PEPTIDE ID NO: 213), |
| lkirifyh | (PEPTIDE ID NO: 214), |
| wrfkfrw | (PEPTIDE ID NO: 215) |
| lkfrihy | (PEPTIDE ID NO: 216) |
| rwrlkvrw | (PEPTIDE ID NO: 217), |
| wrlkvrwf | (PEPTIDE ID NO: 218), |
| lkirimy | (PEPTIDE ID NO: 219), |
| wrrkvrww | (PEPTIDE ID NO: 220), |
| lrlkvrww | (PEPTIDE ID NO: 221), |

TABLE 2-continued

| Sequence | PEPTIDE ID NO |
|---|---|
| wrlkvrwh | (PEPTIDE ID NO: 222), |
| lkilihyh | (PEPTIDE ID NO: 223), |
| rlkvrwww | (PEPTIDE ID NO: 224), |
| rrlkvrww | (PEPTIDE ID NO: 225), |
| wrfkvrw | (PEPTIDE ID NO: 226), |
| rkirihyh | (PEPTIDE ID NO: 227), |
| lkirbhy | (PEPTIDE ID NO: 228), |
| ewrlkvrw | (PEPTIDE ID NO: 229), |
| wrlkvrwr | (PEPTIDE ID NO: 230), |
| frlkvrww | (PEPTIDE ID NO: 231), |
| fkirihyf | (PEPTIDE ID NO: 232), |
| lkikihy | (PEPTIDE ID NO: 233), |
| wwrlkvrw | (PEPTIDE ID NO: 234), |
| tlkirihy | (PEPTIDE ID NO: 235), |
| glkirihy | (PEPTIDE ID NO: 236), |
| lkiwiyyh | (PEPTIDE ID NO: 237), |
| wrlrvrww | (PEPTIDE ID NO: 238), |
| lririhyh | (PEPTIDE ID NO: 239), |
| lkirihlh | (PEPTIDE ID NO: 240), |
| wrlkerww | (PEPTIDE ID NO: 241), |
| mrlrihw | (PEPTIDE ID NO: 242), |
| klkirihy | (PEPTIDE ID NO: 243), |
| lkirizy | (PEPTIDE ID NO: 244), |
| lkirihy | (PEPTIDE ID NO: 245), |
| wrmrihw | (PEPTIDE ID NO: 246), |
| flkirihy | (PEPTIDE ID NO: 247), |
| wrlkvaw | (PEPTIDE ID NO: 248), |
| bkirihy | (PEPTIDE ID NO: 249), |
| lkirihyf | (PEPTIDE ID NO: 250), |
| lkiriuy | (PEPTIDE ID NO: 251), |
| lkbrihy | (PEPTIDE ID NO: 252), |
| elkirihy | (PEPTIDE ID NO: 253), |
| mrlkvrw | (PEPTIDE ID NO: 254), |
| wrlktrw | (PEPTIDE ID NO: 255), |
| ylkirihy | (PEPTIDE ID NO: 256), |
| walkvrw | (PEPTIDE ID NO: 257), |
| wrukvrw | (PEPTIDE ID NO: 258), |
| hlkirihy | (PEPTIDE ID NO: 259), |
| wrlrmhw | (PEPTIDE ID NO: 260), |
| fwrlkvrw | (PEPTIDE ID NO: 261), |
| wrlriht | (PEPTIDE ID NO: 262), |
| wrlkfrw | (PEPTIDE ID NO: 263), |
| welkvrww | (PEPTIDE ID NO: 264), |
| hrlkvrww | (PEPTIDE ID NO: 265), |
| hwrlkvrw | (PEPTIDE ID NO: 266), |
| lkiruhy | (PEPTIDE ID NO: 267), |
| ywrlkvrw | (PEPTIDE ID NO: 268), |
| lkirihya | (PEPTIDE ID NO: 269), |
| frlrihw | (PEPTIDE ID NO: 270), |
| lkiriay | (PEPTIDE ID NO: 271), |
| wrlriaw | (PEPTIDE ID NO: 272), |
| wqlkvrw | (PEPTIDE ID NO: 273), |
| lkirihrh | (PEPTIDE ID NO: 274), |
| wrlkvrwe | (PEPTIDE ID NO: 275), |
| wrtkvrw | (PEPTIDE ID NO: 276), |
| lkiriyy | (PEPTIDE ID NO: 277), |
| wrlkvrrw | (PEPTIDE ID NO: 278), |
| lkurihy | (PEPTIDE ID NO: 279), |
| wrlqvrw | (PEPTIDE ID NO: 280), |
| wrlkvqw | (PEPTIDE ID NO: 281), |
| urlkvrw | (PEPTIDE ID NO: 282), |
| tkirihy | (PEPTIDE ID NO: 283), |
| wrlkvrew | (PEPTIDE ID NO: 284), |
| lkiqihy | (PEPTIDE ID NO: 285), |
| wrbkvrw | (PEPTIDE ID NO: 286), |
| lkuruhy | (PEPTIDE ID NO: 287), |
| wrlevrww | (PEPTIDE ID NO: 288), |
| wrlkvrw | (PEPTIDE ID NO: 289), |
| rrlrihw | (PEPTIDE ID NO: 290), |
| lkirihyr | (PEPTIDE ID NO: 291), |
| wrlhvrww | (PEPTIDE ID NO: 292), |
| brlkvrw | (PEPTIDE ID NO: 293), |
| wnlkvrw | (PEPTIDE ID NO: 294), |
| lkihihyh | (PEPTIDE ID NO: 295), |
| wrlkvnw | (PEPTIDE ID NO: 296), |
| lkirixy | (PEPTIDE ID NO: 297), |
| rlkvrww | (PEPTIDE ID NO: 298), |
| lkiwihyh | (PEPTIDE ID NO: 299), |

TABLE 2-continued

| Sequence | PEPTIDE ID NO |
|---|---|
| hyhirikl | (PEPTIDE ID NO: 300), |
| wrlavrw | (PEPTIDE ID NO: 301), |
| lkifiyyh | (PEPTIDE ID NO: 302), |
| lkiriayh | (PEPTIDE ID NO: 303), |
| wmlrihw | (PEPTIDE ID NO: 304), |
| wtlrihw | (PEPTIDE ID NO: 305), |
| wrinvrw | (PEPTIDE ID NO: 306), |
| wrlkbrw | (PEPTIDE ID NO: 307), |
| wrlkurw | (PEPTIDE ID NO: 308), |
| lairihyh | (PEPTIDE ID NO: 309), |
| wrlwvrww | (PEPTIDE ID NO: 310), |
| rirwywk | (PEPTIDE ID NO: 311), |
| arlrihw | (PEPTIDE ID NO: 312), |
| wrlkveww | (PEPTIDE ID NO: 313), |
| wrlritw | (PEPTIDE ID NO: 314), |
| wrlevrw | (PEPTIDE ID NO: 315), |
| leirihy | (PEPTIDE ID NO: 316), |
| lkimihy | (PEPTIDE ID NO: 317), |
| lkiriheh | (PEPTIDE ID NO: 318), |
| wqlkvqw | (PEPTIDE ID NO: 319), |
| lkizihy | (PEPTIDE ID NO: 320), |
| lkiuihy | (PEPTIDE ID NO: 321), |
| welrihw | (PEPTIDE ID NO: 322), |
| wrlkvra | (PEPTIDE ID NO: 323), |
| lkiriey | (PEPTIDE ID NO: 324), |
| wrlaihw | (PEPTIDE ID NO: 325), |
| hwrwrwr | (PEPTIDE ID NO: 326), |
| trlrihw | (PEPTIDE ID NO: 327), |
| wrlkvdw | (PEPTIDE ID NO: 328), |
| fkifihyh | (PEPTIDE ID NO: 329), |
| wrltihw | (PEPTIDE ID NO: 330), |
| wdlkvrw | (PEPTIDE ID NO: 331), |
| wrlrifw | (PEPTIDE ID NO: 332), |
| lkixihy | (PEPTIDE ID NO: 333), |
| lkiriha | (PEPTIDE ID NO: 334), |
| lkiyihy | (PEPTIDE ID NO: 335), |
| lkiaihy | (PEPTIDE ID NO: 336), |
| wririrw | (PEPTIDE ID NO: 337), |
| erlkvrw | (PEPTIDE ID NO: 338), |
| wrldvrw | (PEPTIDE ID NO: 339), |
| lkiwiwyh | (PEPTIDE ID NO: 340), |
| lkirrhyh | (PEPTIDE ID NO: 341), |
| arlkvrw | (PEPTIDE ID NO: 342), |
| wrakvrw | (PEPTIDE ID NO: 343), |
| wrlkarw | (PEPTIDE ID NO: 344), |
| walrihw | (PEPTIDE ID NO: 345), |
| wrlrahw | (PEPTIDE ID NO: 346), |
| wrlriha | (PEPTIDE ID NO: 347), |
| wrleihw | (PEPTIDE ID NO: 348), |
| wrlriew | (PEPTIDE ID NO: 349), |
| wrlmihw | (PEPTIDE ID NO: 350), |
| wrtrihw | (PEPTIDE ID NO: 351), |
| wrlnvnw | (PEPTIDE ID NO: 352), |
| lkirihye | (PEPTIDE ID NO: 353), |
| lkieihy | (PEPTIDE ID NO: 354), |
| wrarihw | (PEPTIDE ID NO: 355), |
| wrlrthw | (PEPTIDE ID NO: 356), |
| wnlnvrw | (PEPTIDE ID NO: 357), |
| lkifiwyh | (PEPTIDE ID NO: 358), |
| erlkvrww | (PEPTIDE ID NO: 359), |
| akirihyh | (PEPTIDE ID NO: 360), |
| kwrwyrr | (PEPTIDE ID NO: 361), |
| rihyhikl | (PEPTIDE ID NO: 362), |
| lkieihyh | (PEPTIDE ID NO: 363), |
| kvrwwwrl | (PEPTIDE ID NO: 364), |
| hkirihyh | (PEPTIDE ID NO: 365), |
| lairihy | (PEPTIDE ID NO: 366), |
| leirihyh | (PEPTIDE ID NO: 367), |
| klkwlw | (PEPTIDE ID NO: 368), |
| lkifihyh | (PEPTIDE ID NO: 369), |
| kirihyhl | (PEPTIDE ID NO: 370), |
| yrlkvrw | (PEPTIDE ID NO: 371), |
| wnlkvnw | (PEPTIDE ID NO: 372), |
| kirihyh | (PEPTIDE ID NO: 373), |
| lkirih | (PEPTIDE ID NO: 374), |
| ihyhrikl | (PEPTIDE ID NO: 375), |
| wrhkvrw | (PEPTIDE ID NO: 376), |
| ekirihy | (PEPTIDE ID NO: 377), |

TABLE 2-continued

| Sequence | PEPTIDE ID NO |
|---|---|
| wrlkhrw | (PEPTIDE ID NO: 378), |
| lkirihah | (PEPTIDE ID NO: 379), |
| wrllvrww | (PEPTIDE ID NO: 380), |
| lkvrww | (PEPTIDE ID NO: 381), |
| wqlqvrw | (PEPTIDE ID NO: 382), |
| rihyhlki | (PEPTIDE ID NO: 383), |
| wrlkvew | (PEPTIDE ID NO: 384), |
| wrukurw | (PEPTIDE ID NO: 385), |
| irihyhlk | (PEPTIDE ID NO: 386), |
| ekirihyh | (PEPTIDE ID NO: 387), |
| welkvrw | (PEPTIDE ID NO: 388), |
| lkirieyh | (PEPTIDE ID NO: 389), |
| awakvrw | (PEPTIDE ID NO: 390), |
| wflrihw | (PEPTIDE ID NO: 391), |
| wrtktrw | (PEPTIDE ID NO: 392), |
| wrbkbrw | (PEPTIDE ID NO: 393), |
| ihyhlkir | (PEPTIDE ID NO: 394), |
| erlrihw | (PEPTIDE ID NO: 395), |
| wrlrihe | (PEPTIDE ID NO: 396), |
| welkvew | (PEPTIDE ID NO: 397), |
| lkarihyh | (PEPTIDE ID NO: 398), |
| arlkarw | (PEPTIDE ID NO: 399), |
| lktrihy | (PEPTIDE ID NO: 400), |
| ararihw | (PEPTIDE ID NO: 401), |
| wrakarw | (PEPTIDE ID NO: 402), |
| wdldvrw | (PEPTIDE ID NO: 403), |
| wrlkv | (PEPTIDE ID NO: 404), |
| lkrrihyh | (PEPTIDE ID NO: 405), |
| wrlkvr | (PEPTIDE ID NO: 406), |
| wrhkhrw | (PEPTIDE ID NO: 407), |
| wrekvrww | (PEPTIDE ID NO: 408), |
| lkiaihyh | (PEPTIDE ID NO: 409), |
| lhlkiryh | (PEPTIDE ID NO: 410), |
| fkleiryh | (PEPTIDE ID NO: 411), |
| feirlwhh | (PEPTIDE ID NO: 412), |
| fklklrw | (PEPTIDE ID NO: 413), |
| lkirirfh | (PEPTIDE ID NO: 414), |
| lklrirhh | (PEPTIDE ID NO: 415), |
| wlrvqvklw | (PEPTIDE ID NO: 416), |
| frlwihw | (PEPTIDE ID NO: 417), |
| fkieieyh | (PEPTIDE ID NO: 418), |
| vkvwgrlw | (PEPTIDE ID NO: 419), |
| lrirlhyh | (PEPTIDE ID NO: 420), |
| lrikirfh | (PEPTIDE ID NO: 421), |
| ldlrfkly | (PEPTIDE ID NO: 422), |
| frlriww | (PEPTIDE ID NO: 423), |
| whvkfelf | (PEPTIDE ID NO: 424), |
| wwlrihw | (PEPTIDE ID NO: 425), |
| frlklrfh | (PEPTIDE ID NO: 426), |
| fhleirhw | (PEPTIDE ID NO: 427), |
| wrlwihw | (PEPTIDE ID NO: 428), |
| lkleirwh | (PEPTIDE ID NO: 429), |
| feirlhhw | (PEPTIDE ID NO: 430), |
| fhieirhf | (PEPTIDE ID NO: 431), |
| rlkwrw | (PEPTIDE ID NO: 432), |
| wwlklrw | (PEPTIDE ID NO: 433), |
| lklhlhfh | (PEPTIDE ID NO: 434), |
| wevqvew | (PEPTIDE ID NO: 435), |
| rlkvww | (PEPTIDE ID NO: 436), |
| fhihikfh | (PEPTIDE ID NO: 437), |
| klklrwf | (PEPTIDE ID NO: 438), |
| rrlkvrwr | (PEPTIDE ID NO: 439), |
| yhlklhyw | (PEPTIDE ID NO: 440), |
| lrvqvrl | (PEPTIDE ID NO: 441), |
| feirihyh | (PEPTIDE ID NO: 442), |
| fhlhlkhw | (PEPTIDE ID NO: 443), |
| rwkvrw | (PEPTIDE ID NO: 444), |
| hrfkvqly | (PEPTIDE ID NO: 445), |
| rlrihwf | (PEPTIDE ID NO: 446), |
| lefelkyw | (PEPTIDE ID NO: 447), |
| klklrww | (PEPTIDE ID NO: 448), |
| wkvqvryw | (PEPTIDE ID NO: 449), |
| rlrlkw | (PEPTIDE ID NO: 450), |
| rlkirihy | (PEPTIDE ID NO: 451), |
| wrlrimw | (PEPTIDE ID NO: 452), and |
| wrlrihm | (PEPTIDE ID NO: 453). |

In one embodiment, the invention comprises or consists of a peptide selected from wrlrihw, (PEPTIDE ID NO: 101)

wklwlrw, (PEPTIDE ID NO: 91)

fririhhf, (PEPTIDE ID NO: 113)

wkvwvryw, (PEPTIDE ID NO: 92)

fkirihhy, (PEPTIDE ID NO: 122)

lelkikfw, (PEPTIDE ID NO: 5)

elkivw, (PEPTIDE ID NO: 86)

tlkivw, (PEPTIDE ID NO: 78)

wkvqvrlw, (PEPTIDE ID NO: 2)
and wrlkvrww, (PEPTIDE ID NO: 3)

and a pharmaceutically acceptable salt thereof.

In one embodiment, the invention comprises or consists of a peptide selected from wrlrihw, (PEPTIDE ID NO: 101)

rlkirihy, (PEPTIDE ID NO: 451)

wrlrimw, (PEPTIDE ID NO: 452)

wrlrihm, (PEPTIDE ID NO: 453)

lkirihyl, (PEPTIDE ID NO: 193)

lkiriryh, (PEPTIDE ID NO: 194)

wwrvklrw, (PEPTIDE ID NO: 195)

lkirihyh, (PEPTIDE ID NO: 147)

vrwwklrw, (PEPTIDE ID NO: 196)

wrlkvrwl, (PEPTIDE ID NO: 197)

wlkirihy, (PEPTIDE ID NO: 198)

wkvwvryw, (PEPTIDE ID NO: 92)

lkvrwwwr, (PEPTIDE ID NO: 199)

wrlrlrw, (PEPTIDE ID NO: 200)

ririrw, (PEPTIDE ID NO: 75)

wikirw, (PEPTIDE ID NO: 21)

kvrwwlrw, (PEPTIDE ID NO: 201)

lwrlkvrw, (PEPTIDE ID NO: 202)

ukirihy, (PEPTIDE ID NO: 203)

vrwwwrlk, (PEPTIDE ID NO: 204)
and wrlkvrww, (PEPTIDE ID NO: 3)

and a pharmaceutically acceptable salt thereof.

An embodiment comprises a peptide comprising or consisting of an amino acid sequence of the amino acid sequence of formula II (II)
(PEPTIDE ID NO: 168)
Xaa9-Xaa10-Xaa11-Xaa12-Xaa13-Xaa14-Xaa15-Xaa16

Wherein Xaa9 is absent, D-Phe, D-Leu, D-Tyr, or D-Trp; Xaa10 is D-Arg, D-His, D-Asp, D-Thr, D-Gln, D-Glu, D-Leu, D-Pro, D-Phe, D-Trp, or D-Lys; Xaa11 is D-Leu, D-Val, D-Ile, D-Phe, D-Lys, or D-Arg; Xaa12 is D-Leu, D-Val, D-Glu, D-Gln, D-Asp, D-Asn, D-Pro, D-His, D-Trp, D-Ile, D-Arg, or D-Lys; Xaa13 is D-Ile, D-Val, D-Gly, D-Phe, D-Arg, D-Lys, D-Gln, or D-Leu; Xaa14 is D-His, D-Lys, D-Trp, D-Glu, D-Gln, D-Asn, D-Leu, D-Val or D-Arg; Xaa15 is D-Lys, D-His, D-Glu, D-Leu, D-Val, D-Gly, D-Phe, D-Tyr, or D-Trp; and Xaa16 is absent, D-Trp, D-Leu, D-Ile, D-Val, D-His, D-Phe, or D-Tyr; provided the peptide is not llrllr or rlqlrw; or C-terminal acids or amides, or N-acetyl derivatives thereof; or pharmaceutically acceptable salts thereof.

An embodiment comprises a peptide of Formula II wherein Xaa9 is D-Phe, D-Leu, D-Tyr, or D-Trp; Xaa10 is D-Arg, D-His, D-Asp, D-Gln, D-Glu, D-Leu, D-Phe, D-Trp, or D-Lys; Xaa11 is D-Leu, D-Val, D-Ile, D-Phe, D-Lys, or D-Arg; Xaa12 is D-Val, D-Glu, D-Gln, D-Asp, D-Asn, D-Pro, D-His, D-Trp, D-Ile, D-Arg, or D-Lys; Xaa13 is D-Ile, D-Val, D-Gly, D-Phe, D-Lys, D-Gln, or D-Leu; Xaa14 is D-His, D-Lys, D-Trp, D-Glu, D-Gln, D-Asn, D-Leu, D-Val or D-Arg; Xaa15 is D-Lys, D-His, D-Glu, D-Leu, D-Val, D-Gly, D-Phe, D-Tyr, or D-Trp; and Xaa16 is D-Trp, D-Leu, D-Ile, D-Val, D-His, D-Phe, or D-Tyr; or C-terminal acids and amides, and N-acetyl derivatives thereof; or pharmaceutically acceptable salts thereof.

An embodiment comprises a peptide of Formula II wherein Xaa9 is D-Phe, D-Arg, D-Pro or D-Trp; Xaa10 is D-Arg, D-His, D-Leu, or D-Lys; Xaa11 is D-Leu, D-Val, D-Ile, or D-Arg; Xaa12 is, D-Gln, D-Trp, D-Ile, D-Arg, or D-Lys; Xaa13 is D-His, D-Ile, D-Val, or D-Leu; Xaa14 is D-His, D-Lys, D-Trp, or D-Arg; Xaa15 is D-Trp; and Xaa16 is absent; or C-terminal acids and amides, and N-acetyl derivatives thereof; or pharmaceutically acceptable salts thereof.

An embodiment comprises a peptide of Formula II wherein Xaa9 is absent; Xaa10 is D-Arg, D-Thr, D-Glu, D-Trp, or D-Lys; Xaa11 is D-Leu, D-Ile, or D-Arg; Xaa12 is D-Leu, D-Arg, or D-Lys; Xaa13 is D-Ile, D-Val, D-Arg, or D-Leu; Xaa14 is D-Lys, D-Val or D-Arg; Xaa15 is D-Trp; and Xaa16 is absent; or C-terminal acids and amides, and N-acetyl derivatives thereof; or pharmaceutically acceptable salts thereof.

An embodiment comprises a peptide comprising or consisting of an amino acid sequence of formula III (III)
(PEPTIDE ID NO: 169)
D-Trp-D-Lys-Xaa17-Xaa18-Xaa19-Xaa20-Xaa21-Xaa22 wherein Xaa17 is a D-amino acid having a non-polar side chain; Xaa18 is a D-amino acid having a polar side chain or a non-polar side chain; Xaa19 is a D-amino acid having a non-polar side chain; Xaa20 is a D-amino acid having a polar side chain; Xaa21 is a D-amino acid having a polar side chain or a non-polar side chain; and Xaa22 is absent, or is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula III wherein Xaa17 is D-Val or D-Leu; Xaa18 is selected from D-Gln, D-His, D-Lys, D-Asn, D-Pro and D-Trp; Xaa19 is selected from D-Phe, D-Gly, D-Ile, D-Val and D-Leu; Xaa20 is selected from D-Gln, D-Arg, D-Lys, and D-Trp; Xaa21 is D-Tyr, D-Leu, D-Val, D-Gly, D-His, and D-Trp; and Xaa22 is absent, or is D-His or D-Trp; or C-terminal acids or amides, or N-acetyl derivatives thereof; or pharmaceutically acceptable salts thereof.

An embodiment comprises a peptide of the amino acid sequence of formula III selected from wklwlrw (PEPTIDE ID NO: 91); wkvwvryw (PEPTIDE ID NO: 92); wkvqvrlw (PEPTIDE ID NO: 2); wkvwvrgw (PEPTIDE ID NO: 93); wkvkiqyh (PEPTIDE ID NO: 100); wkvkfqhw (PEPTIDE ID NO: 94); wkvnvrlw (PEPTIDE ID NO: 95); and wkvqvrw (PEPTIDE ID NO: 89); or C-terminal acids or amides, or N-acetyl derivatives thereof; or pharmaceutically acceptable salts thereof.

An embodiment comprises a peptide comprising or consisting of an amino acid sequence of formula IV (IV)
(PEPTIDE ID NO: 170)
D-Trp-D-Arg-Xaa23-Xaa24-Xaa25-Xaa26-Xaa27-Xaa28 wherein Xaa23 is a D-amino acid having a non-polar side chain; Xaa24 is a D-amino acid having a polar side chain or a non-polar side chain; Xaa25 is aD-amino acid having a non-polar side chain; Xaa26 is a D-amino acid having a polar side chain or a non-polar side chain; Xaa27 is a D-amino acid having a polar side chain or a non-polar side chain; and Xaa28 is absent, or is a D-amino acid having a polar side chain or a non-polar side chain; or C-terminal acids or amides, or N-acetyl derivatives thereof, or pharmaceutically acceptable salts thereof.

An embodiment comprises a peptide of the amino acid sequence of formula IV wherein Xaa23 is selected from D-Phe, D-Ile, D-Val and D-Leu; Xaa24 is selected from D-Gln, D-His, D-Lys, D-Arg, and D-Trp; Xaa25 is selected from D-Phe, D-Ile, D-Val and D-Leu; Xaa26 is selected from D-Glu, D-His, D-Arg and D-Trp; Xaa27 is D-Phe, D-Tyr, D-His and D-Trp; and Xaa28 is absent, or is D-Tyr or D-Trp; or C-terminal acids or amides, or N-acetyl derivatives thereof, or pharmaceutically acceptable salts thereof.

An embodiment comprises a peptide of the amino acid sequence of formula IV selected from wrlrihw (PEPTIDE ID NO: 101); wrlrihww (PEPTIDE ID NO: 20); wrvqvrw (PEPTIDE ID NO: 102); and wrlriww (PEPTIDE ID NO: 103); or C-terminal acids or amides, or N-acetyl derivatives thereof, or pharmaceutically acceptable salts thereof.

An embodiment comprises a peptide comprising or consisting of an amino acid sequence of formula V (V)
(PEPTIDE ID NO: 171)
D-Trp-D-His-Xaa29-Xaa30-Xaa31-Xaa32-Xaa33-Xaa34 wherein Xaa29 is a D-amino acid having a non-polar side chain; Xaa30 is a D-amino acid having a polar side chain; Xaa31 is a D-amino acid having a non-polar side chain; Xaa32 is a D-amino acid having a polar side chain; Xaa33 is a D-amino acid having a polar side chain or a non-polar side chain; and Xaa34 is absent, or is a D-amino acid having a non-polar side chain; or C-terminal acids or amides, or N-acetyl derivatives thereof, or pharmaceutically acceptable salts thereof.

An embodiment comprises a peptide of the amino acid sequence of formula V wherein Xaa29 is D-Val or D-Leu; Xaa30 is D-Arg; Xaa31 is D-Ile or D-Leu; Xaa32 is D-Asn or D-Arg; Xaa33 is D-His or D-Trp; and Xaa34 is absent or is selected from D-Trp, D-Val and D-Leu; or C-terminal acids or amides, or N-acetyl derivatives thereof; or pharmaceutically acceptable salts thereof.

An embodiment comprises a peptide of the amino acid sequence of formula V selected from whlrlrhw (PEPTIDE ID NO: 109) and whlrirw (PEPTIDE ID NO: 19); or C-terminal acids or amides, or N-acetyl derivatives thereof; or pharmaceutically acceptable salts thereof.

An embodiment comprises a peptide comprising or consisting of amino acid sequence of formula VI (VI)
(PEPTIDE ID NO: 172)
D-Phe-D-Arg-Xaa35-Xaa36-Xaa37-Xaa38-Xaa39-Xaa40 wherein Xaa35 is a D-amino acid having a non-polar side chain; Xaa36 is a D-amino acid having a polar side chain or a non-polar side chain; Xaa37 is a D-amino acid having a non-polar side chain; Xaa38 is a D-amino acid having a polar side chain or a non-polar side chain; Xaa39 is a D-amino acid having a polar side chain or a non-polar side chain; and Xaa40 is absent, or is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula VI wherein Xaa35 is selected from D-Ile, D-Val and D-Leu; Xaa36 is selected from D-Trp, D-Lys and D-Arg; Xaa37 is selected from D-Val, D-Ile and D-Leu; Xaa38 is selected from D-Trp, D-Glu, D-Gln, D-His, D-Lys or D-Arg; Xaa39 is D-His or D-Trp; and Xaa40 is absent or is selected from D-Trp, D-Tyr and D-Phe; or C-terminal acids or amides, or N-acetyl derivatives thereof; or pharmaceutically acceptable salts thereof.

An embodiment comprises a peptide of the amino acid sequence of formula VI selected from fririhhf (PEPTIDE ID NO: 113), fririkhy (PEPTIDE ID NO: 114), frlkirhw (PEPTIDE ID NO: 117), fririhhw (PEPTIDE ID NO: 115), frlklrhw (PEPTIDE ID NO: 116), frvrirhw (PEPTIDE ID NO: 118), friklrw (PEPTIDE ID NO: 47), and frlkvrwf (PEPTIDE ID NO: 4); or C-terminal acids or amides, or N-acetyl derivatives thereof; or pharmaceutically acceptable salts thereof.

An embodiment comprises a peptide comprising or consisting of amino acid sequence of formula VII (VII)
(PEPTIDE ID NO: 173)
D-Phe-D-Lys-Xaa41-Xaa42-Xaa43-Xaa44-Xaa45-Xaa46 wherein Xaa41 is a D-amino acid having a non-polar side chain; Xaa42 is a D-amino acid having a polar side chain or a non-polar side chain; Xaa43 is a D-amino acid having a non-polar side chain; Xaa44 is a D-amino acid having a polar side chain or a non-polar side chain; Xaa45 is a D-amino acid having a polar side chain or a non-polar side chain; and Xaa46 is absent, or is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula VII wherein Xaa41 is D-Ile, or D-Leu; Xaa42 is selected from D-His, D-Trp, D-Glu, D-Lys and D-Arg; Xaa43 is D-Ile or D-Leu; Xaa44 is selected from D-Trp, D-His, D-Lys or D-Arg; Xaa45 is D-His or D-Trp; and Xaa46 is absent or is selected from D-Trp, D-His, D-Tyr and D-Phe; or C-terminal acids or amides, or N-acetyl derivatives thereof; or pharmaceutically acceptable salts thereof.

An embodiment comprises a peptide of the amino acid sequence of formula VII selected from flcirihhy (PEPTIDE ID NO: 122), fldrlrhw (PEPTIDE ID NO: 123), fldkikw (PEPTIDE ID NO: 132), fkihlrhw (PEPTIDE ID NO: 124), fldklrhw (PEPTIDE ID NO: 125), fldhlrhw (PEPTIDE ID NO: 126), flkikikw (PEPTIDE ID NO: 60), fkihikhy (PEPTIDE ID NO: 127), fkiklkw (PEPTIDE ID NO: 35), and fldhirhw (PEPTIDE ID NO: 128); or C-terminal acids or amides, or N-acetyl derivatives thereof; or pharmaceutically acceptable salts thereof.

An embodiment comprises a peptide comprising or consisting of an amino acid sequence of formula VIII (VIII)
(PEPTIDE ID NO: 174)
D-Leu-Xaa47-Xaa48-Xaa49-Xaa50-Xaa51-Xaa52-Xaa53 wherein Xaa47 is a D-amino acid having a polar side chain; Xaa48 is a D-amino acid having a non-polar side chain; Xaa49 is a D-amino acid having a polar side chain; Xaa50 is a D-amino acid having a non-polar side chain; Xaa51 is a D-amino acid having a polar side chain; Xaa52 is a D-amino acid having a polar side chain or a non-polar side chain; and Xaa53 is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula VIII wherein Xaa47 is selected from D-Glu, D-His, D-Gln, D-Lys and D-Arg; Xaa48 is selected from D-Phe, D-Ile, and D-Leu; Xaa49 is selected from D-Asp, D-His, D-Glu, D-Lys and D-Arg; Xaa50 is D-Ile or D-Leu; Xaa51 is selected from D-Glu, D-His, D-Gln, D-Lys and D-Arg; Xaa52 is selected from D-Tyr, D-His, D-Phe and D-Trp; and Xaa53 is selected from D-Trp, D-His, D-Tyr and D-Phe; or C-terminal acids or amides, or N-acetyl derivatives thereof; or pharmaceutically acceptable salts thereof.

An embodiment comprises a peptide of the amino acid sequence of formula VIII selected from lqfdlqyf (PEPTIDE ID NO: 142), lkirlhhw (PEPTIDE ID NO: 143), lkiklrhy (PEPTIDE ID NO: 144), lririkhy (PEPTIDE ID NO: 145), lrirlhhf (PEPTIDE ID NO: 146), lkirihyh (PEPTIDE ID NO: 147), lkihirhw (PEPTIDE ID NO: 148), lrlhlrhw (PEPTIDE ID NO: 149), lrlrikhf (PEPTIDE ID NO: 150), lhiklrwh (PEPTIDE ID NO: 151), lririrfh (PEPTIDE ID NO: 152), and lhirlrhw (PEPTIDE ID NO: 153); or C-terminal acids or amides, or N-acetyl derivatives thereof; or pharmaceutically acceptable salts thereof.

An embodiment comprises a peptide comprising or consisting of an amino acid sequence of formula IX (IX)
(PEPTIDE ID NO: 175)
Xaa54-Xaa55-Xaa56-Xaa57-Xaa58-D-Trp wherein Xaa54 is a D-amino acid having a polar side chain or a non-polar side chain; Xaa55 is a D-amino acid having a polar side chain or a non-polar side chain; Xaa56 is a D-amino acid having a polar side chain or a non-polar side chain; Xaa57 is a D-amino acid having a polar side chain or a non-polar side chain; and Xaa58 is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula IX wherein Xaa54 is selected from D-Trp, D-Glu, D-Thr, D-Lys and D-Arg; Xaa55 is selected from D-Arg, D-Ile, and D-Leu; Xaa56 is selected from D-Leu, D-Lys and D-Arg; Xaa57 is selected from D-Arg, D-Val, D-Ile and D-Leu; and Xaa58 is selected from D-Lys, D-Arg, and D-Val; or C-terminal acids or amides, or N-acetyl derivatives thereof; or pharmaceutically acceptable salts thereof.

An embodiment comprises a peptide of the amino acid sequence of formula IX selected from wikirw (PEPTIDE ID NO: 21), ririrw (PEPTIDE ID NO: 75), rikirw (PEPTIDE ID NO: 26), and rlkirw (PEPTIDE ID NO: 23); or C-terminal acids or amides, or N-acetyl derivatives thereof; or pharmaceutically acceptable salts thereof.

An embodiment comprises a peptide comprising or consisting of amino acid sequence of formula X (X)
(PEPTIDE ID NO: 176)
D-Phe-Xaa59-Xaa60-Xaa61-Xaa62-Xaa63-Xaa64-Xaa65 wherein Xaa59 is a D-amino acid having a polar side chain or a non-polar side chain; Xaa60 is a D-amino acid having a non-polar side chain; Xaa61 is a D-amino acid having a polar side chain or a non-polar side chain; Xaa62 is a D-amino acid having a non-polar side chain; Xaa63 is a D-amino acid having a polar side chain; Xaa64 is a D-amino acid having a polar side chain or a non-polar side chain; and Xaa65 is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula X wherein Xaa59 is selected from D-Glu, D-His, and D-Trp; Xaa60 is D-Ile, or D-Leu; Xaa61 is selected from D-His, D-Glu, D-Lys and D-Arg; Xaa62 is D-Ile or D-Leu; Xaa63 is selected from D-Glu, D-His, D-Lys and D-Arg; Xaa64 is D-His, or D-Trp; and Xaa65 is selected from D-Trp, D-His, D-Tyr and D-Phe; or C-terminal acids or amides, or N-acetyl derivatives thereof; or pharmaceutically acceptable salts thereof.

An embodiment comprises a peptide of the amino acid sequence of formula X selected from fhirirhw (PEPTIDE ID NO: 138), and fwlklrwf (PEPTIDE ID NO: 15); or C-terminal acids or amides, or N-acetyl derivatives thereof; or pharmaceutically acceptable salts thereof.

An embodiment comprises a peptide comprising or consisting of an amino acid sequence of the amino acid sequence of formula Ia (Ia)
(PEPTIDE ID NO: 184)
Xaa1-Xaa2-Xaa3-Xaa4-Xaa5-Xaa6-Xaa7-Xaa8 wherein

Xaa1 is absent, D-Lys, D-Thr, D-Gly, D-Glu, D-His, D-Met, D-Ala, D-Ile, D-Phe, D-Arg, D-Leu, D-Tyr, D-Pro or D-Trp;

Xaa2 is absent, D-Met, D-Arg, D-His, D-Thr, D-Gln, D-Glu, D-Ala, D-Ile, D-Asp, D-Leu, D-Phe, D-Pro, D-Trp, or D-Lys;

Xaa3 is absent, D-Nle, D-Cha, D-Thr, D-Ala, D-His, D-Met, D-Leu, D-Val, D-Ile, D-Phe, D-Lys, D-Arg or D-Trp;

Xaa4 is D-Thr, D-Ala, D-Met, D-Tyr, D-Met(O), D-Cit, D-Nle, D-Cha, D-Tyr, D-Phe, D-Leu, D-Glu, D-Gln, D-Gly, D-Val, D-Asp, D-Asn, D-Pro, D-His, D-Trp, D-Ile, D-Arg, or D-Lys;

Xaa5 is D-Nle, D-Cha, D-Met, D-Thr, D-His, D-Ile, D-Val, D-Ala, D-Gly, D-Phe, D-Gln, D-Glu, D-Arg, D-Lys, D-Leu or D-Trp;

Xaa6 is absent, D-Asp, D-Cha, D-Met, D-Thr, D-Phe, D-Nle, D-Tyr, D-Ile, D-His, D-Lys, D-Trp, D-Gln, D-Asn, D-Glu, D-Leu, D-Ala, D-Val or D-Arg;

Xaa7 is absent, D-Ala, D-Arg, D-His, D-Leu, D-Lys, D-Glu, D-Met, D-Val, D-Gly, D-Tyr, D-Phe, D-Thr or D-Trp; and Xaa8 is absent, D-Ala, D-Lys, D-Arg, D-Trp, D-Leu, D-Ile, D-Val, D-His, D-Phe, or D-Tyr; provided the peptide is not llrllr or rlqlrw; further provided Xaa2 is absent only if Xaa1 is absent; further provided Xaa7 is absent only if Xaa8 is absent; further provided Xaa6 is absent only if Xaa8 and Xaa7 are absent;

or C-terminal acids or amides, or N-acetyl derivatives thereof; or pharmaceutically acceptable salts thereof.

An embodiment comprises a peptide comprising or consisting of amino acid sequence of formula XI (XI)
(PEPTIDE ID NO: 185)
D-Trp-D-Arg-D-Leu-D-Arg-Xaa66-Xaa67-Xaa68-Xaa69 wherein Xaa66 is a D-amino acid having a polar side chain or a non-polar side chain; Xaa67 is a D-amino acid having a polar side chain or a non-polar side chain; Xaa68 is absent or is a D-amino acid having a polar side chain or a non-polar side chain; and Xaa69 is absent or is a D-amino acid having a non-polar side chain; provided Xaa68 is absent only if Xa69 is absent; or C-terminal acids or amides, or N-acetyl derivatives thereof; or pharmaceutically acceptable salts thereof.

An embodiment comprises a peptide of the amino acid sequence of formula XI wherein Xaa66 is D-Ile, D-Leu, D-Met, D-Ala, D-Thr or D-Val; Xaa67 is D-His, D-Trp, D-Met, D-Ala, D-Thr, D-Phe, D-Glu, or D-Arg; Xaa68 is absent, D-Trp, D-Met, D-Thr, D-Ala, or D-Glu; and Xaa69 is absent or D-Trp; provided Xaa68 is absent only if Xa69 is absent; or C-terminal acids or amides, or N-acetyl derivatives thereof; or pharmaceutically acceptable salts thereof.

An embodiment comprises a peptide comprising or consisting of amino acid sequence of formula XII (XII)
(PEPTIDE ID NO: 186)
D-Trp-D-Arg-D-Leu-Xaa70-Xaa71-Xaa72-Xaa73-Xaa74 wherein Xaa70 is a D-amino acid having a polar side chain or a non-polar side chain; Xaa71 is a D-amino acid having a polar side chain or a non-polar side chain; Xaa72 is absent or is a D-amino acid having a polar side chain or a non-polar side chain; Xaa73 is absent or is a D-amino acid having a polar side chain or a non-polar side chain; and Xaa74 is absent or is a D-amino acid having a non-polar side chain; provided Xaa73 is absent only if Xa74 is absent; further provided Xaa72 is absent only if Xaa73 and Xaa74 are absent; or C-terminal acids or amides, or N-acetyl derivatives thereof; or pharmaceutically acceptable salts thereof.

An embodiment comprises a peptide of the amino acid sequence of formula XII wherein Xaa70 is D-Trp, D-Lys, D-Gln, D-Glu, D-His, D-Ala, D-Asn, D-Thr, D-Met, D-Asp, or D-Leu; Xaa71 is a D-Ile, D-Glu, D-Val, D-Thr, D-Phe, D-Ile, D-Ala, or D-His, D-Cha or D-Nle; Xaa72 is absent, D-His, D-Arg, D-Ala, D-Gln, D-Asn, D-Glu, or D-Asp; Xaa73 is absent, D-Trp, D-Arg, D-Glu, or D-Ala; and Xaa74 is absent or is D-Trp; or C-terminal acids or amides, or N-acetyl derivatives thereof; or pharmaceutically acceptable salts thereof.

An embodiment comprises a peptide comprising or consisting of amino acid sequence of formula XIII (XIII)
(PEPTIDE ID NO: 187)
D-Leu-D-Lys-D-Ile-Xaa75-Xaa76-Xaa77-Xaa78-Xaa79 wherein Xaa75 is a D-amino acid having a polar side chain or a non-polar side chain; Xaa76 is a D-amino acid having a polar side chain or a non-polar side chain; Xaa77 is absent or is a D-amino acid having a polar side chain or a non-polar side chain; Xaa78 is D-amino acid having a polar side chain; and Xaa79 is absent or is a D-amino acid having a non-polar side chain; or C-terminal acids or amides, or N-acetyl derivatives thereof; or pharmaceutically acceptable salts thereof.

An embodiment comprises a peptide of the amino acid sequence of formula XIII wherein Xaa75 is D-His, D-Arg, D-Trp, D-Lys, D-Leu, D-Phe, D-Glu, D-Ala, D-Gln, D-Met, D-Cit, D-Nle, D-Met(O) or D-Tyr; Xaa76 is D-Ile, D-Leu, D-Arg, D-Cha, D-Nle or D-Phe; Xaa77 is D-Arg, D-Ile, D-Lys, D-Trp, D-Cha, D-Nle, D-His or D-Tyr; Xaa78 is D-His or D-Tyr; and Xaa79 is absent, D-Trp, D-Tyr or D-His; or C-terminal acids or amides, or N-acetyl derivatives thereof; or pharmaceutically acceptable salts thereof.

An embodiment comprises a peptide comprising or consisting of amino acid sequence of formula XIV (XIV)
(PEPTIDE ID NO: 188)
Xaa80-Xaa81-D-Lys-D-Ile-D-Arg-D-Ile-Xaa82-Xaa83-Xaa84-Xaa85 wherein Xaa80 is absent or a D-amino acid having a polar side chain or a non-polar side chain; Xaa81 is absent or a D-amino acid having a polar side chain or a non-polar side chain; Xaa82 is absent or is a D-amino acid having a polar side chain or a non-polar side chain; Xaa83 is absent or is a D-amino acid having a polar side chain or a non-polar side chain; Xaa84 is absent or is a D-amino acid having a polar side chain or a non-polar side chain and Xaa85 is absent or is a D-amino acid having a non-polar side chain; provided Xaa80 is absent if Xaa81 is absent; further provided Xaa85 is absent if Xaa84 is absent; further provided Xaa85 and Xaa84 are both absent if Xaa83 is absent; further provided Xaa85, Xaa84 and Xaa83 are all absent if Xaa82 is absent; or C-terminal acids or amides, or N-acetyl derivatives thereof; or pharmaceutically acceptable salts thereof.

An embodiment comprises a peptide of the amino acid sequence of formula XIV wherein Xaa80 is absent, D-Arg, D-Lys, D-Trp, D-Thr, D-Phe, D-Gln, D-Glu, D-Tyr, or D-His; Xaa81 is absent, D-Leu, D-Nle, D-Cha, D-Thr, D-His, D-Glu, D-Ala, or D-Phe; Xaa82 is absent, D-Nle, D-Ala, D-His, D-Arg, D-Cit, D-Leu, D-Trp, D-Phe, D-Lys, D-Glu, D-Met(O), D-Met or D-Tyr; Xaa83 is absent, D-Ala, D-Glu, D-Arg, D-Leu, D-Trp, D-Tyr or D-His; Xaa84 is absent, D-Glu, D-Arg, D-Ala, D-Phe, D-Leu, D-Trp, D-Tyr or D-His; and Xaa85 is absent, or D-Leu; or C-terminal acids or amides, or N-acetyl derivatives thereof; or pharmaceutically acceptable salts thereof.

An embodiment comprises a peptide comprising or consisting of amino acid sequence of formula XV (XV)
(PEPTIDE ID NO: 189)
Xaa86-Xaa87-Xaa88-Xaa89-D-Lys-D-Val-D-Arg-D-Trp- Xaa90 wherein Xaa86 is absent or a D-amino acid having a polar side chain or a non-polar side chain; Xaa87 is absent or a D-amino acid having a polar side chain or a non-polar side chain; Xaa88 is absent or is a D-amino acid having a polar side chain or a non-polar side chain; Xaa89 is absent or is a D-amino acid having a polar side chain or a non-polar side chain; and Xaa90 is absent or is a D-amino acid having a non-polar side chain; provided Xaa86 is absent if Xaa87 is absent; further provided Xaa86 and Xaa87 are both absent if Xaa88 is absent; further provided Xaa86, Xaa87 and Xaa88 are all absent if Xaa89 is absent; or C-terminal acids or amides, or N-acetyl derivatives thereof; or pharmaceutically acceptable salts thereof.

An embodiment comprises a peptide of the amino acid sequence of formula XV wherein Xaa86 is absent, D-Arg, D-Lys, D-Leu, D-Trp, D-Phe, D-Tyr, D-His, D-Thr, D-Glu, or D-Gly; Xaa87 is absent, D-Tyr, D-Trp, D-Leu, D-His, D-Phe, D-Glu, D-Arg, D-Met, D-Cha, D-Nle or D-Ala; Xaa88 is absent, D-Arg, D-Ala, D-Glu, D-Gln, D-Asn, D-Asp, or D-Trp; Xaa89 is absent, D-Arg, D-Phe, D-Thr, D-Me, D-Cha, D-His, D-Glu, D-Leu or D-Ala; and Xaa90 is absent, D-Arg, D-Glu, D-Leu, D-His, D-Trp, D-Phe, or -D-Trp-D-Leu-D-Arg-D-Trp; or C-terminal acids or amides, or N-acetyl derivatives thereof; or pharmaceutically acceptable salts thereof.

An embodiment comprises a peptide comprising or consisting of amino acid sequence of formula XVI (XVI)
(PEPTIDE ID NO: 190)
Xaa91-Xaa92-Xaa93-Xaa94-Xaa95-D-Trp-D-Trp-D-Trp- Xaa96-Xaa97-Xaa98 wherein Xaa91 is absent or a D-amino acid having a polar side chain or a non-polar side chain; Xaa92 is absent or a D-amino acid having a polar side chain or a non-polar side chain; Xaa93 is absent or is a D-amino acid having a polar side chain or a non-polar side chain; Xaa94 is a D-amino acid having a polar side chain or a non-polar side chain; Xaa95 is absent or is a D-amino acid having a polar side chain or a non-polar side chain; Xaa96 is absent or is a D-amino acid having a polar side chain; Xaa97 is absent or is a D-amino acid having a non-polar side chain; and Xaa98 is absent or is a D-amino acid having a polar side chain; provided Xaa91 is absent if Xaa92 is absent; further provided Xaa98 is absent if Xaa97 is absent; further provided Xaa98 and Xaa97 are both absent if Xaa96 is absent; or C-terminal acids or amides, or N-acetyl derivatives thereof; or pharmaceutically acceptable salts thereof.

An embodiment comprises a peptide of the amino acid sequence of formula XVI wherein Xaa91 is absent, D-Arg, or D-Trp; Xaa92 is absent, D-Lys or D-Leu; Xaa93 is absent D-Leu or D-Lys; Xaa94 D-Val or D-Lys; Xaa95 is D-Arg, or D-Leu; Xaa96 is absent, or D-Arg; Xaa97 is absent, or D-Leu; and Xaa98 is absent, or D-Lys; or C-terminal acids or amides, or N-acetyl derivatives thereof; or pharmaceutically acceptable salts thereof.

An embodiment comprises a peptide comprising or consisting of amino acid sequence of formula XVII (XVII)
(PEPTIDE ID NO: 473)
Xaa99-Xaa100-Xaa101-D-Arg-D-Ile-D-His-D-Trpwherein Xaa99 is a D-amino acid having a polar side chain or a non-polar side chain; Xaa100 is a D-amino acid having a polar side chain or a non-polar side chain; and Xaa101 is a D-amino acid having a polar side chain or a non-polar side chain; or C-terminal acids or amides, or N-acetyl derivatives thereof; or pharmaceutically acceptable salts thereof.

An embodiment comprises a peptide of the amino acid sequence of formula XVII wherein Xaa99 is D-Met, D-Trp, D-Phe, D-Arg, D-Ala, D-Thr or D-Glu; Xaa100 is D-Arg, D-Met, D-Thr, D-Glu, D-Ala or D-Phe; and Xaa101 is D-Leu, D-Met, D-Thr or D-Ala; or C-terminal acids or amides, or N-acetyl derivatives thereof, or pharmaceutically acceptable salts thereof.

An embodiment comprises a peptide comprising or consisting of amino acid sequence of formula XVIII (XVIII)
(PEPTIDE ID NO: 474)
Xaa102-Xaa103-Xaa104-D-Arg-D-Ile-D-His-D-Tyr- Xaa105 wherein Xaa102 is absent or a D-amino acid having a non-polar side chain; Xaa103 is absent or a D-amino acid having a polar side chain or a non-polar side chain; Xaa104 is absent or is a D-amino acid having a polar side chain or a non-polar side chain; and Xaa105 is absent, a D-amino acid having a polar side chain, -D-His-D-Leu-D-Lys, -D-His-D-Leu-D-Lys-D-Ile, or -D-His-D-Ile-D-Lys-D-Leu; provided Xaa102 is absent if Xaa103 is absent; further provided Xaa102 and Xaa103 are both absent if Xaa104 is absent; or C-terminal acids or amides, or N-acetyl derivatives thereof, or pharmaceutically acceptable salts thereof.

An embodiment comprises a peptide of the amino acid sequence of formula XVIII wherein Xaa102 is absent or D-Leu; Xaa103 is absent, D-Lys, D-Arg, D-Ala, or D-Glu; Xaa104 is absent, D-Phe, D-Arg, D-Ala, D-Ile, D-Thr, D-Cha, or D-Nle; and Xaa105 is absent, D-His, -D-His-D-Leu-D-Lys, -D-His-D-Leu-D-Lys-D-Ile, or -D-His-D-Ile-D-Lys-D-Leu; or C-terminal acids or amides, or N-acetyl derivatives thereof, or pharmaceutically acceptable salts thereof.

An embodiment comprises a peptide of the amino acid sequence wrlrihw (PEPTIDE ID NO: 101). In some embodiments a peptide peptide is in a modified form of PEPTIDE ID NO: 101 comprising up to 2 amino acid modifications relative to PEPTIDE ID NO: 101. In some embodiments a peptide is in a modified form of PEPTIDE ID NO: 101 comprising one amino acid modifications relative to PEPTIDE ID NO: 101, the modification(s) being in one of the positions 1, 2, 3, 4, 5, 6, or 7, wherein the amino acid numbering corresponds to PEPTIDE ID NO: 101.

An embodiment comprises a peptide of the amino acid sequence wklwlrw (PEPTIDE ID NO: 91). In some embodiments a peptide peptide is in a modified form of PEPTIDE ID NO: 91 comprising up to 2 amino acid modifications relative to PEPTIDE ID NO: 91. In some embodiments a peptide is in a modified form of PEPTIDE ID NO: 91 comprising one amino acid modifications relative to PEPTIDE ID NO: 91, the modification(s) being in one of the positions 1, 2, 3, 4, 5, 6 or 7, wherein the amino acid numbering corresponds to PEPTIDE ID NO: 91.

An embodiment comprises a peptide of the amino acid sequence elkivw (PEPTIDE ID NO: 86). In some embodiments a peptide peptide is in a modified form of PEPTIDE ID NO: 86 comprising up to 2 amino acid modifications relative to PEPTIDE ID NO: 86. In some embodiments a peptide is in a modified form of PEPTIDE ID NO: 86 comprising one amino acid modifications relative to PEPTIDE ID NO: 86, the modification(s) being in one of the positions 1, 2, 3, 4, 5 or 6, wherein the amino acid numbering corresponds to PEPTIDE ID NO: 86.

An embodiment comprises a peptide of the amino acid sequence fririhhf (PEPTIDE ID NO: 113). In some embodiments a peptide peptide is in a modified form of PEPTIDE ID NO: 113 comprising up to 2 amino acid modifications relative to PEPTIDE ID NO: 113. In some embodiments a peptide is in a modified form of PEPTIDE ID NO: 113 comprising one amino acid modifications relative to PEPTIDE ID NO: 113, the modification(s) being in one of the positions 1, 2, 3, 4, 5, 6, 7 or 8, wherein the amino acid numbering corresponds to PEPTIDE ID NO: 113.

An embodiment comprises a peptide of the amino acid sequence wkvwvryw (PEPTIDE ID NO: 92). In some embodiments a peptide peptide is in a modified form of PEPTIDE ID NO: 92 comprising up to 2 amino acid modifications relative to PEPTIDE ID NO: 92. In some embodiments a peptide is in a modified form of PEPTIDE ID NO: 92 comprising one amino acid modifications relative to PEPTIDE ID NO: 92, the modification(s) being in one of the positions 1, 2, 3, 4, 5, 6, 7 or 8, wherein the amino acid numbering corresponds to PEPTIDE ID NO: 92.

An embodiment comprises a peptide of the amino acid sequence fkirihhy (PEPTIDE ID NO: 122). In some embodiments a peptide peptide is in a modified form of PEPTIDE ID NO: 122 comprising up to 2 amino acid modifications relative to PEPTIDE ID NO: 122. In some embodiments a peptide is in a modified form of PEPTIDE ID NO: 122 comprising one amino acid modifications relative to PEPTIDE ID NO: 122, the modification(s) being in one of the positions 1, 2, 3, 4, 5, 6, 7 or 8, wherein the amino acid numbering corresponds to PEPTIDE ID NO: 122.

An embodiment comprises a peptide of the amino acid sequence tlkivw (PEPTIDE ID NO: 78). In some embodiments a peptide peptide is in a modified form of PEPTIDE ID NO: 78 comprising up to 2 amino acid modifications relative to PEPTIDE ID NO: 78. In some embodiments a peptide is in a modified form of PEPTIDE ID NO: 78 comprising one amino acid modifications relative to PEPTIDE ID NO: 78, the modification(s) being in one of the positions 1, 2, 3, 4, 5 or 6, wherein the amino acid numbering corresponds to PEPTIDE ID NO: 78.

An embodiment comprises a peptide of the amino acid sequence lelkikfw (PEPTIDE ID NO: 5). In some embodiments a peptide peptide is in a modified form of PEPTIDE ID NO: 5 comprising up to 2 amino acid modifications relative to PEPTIDE ID NO: 5. In some embodiments a peptide is in a modified form of PEPTIDE ID NO: 5 comprising one amino acid modifications relative to PEPTIDE ID NO: 5, the modification(s) being in one of the positions 1, 2, 3, 4, 5, 6, 7 or 8, wherein the amino acid numbering corresponds to PEPTIDE ID NO: 5.

An embodiment comprises a peptide of the amino acid sequence wkvqvrlw (PEPTIDE ID NO: 2). In some embodiments a peptide peptide is in a modified form of PEPTIDE ID NO: 2 comprising up to 2 amino acid modifications relative to PEPTIDE ID NO: 2. In some embodiments a peptide is in a modified form of PEPTIDE ID NO: 2 comprising one amino acid modifications relative to PEPTIDE ID NO: 2, the modification(s) being in one of the positions 1, 2, 3, 4, 5, 6, 7 or 8, wherein the amino acid numbering corresponds to PEPTIDE ID NO: 2.

An embodiment comprises a peptide of the amino acid sequence wrlkvrww (PEPTIDE ID NO: 3). In some embodiments a peptide peptide is in a modified form of PEPTIDE ID NO: 3 comprising up to 2 amino acid modifications relative to PEPTIDE ID NO: 3. In some embodiments a peptide is in a modified form of PEPTIDE ID NO: 3 comprising one amino acid modifications relative to PEPTIDE ID NO: 3, the modification(s) being in one of the positions 1, 2, 3, 4, 5, 6, 7 or 8, wherein the amino acid numbering corresponds to PEPTIDE ID NO: 3.

In some embodiments, peptides disclosed herein comprise a sequence having at least 66% sequence identity to any one of amino acid sequences PEPTIDE ID NO: 1-176, 184-190, and 193-475. In certain embodiments, the minimum % identity is selected from, e.g., at least 70%, at least 75%, at least 80%, at least 85%, at least 90%, or at least 95%, or more sequence identity to a given sequence. In certain embodiments, the % identity is in the range of, e.g., about 65% to about 70%, about 70% to about 80%, about 80% to about 85%, about 85% to about 90%, or about 90% to about 95%; %; between about 70% and about 80%, between about 80% and about 90% and between about 90% and about 99% sequence identity.

In certain embodiments, the peptide comprises a sequence having at least 66% sequence identity to any one of amino acid sequences PEPTIDE ID NO: 1-176, 184-190, and 193-475. In certain embodiments, the % identity is selected from, e.g., at least 70%, at least 75%, at least 80%, at least 85%, at least 90%, or at least 95%, or more sequence identity to a given sequence. In certain embodiments, the % identity is in the range of, e.g., about 65% to about 70%, about 70% to about 80%, about 80% to about 85%, about 85% to about 90%, or about 90% to about 95%; %; between about 70% and about 80%, between about 80% and about 90% and between about 90% and about 99% sequence identity, but does not comprise the sequence set forth in PEPTIDE ID NO: 1-176, 184-190, and 193-475.

Peptides of the disclosure include peptides that have been modified in any way and for any reason, for example, to: (1) reduce susceptibility to proteolysis, (2) alter binding affinities, and (3) confer or modify other physicochemical or functional properties. For example, single or multiple amino acid substitutions (e.g., equivalent, conservative or non-conservative substitutions, deletions or additions) may be made in a sequence.

A conservative amino acid substitution refers to the substitution in a peptide of an amino acid with a functionally similar amino acid having similar properties, e.g., size, charge, hydrophobicity, hydrophilicity, and/or aromaticity. The following six groups each contain amino acids that are conservative substitutions for one another are found in Table 3.

TABLE 3

| | |
|---|---|
| i. | Alanine (A), Serine (S), and Threonine (T) |
| ii. | Aspartic acid (D) and Glutamic acid (E) |
| iii. | Asparagine (N) and Glutamine (Q) |
| iv. | Arginine (R) and Lysine (K) |
| v. | Isoleucine (I), Leucine (L), Methionine (M), and Valine (V) |
| vi. | Phenylalanine (F), Tyrosine (Y), and Tryptophan (W) |

Additionally, within the meaning of the term "equivalent amino acid substitution" as applied herein, one amino acid may be substituted for another, in one embodiment, within the groups of amino acids indicated herein below:
1. Amino acids with polar side chains (Asp, Glu, Lys, Arg, His, Asn, Gln, Ser, Thr, Tyr, and Cys)
2. Amino acids with small nonpolar or slightly polar residues (Ala, Ser, Thr, Pro, Gly);
3. Amino acids with non-polar side chains (Gly, Ala, Val, Leu, Ile, Phe, Trp, Pro, and Met)
4. Amino acids with large, aliphatic, nonpolar residues (Met, Leu, Ile, Val, Cys, Norleucine (Nle), homocysteine)
5. Amino acids with aliphatic side chains (Gly, Ala Val, Leu, Ile)
6. Amino acids with cyclic side chains (Phe, Tyr, Trp, His, Pro)
7. Amino acids with aromatic side chains (Phe, Tyr, Trp)
8. Amino acids with acidic side chains (Asp, Glu)
9. Amino acids with basic side chains (Lys, Arg, His)
10. Amino acids with amide side chains (Asn, Gln)
11. Amino acids with hydroxy side chains (Ser, Thr)
12. Amino acids with sulphur-containing side chains (Cys, Met),
13. Neutral, weakly hydrophobic amino acids (Pro, Ala, Gly, Ser, Thr)
14. Hydrophilic, acidic amino acids (Gln, Asn, Glu, Asp), and
15. Hydrophobic amino acids (Leu, Ile, Val).

In some embodiments, the amino acid substitution is not a conservative amino acid substitution, e.g., is a non-conservative amino acid substitution. This class generally includes corresponding D-amino acids, homo-amino acids, N-alkyl amino acids, beta amino acids and other unnatural amino acids. The non-conservative amino acid substitutions still fall within the descriptions identified for the equivalent amino acid substitutions above [e.g. polar, nonpolar, etc.]. Examples of non-conservative amino acids are provided below.

Non limiting examples for alanine non-conservative amino acids are: D-alanine [Dala, (dA), a], N-Acetyl-3-(3, 4-dimethoxyphenyl)-D-alanine, N-Me-D-Ala-OH, N-Me-Ala-OH, H-3-Ala-β-naphthalene, L-(−)-2-Amino-3-ureido-propionic acid, (R)-(+)-α-Allylalanine, (S)-(−)-α-Allylalanine, D-2-Aminobutyric acid, L-2-Aminobutyric acid, DL-2-Aminobutyric acid, 2-Aminoisobutyric acid, α-Aminoisobutyric acid, (S)-(+)-2-Amino-4-phenylbutyric acid ethyl ester, Benzyl α-aminoisobutyrate, Abu-OH, Aib-OH, β-(9-anthryl)-Ala-OH, β-(3-benzothienyl)-Ala-OH, β-(3-benzothienyl)-D-Ala-OH, Cha-OH, Cha-OMe, β-(2-furyl)-Ala-OH, β-(2-furyl)-D-Ala-OH, β-iodo-Ala-OBzl, β-iodo-D-Ala-OBzl, β-iodo-D-Ala-OMe, β-iodo-Ala-OMe, 1-Nal-OH, D-1-Nal-OH, 2-Nal-OH, D-2-Nal-OH, (R)-3-(2-naphthyl)-β-Ala-OH, (S)-3-(2-naphthyl)-β-Ala-OH, 3-phenyl-Phe-OH, 3-(2-pyridyl)-Ala-OH, 3-(3-pyridyl)-Ala-OH, 3-(3-pyridyl)-D-Ala-OH, (S)-3-(3-pyridyl)-β-Ala-OH, 3-(4-pyridyl)-Ala-OH, 3-(4-pyridyl)-D-Ala-OH, β-(2-quinolyl)-Ala-OH, 3-(2-quinolyl)-DL-Ala-OH, 3-(3-quinolyl)-DL-Ala-OH, 3-(2-quinoxalyl)-DL-Ala-OH, β-(4-thiazolyl)-Ala-OH, β-(2-thienyl)-Ala-OH, β-(2-thienyl)-D-Ala-OH, β-(3-thienyl)-Ala-OH, β-(3-thienyl)-D-Ala-OH, 3-Chloro-D-alanine methyl ester, N-[(4-Chlorophenyl)sulfonyl]-β-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N-[(S)-(+)-1-(Ethoxycarbonyl)-3-phenylpropyl]-L-alanine, N-[1-(S)-(+)-Ethoxycarbonyl-3-phenylpropyl]-L-alanyl carboxyanhydride, N-(3-fluorobenzyl)alanine, N-(3-Indolylacetyl)-L-alanine, Methyl (RS)-2-(aminomethyl)-3-phenylpropionate, 3-(2-Oxo-1,2-dihydro-4-quinolinyl) alanine, 3-(1-Pyrazolyl)-L-alanine, 3-(2-Pyridyl)-D-alanine, 3-(2-Pyridyl)-L-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, D-styrylalanine, L-styrylalanine, 3-(2-Thienyl)-L-alanine, 3-(2-Thienyl)-DL-alanine, 3-(2-Thienyl)-DL-alanine, 3,3,3-Trifluoro-DL-alanine, N-Methyl-L-alanine, 3-Ureidopropionic acid, Aib-OH, Cha-OH, Dehydro-Ala-OMe, dehydro-Ala-OH, D-2-Nal-OH, β-Ala-ONp, β-Homoala-OH, β-D-Homoala-OH, β-Alanine, β-Alanine ethyl ester, β-Alanine methyl ester, (S)-diphenyl-β-Homoala-OH, (R)-4-(4-pyridyl)-3-Homoala-OH, (S)-4-(4-pyridyl)-β-Homoala-OH, β-Ala-OH, (S)-diphenyl-β-Homoala-OH, L-β-Homoalanine, (R)-4-(3-pyridyl)-β-Homoala-OH, α-methyl-α-naphthylalanine [Manap], N-methyl-cyclohexylalanine [Nmchexa], cyclohexylalanine [Chexa, Cha], N-methyl-cyclopentylalanine [Nmcpen], cyclopentylalanine [Cpen], N-methyl-α-naphthylalanine [Nmanap], α-naphthylalanine [Anap], L-N-methylalanine [Nmala], D-N-methylalanine [Dnmala], α-methyl-cyclohexylalanine [Mchexa], α-methyl-cyclopentylalanine [Mcpen]. Each possibility represents a separate embodiment.

Non limiting examples for arginine non-conservative amino acids are: homoarginine (hArg), N-methyl arginine (NMeArg), citruline [z, Cit], 2-amino-3-guanidinopropionic acid, N-iminoethyl-L-ornithine, Nω-monomethyl-L-arginine, Nω-nitro-L-arginine, D-arginine, 2-amino-3-ureidopropionic acid, Nω,ω-dimethyl-L-arginine, Nω-Nitro-D-arginine, L-α-methylarginine [Marg], D-α-methylarginine [Dmarg], L-N-methylarginine [Nmarg], D-N-methylarginine [Dnmarg], β-Homoarg-OH, L-Homoarginine, N-(3- guanidinopropyl)glycine [Narg], and D-arginine [Darg, (dR), r]. Each possibility represents a separate embodiment.

Non limiting examples for asparagine non-conservative amino acids are: L-α-methylasparagine [Masn], D-α-methylasparagine [Dmasn], L-N-methylasparagine [Nmasn], D-N-methylasparagine [Dnmasn], N-(carbamylmethyl)glycine [Nasn] and D-asparagine [Dasn, (dN), n]. Each possibility represents a separate embodiment.

Non limiting examples for aspartic acid non-conservative amino acids are: L-α-methylaspartate [Masp], D-α-methylaspartate [Dmasp], L-N-methylaspartic acid [Nmasp], D-N-methylasparatate [Dnmasp], N-(carboxymethyl)glycine [Nasp] and D-aspartic acid [Dasp, (dD), d]. Each possibility represents a separate embodiment.

Non limiting examples for cysteine non-conservative amino acids are: L-Cysteic acid, L-Cysteinesulfinic acid, D-Ethionine, S-(2-Thiazolyl)-L-cysteine, DL-Homocysteine, L-Homocysteine, L-Homocystine, L-α-methylcysteine [Mcys], D-α-methylcysteine [Dmcys], L-N-methylcysteine [Nmcys], D-N-methylcysteine [Dnmcys], N-(thiomethyl) glycine [Ncys] and D-cysteine [Dcys, (dC), c]. Each possibility represents a separate embodiment.

Non limiting examples for glutamic acid non-conservative amino acids are: 7-Carboxy-DL-glutamic acid, 4-Fluoro-DL-glutamic acid, β-Glutamic acid, L-β-Homoglutamic acid, L-α-methylglutamate [Mglu], D-α-methyl glutamic acid [Dmglu], L-N-methylglutamic acid [Nmglu], D-N-methylglutamate [Dnmglu], N-(2-carboxyethyl)glycine [Nglu], and D-glutamic acid [Dglu, (dE), e]. Each possibility represents a separate embodiment.

Non limiting examples for glutamine non-conservative amino acids are: Cit-OH, D-Citrulline, Thio-L-citrulline, 3-Gln-OH, L-β-Homoglutamine, L-α-methylglutamine [Mgln], D-α-methylglutamine [Dmgln], L-N-methylglutamine [Nmgln], D-N-methylglutamine [Dnmgln], N-(2-carbamylethyl)glycine [Ngln], and D-glutamine [Dgln, (dQ), q]. Each possibility represents a separate embodiment.

Non limiting examples for glycine non-conservative amino acids are: tBu-Gly-OH,D-Allylglycine, N-[Bis(methylthio)methylene]glycine methyl ester, Chg-OH, D-Chg-OH, D-cyclopropylglycine, L-cyclopropylglycine, (R)-4-fluorophenylglycine, (S)-4-fluorophenylglycine, iminodiacetic acid, (2-indanyl)-Gly-OH, (±)-α-phosphonoglycine trimethyl ester, D-propargylglycine, propargyl-Gly-OH, (R)-2-thienylglycine, (S)-2-thienylglycine, (R)-3-thienylglycine, (S)-3-thienylglycine, 2-(4-trifluoromethylphenyl)-DL-glycine, (2S,3R,4S)-α-(Carboxycyclopropyl) glycine, N-(Chloroacetyl)glycine ethyl ester, (S)-(+)-2-chlorophenylglycine methyl ester, N-(2-chlorophenyl)-N-(methylsulfonyl)glycine, D-α-Cyclohexylglycine, L-α-Cyclopropylglycine, Di-tert-butyl-iminodicarboxylate, Ethyl acetamidocyanoacetate, N-(2-fluorophenyl)-N-(methylsulfonyl) glycine, N-(4-fluorophenyl)-N-(methylsulfonyl) glycine, N-(2-Furfurylideneacetyl)glycine methyl ester, N-(2-Furoyl)glycine, N-(2-Hydroxyethyl)iminodiacetic acid, N-(4-Hydroxyphenyl)glycine, Iminodiacetic acid, N-Lauroylsarcosine sodium salt, L-α-Neopentylglycine, N-(Phosphonomethyl)glycine, D-Propargylglycine, L-C-Propargylglycine, Sarcosine, N,N-Dimethylglycine, N,N-Dimethylglycine ethyl ester, D-Chg-OH, α-Phosphonoglycine trimethyl ester, N-cyclobutylglycine [Ncbut], L-α-methylethylglycine [Metg], N-cycloheptylglycine [Nchep], L-α-methyl-i-butylglycine [Mtbug], N-methylglycine [Nmgly], L-N-methyl-ethylglycine [Nmetg], L-ethylglycine [Etg], L-N-methyl-t-butylglycine [Nmtbug], L-t-butylglycine [Tbug], N-cyclohexylglycine [Nchex], N-cyclodecylglycine [Ncdec], N-cyclododecylglycine [Ncdod], N-cyclooctylglycine [Ncoct], N-cyclopropylglycine [Ncpro], N-cycloundecylglycine [Ncund], N-(2-aminoethyl) glycine [Naeg], N—(N-(2,2-diphenylethyl) diphenylethyl) glycine [Nnbhm], N-(2,2-carbamylmethyl-glycine [Nbhm], N—(N-(3,3-diphenylpropyl) diphenylpropyl)glycine [Nnbhe] and N-(3,3-carbamylmethyl-glycine [Nbhe]. Each possibility represents a separate embodiment.

Non limiting examples for histidine non-conservative amino acids are: L-α-methylhistidine [Mhis], D-α-methylhistidine [Dmhis], L-N-methylhistidine [Nmhis], D-N-methylhistidine [Dnmhis], N-(imidazolylethyl)glycine [Nhis], and D-histidine [Dhis, (dH), h]. Each possibility represents a separate embodiment.

Non limiting examples for isoleucine non-conservative amino acids are: N-Methyl-L-isoleucine [Nmile], N-(3-Indolylacetyl)-L-isoleucine, allo-Ile-OH, D-allo-Isoleucine, L-β-Homoisoleucine, L-α-methylisoleucine [Mile], D-α-methylisoleucine [Dmile], D-N-methylisoleucine [Dnmile], N-(1-methylpropyl)glycine [Nile], and D-isoleucine [Dile, (dD), i]. Each possibility represents a separate embodiment.

Non limiting examples for leucine non-conservative amino acids are: D-Ileuine [Dleu, (dL), l]. Cycloleucine, DL-leucine, N-Formyl-Leu-OH, D-tert-Leucine, L-tert-Leucine, DL-tert-Leucine, L-tert-Leucine methyl ester, 5,5,5-Trifluoro-DL-leucine, D-β-Leu-OH, L-β-Leucine, DL-β-Leucine, L-β-Homoleucine, DL-β-Homoleucine, L-N-methyl-leucine [Nmleu], D-N-methyl-leucine [Dnmleu], L-α-methyl-leucine [Mleu], D-α-methyl-leucine [Dmleu], N-(2-methylpropyl)glycine [Nleu], D-Ileucine [Dleu, l], D-Norleucine, L-Norleucine, DL-Norleucine, L-N-methyl-norleucine [Nmnle] and L-norleucine [Nle]. Each possibility represents a separate embodiment.

Non limiting examples for lysine non-conservative amino acids are: DL-5-Hydroxylysine, (5R)-5-Hydroxy-L-lysine, β-Lys-OH, L-β-Homolysine, L-α-methyl-lysine [Mlys], D-α-methyl-lysine [Dmlys], L-N-methyl-lysine [Nmlys], D-N-methyl-lysine [Dnmlys], N-(4-aminobutyl)glycine [Nlys], and D-lysine [Dlys, (dK), k]. Each possibility represents a separate embodiment.

Non limiting examples for methionine non-conservative amino acids are: L-β-Homomethionine, DL-β-Homomethionine, L-α-methylmethionine [Mmet], D-α-methylmethionine [Dmmet], L-N-methylmethionine [Nmmet], D-N-methylmethionine [Dnmmet], N-(2-methylthioethyl)glycine [Nmet], and D-methionine [Dmet, (dM), in]. Each possibility represents a separate embodiment.

Non limiting examples for phenylalanine non-conservative amino acids are: N-Acetyl-2-fluoro-DL-phenylalanine, N-Acetyl-4-fluoro-DL-phenylalanine, 4-Amino-L-phenylalanine, 3-[3,4-bis(trifluoromethyl)phenyl]-L-alanine, Bpa-OH, D-Bpa-OH, 4-tert-butyl-Phe-OH, 4-tert-butyl-D-Phe-OH, 4-(amino)-L-phenylalanine, rac-β$^2$-homophenylalanine, 2-methoxy-L-phenylalanine, (S)-4-methoxy-β-Phe-OH, 2-nitro-L-phenylalanine, pentafluoro-D-phenylalanine, pentafluoro-L-phenylalanine, Phe(4-Br)—OH, D-Phe(4-Br)—OH, Phe(2-CF$_3$)—OH, D-Phe(2-CF$_3$)—OH, Phe(3-CF$_3$)—OH, D-Phe(3-CF$_3$)—OH, Phe(4-CF$_3$)—OH, D-Phe(4-CF$_3$)—OH, Phe(2-Cl)—OH, D-Phe(2-Cl)—OH, Phe(2,4-Cl$_2$)—OH, D-Phe(2,4-Cl$_2$)—OH, D-Phe(3-Cl)—OH, Phe(3,4-Cl$_2$)—OH, Phe(4-Cl)—OH, D-Phe(4-Cl)—OH, Phe(2-CN)—OH, D-Phe(2-CN)—OH, D-Phe(3-CN)—OH, Phe(4-CN)—OH, D-Phe(4-CN)—OH, Phe(2-Me)-OH, D-Phe(2-Me)-OH, Phe(3-Me)-OH, D-Phe(3-Me)-OH, Phe(4-Me)-OH, Phe(4-NH$_2$)—OH, Phe(4-NO$_2$)—OH, Phe(2-F)—OH, D-Phe(2-F)—OH, Phe(3-F)—OH, D-Phe(3-F)—OH, Phe(3,4-F$_2$)—OH, Phe(3,4-F$_2$)—OH, Phe(3,5-F$_2$)—OH, Phe(4-F)—OH, D-Phe(4-F)—OH, Phe(4-I)—

OH, D-3,4,5-trifluorophenylalanine, p-Bromo-DL-phenylalanine, 4-Bromo-L-phenylalanine, β-phenyl-D-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, N-[(9H-Fluoren-9-ylmethoxy)carbonyl]-2-methoxy-L-phenylalanine, o-Fluoro-DL-phenylalanine, m-Fluoro-L-phenylalanine, m-Fluoro-DL-phenylalanine, p-Fluoro-L-phenylalanine, p-Fluoro-DL-phenylalanine, 4-Fluoro-D-phenylalanine, 2-fluoro-L-phenylalanine methyl ester, p-fluoro-DL-Phe-OMe, D-3-bromophenylalanine, D-4-bromophenylalanine, L-β-(6-chloro-4-pyridinyl)alanine, D-3,5-difluorophenylalanine, L-3-fluorophenylalanine, L-4-fluorophenylalanine, L-β-(1H-5-indolyl)alanine, 2-nitro-L-phenylalanine, pentafluoro-L-phenylalanine, phe(3-br)-oh, Phe(4-Br)—OH, Phe(2-$CF_3$)—OH, D-Phe(2-$CF_3$)—OH, Phe(3-$CF_3$)—OH, D-Phe(3-$CF_3$)—OH, Phe(4-$CF_3$)—OH, D-Phe(4-$CF_3$)—OH, Phe(2-Cl)—OH, D-Phe(2-Cl)—OH, Phe(2,4-$Cl_2$)—OH, D-Phe(2,4-$Cl_2$)—OH, Phe(3,4-$Cl_2$)—OH, D-Phe(3,4-$Cl_2$)—OH, Phe(4-Cl)—OH, D-Phe(4-Cl)—OH, Phe(2-CN)—OH, D-Phe(2-CN)—OH, D-Phe(3-CN)—OH, Phe(4-CN)—OH, Phe(2-Me)-OH, Phe(3-Me)-OH, D-Phe(3-Me)-OH, Phe(4-$NO_2$)—OH, D-Phe(4-$NO_2$)—OH, D-Phe(2-F)—OH, Phe(3-F)—OH, D-Phe(3-F)—OH, Phe(3,4-$F_2$)—OH, Phe(3,5-$F_2$)—OH, D-Phe(4-F)—OH, Phe(4-I)—OH, D-Phe(4-I)—OH, 4-(phosphonomethyl)-Phe-OH, L-4-trifluoromethylphenylalanine, 3,4,5-trifluoro-D-phenylalanine, L-3,4,5-trifluoro-phenylalanine, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, α-Methyl-DL-phenylalanine methyl ester, 4-Nitro-D-phenylalanine, 4-Nitro-L-phenylalanine, 4-Nitro-DL-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 3,3',5-Triiodo-L-thyronine, (R)-4-bromo-3-Phe-OH, N-Acetyl-DL-β-phenylalanine, (S)-4-bromo-3-Phe-OH, (R)-4-chloro-3-Homophe-OH, (S)-4-chloro-3-Homophe-OH, (R)-4-chloro-3-Phe-OH, (S)-4-chloro-β-Phe-OH, (S)-2-cyano-3-Homophe-OH, (R)-4-cyano-β-Homophe-OH, (S)-4-cyano-3-Homophe-OH, (R)-3-cyano-β-Phe-OH, (R)-4-cyano-β-Phe-OH, (S)-4-cyano-β-Phe-OH, (R)-3,4-dimethoxy-β-Phe-OH, (S)-3,4-dimethoxy-β-Phe-OH, (R)-4-fluoro-β-Phe-OH, (S)-4-fluoro-β-Phe-OH, (S)-4-iodo-β-Homophe-OH, (S)-3-cyano-3-Homophe-OH, (S)-3,4-difluoro-β-Homophe-OH, (R)-4-fluoro-3-Homophe-OH, (S)-β2-homophenylalanine, (R)-3-methoxy-3-Phe-OH, (S)-3-methoxy-3-Phe-OH, (R)-4-methoxy-β-Phe-OH, (S)-4-methyl-β-Homophe-OH, (R)-2-methyl-β-Phe-OH, (S)-2-methyl-β-Phe-OH, (R)-3-methyl-3-Phe-OH, (S)-3-methyl-3-Phe-OH, (R)-4-methyl-β-Phe-OH, (S)-4-methyl-β-Phe-OH, β-Phe-OH, D-β-Phe-OH, (S)-2-(trifluoromethyl)-β-Homophe-OH, (S)-2-(trifluoromethyl)-3-Homophe-OH, (S)-3-(trifluoromethyl)-β-Homophe-OH, (R)-4-(trifluoromethyl)-3-Homophe-OH, (S)-2-(trifluoromethyl)-β-Phe-OH, (R)-3-(trifluoromethyl)-β-Phe-OH, (S)-3-(trifluoromethyl)-3-Phe-OH, (R)-4-(trifluoromethyl)-β-Phe-OH, (S)-4-(trifluoromethyl)-3-Phe-OH, β-Homophe-OH, D-β-Homophe-OH, (S)-2-methyl-β-Homophe-OH, (S)-3-methyl-β-Homophe-OH, β-Phe-OH, β-D-Phe-OH, (S)-3-(trifluoromethyl)-β-Homophe-OH, L-β-Homophenylalanine, DL-β-Homophenylalanine, DL-β-Phenylalanine, DL-homophenylalanine methyl ester, D-Homophenylalanine, L-Homophenylalanine, DL-Homophenylalanine, D-Homophenylalanine ethyl ester, (R)-$β^2$-homophenylalanine, L-α-methyl-homophenylalanine [Mhphe], L-α-methylphenylalanine [Mphe], D-α-methylphenylalanine [Dmphe], L-N-methyl-homophenylalanine [Nm phe], L-homophenylalanine [Hphe], L-N-methylphenylalanine [Nmphe], D-N-methylphenylalanine [Dnmphe], N-benzylglycine [Nphe] and D-phenylalanine [Dphe, (dF), f]. Each possibility represents a separate embodiment.

Non limiting examples for proline non-conservative amino acids are: homoproline (hPro), (4-hydroxy)Pro (4HyP), (3-hydroxy)Pro (3HyP), gamma-benzyl-proline, gamma-(2-fluoro-benzyl)-proline, gamma-(3-fluoro-benzyl)-proline, gamma-(4-fluoro-benzyl)-proline, gamma-(2-chloro-benzyl)-proline, gamma-(3-chloro-benzyl)-proline, gamma-(4-chloro-benzyl)-proline, gamma-(2-bromo-benzyl)-proline, gamma-(3-bromo-benzyl)-proline, gamma-(4-bromo-benzyl)-proline, gamma-(2-methyl-benzyl)-proline, gamma-(3-methyl-benzyl)-proline, gamma-(4-methyl-benzyl)-proline, gamma-(2-nitro-benzyl)-proline, gamma-(3-nitro-benzyl)-proline, gamma-(4-nitro-benzyl)-proline, gamma-(1-naphthalenylmethyl)-proline, gamma-(2-naphthalenylmethyl)-proline, gamma-(2,4-dichloro-benzyl)-proline, gamma-(3,4-dichloro-benzyl)-proline, gamma-(3,4-difluoro-benzyl)-proline, gamma-(2-trifluoro-methyl-benzyl)-proline, gamma-(3-trifluoro-methyl-benzyl)-proline, gamma-(4-trifluoro-methyl-benzyl)-proline, gamma-(2-cyano-benzyl)-proline, gamma-(3-cyano-benzyl)-proline, gamma-(4-cyano-benzyl)-proline, gamma-(2-iodo-benzyl)-proline, gamma-(3-iodo-benzyl)-proline, gamma-(4-iodo-benzyl)-proline, gamma-(3-phenyl-allyl-benzyl)-proline, gamma-(3-phenyl-propyl-benzyl)-proline, gamma-(4-tert-butyl-benzyl)-proline, gamma-benzhydryl-proline, gamma-(4-biphenyl-methyl)-proline, gamma-(4-thiazolyl-methyl)-proline, gamma-(3-benzothienyl-methyl)-proline, gamma-(2-thienyl-methyl)-proline, gamma-(3-thienyl-methyl)-proline, gamma-(2-furanyl-methyl)-proline, gamma-(2-pyridinyl-methyl)-proline, gamma-(3-pyridinyl-methyl)-proline, gamma-(4-pyridinyl-methyl)-proline, gamma-allyl-proline, gamma-propynyl-proline, alpha-modified-proline residues, pipecolic acid, azetidine-3-carboxylicacid, L-β-Homoproline, L-$β^3$-homoproline, L-β-Homohydroxyproline, hydroxyproline [Hyp], L-α-methylproline [Mpro], D-α-methylproline [Dmpro], L-N-methylproline [Nmpro], D-N-methylproline [Dnmpro], and D-proline [Dpro, (dP), p]. Each possibility represents a separate embodiment.

Non limiting examples for serine non-conservative amino acids are: (2R,3S)-3-phenylisoserine, D-cycloserine, L-Isoserine, DL-Isoserine, DL-3-Phenylserine, L-β-Homoserine, D-Homoserine, D-Homoserine, L-3-Homoserine, L-homoserine, L-α-methylserine [Mser], D-α-methylserine [Dmser], L-N-methylserine [Nmser], D-N-methylserine [Dnmser], D-serine [Dser, (dS), s], N-(hydroxymethyl)glycine [Nser] and phosphoserine [pSer]. Each possibility represents a separate embodiment.

Non limiting examples for threonine non-conservative amino acids are: L-allo-Threonine, D-Thyroxine, L-β-Homothreonine, L-α-methylthreonine [Mthr], D-α-methylthreonine [Dmthr], L-N-methylthreonine [Nmthr], D-N-methylthreonine [Dnmthr], D-threonine [Dthr, (dT), t], N-(1-hydroxyethyl)glycine [Nthr] and phosphothreonine [pThr]. Each possibility represents a separate embodiment.

Non limiting examples for tryptophan non-conservative amino acids are: 5-Fluoro-L-tryptophan, 5-Fluoro-DL-tryptophan, 5-Hydroxy-L-tryptophan, 5-Methoxy-DL-tryptophan, L-abrine, 5-Methyl-DL-tryptophan, H-Tpi-OMe. β-Homotrp-OMe, L-β-Homotryptophan, L-α-methyltryptophan [Mtrp], D-α-methyltryptophan [Dmtrp], L-N-methyltryptophan [Nmtrp], D-N-methyltryptophan [Dnmtrp], N-(3-indolylethyl)glycine [Nhtrp], D-tryptophan [Dtrp, (dW), w]. Each possibility represents a separate embodiment.

Non limiting examples for tyrosine non-conservative amino acids are: 3,5 diiodotyrosine (3,5-dITyr), 3,5 diBromotyrosine (3,5-dBTyr), homotyrosine, D-tyrosine, 3-amino-L-tyrosine, 3-amino-D-tyrosine, 3-iodo-L-tyrosine, 3-iodo-D-tyrosine, 3-methoxy-L-tyrosine, 3-methoxy-D-tyrosine, L-thyroxine, D-thyroxine, L-thyronine, D-thyronine, O-methyl-L-tyrosine, O-methyl-D-tyrosine, D-thyronine, O-ethyl-L-tyrosine, O-ethyl-D-tyrosine, 3,5,3'-triiodo-L-thyronine, 3,5,3'-triiodo-D-thyronine, 3,5-diiodo-L-thyronine, 3,5-diiodo-D-thyronine, D-meta-tyrosine, L-meta-tyrosine, D-ortho-tyrosine, L-ortho-tyrosine, phenylalanine, substituted phaenylalanine, N-nitro phenylalanine, p-nitro phenylalanine, 3-chloro-Dtyr-oh, Tyr(3,5-diI), 3-Chloro-L-tyrosine, Tyr(3-NO$_2$)—OH, Tyr(3,5-diI)—OH, N-Me-Tyr-OH, α-Methyl-DL-tyrosine, 3-Nitro-L-tyrosine, DL-o-Tyrosine, β-Homotyr-OH, (R)-β-Tyr-OH, (S)-β-Tyr-OH, L-α-methyltyrosine [Mtyr], D-α-methyltyrosine [Dmtyr], L-N-methyltyrosine [Nmtyr], D-N-methyltyrosine [Dnmtyr], D-tyrosine [Dtyr, (dY), y], O-methyl-tyrosine, and phosphotyrosine [pTyr]. Each possibility represents a separate embodiment.

Non limiting examples for valine non-conservative amino acids are: 3-Fluoro-DL-valine, 4,4,4,4',4',4'-Hexafluoro-DL-valine, D-valine [Dval, (dV), v], N-Me-Val-OH [Nmval], N-Me-Val-OH, L-α-methylvaline [Mval], D-α-methylvaline [Dmval], (R)-(+)-α-Methylvaline, (S)-(-)-α-Methylvaline and D-N-methylvaline [Dnmval]. Each possibility represents a separate embodiment.

Other non-natural amino acids that may be substituted as non-conservative replacements include: Ornithine and its modifications: D-Ornithine [Dorn], L-Ornithine [Orn], DL-Ornithine, L-α-methylornithine [Morn], D-α-methylornithine [Dmorn], L-N-methylornithine [Nmorn], D-N-methylornithine [Dnmorn] and N-(3-aminopropyl)glycine [Norn]. Each possibility represents a separate embodiment.

Alicyclic amino acids: L-2,4-Diaminobutyric acid, L-2,3-Diaminopropionic Acid, N-Me-Aib-OH, (R)-2-(amino)-5-hexynoic acid, piperidine-2-carboxylic acid, aminonorbornyl-carboxylate [Norb], alpha-aminobutyric acid [Abu], aminocyclopropanecarboxylate [Cpro], (cis)-3-Aminobicyclo[2.2.1]heptane-2-carboxylic acid, exo-cis-3-Aminobicyclo[2.2.1]hept-5-ene-2-carboxylic acid, 1-Amino-1-cyclobutanecarboxylic acid, cis-2-Aminocycloheptanecarboxylic acid, 1-Aminocyclohexanecarboxylic acid, cis-2-Aminocyclohexanecarboxylic acid, trans-2-Aminocyclohexanecarboxylic acid, cis-6-Amino-3-cyclohexene-1-carboxylic acid, 2-(1-Aminocyclohexyl)acetic acid, cis-2-Amino-1-cyclooctanecarboxylic acid, cis-2-Amino-3-cyclooctene-1-carboxylic acid, (1R,2S)-(-)-2-Amino-1-cyclopentanecarboxylic acid, (1S,2R)-(+)-2-Amino-1-cyclopentanecarboxylic acid, cis-2-Amino-1-cyclopentanecarboxylic acid, 2-(1-Aminocyclopentyl)acetic acid, cis-2-Amino-2-methylcyclohexanecarboxylic acid, cis-2-Amino-2-methylcyclopentanecarboxylic acid, 3-Amino-3-(4-nitrophenyl)propionic acid, 3-Azetidinecarboxylic acid, amchc-oh, 1-aminocyclobutane carboxylic acid, 1-(amino)cyclohexanecarboxylic acid, cis-2-(amino)-cyclohexanecarboxylic acid, trans-2-(amino)-cyclohexanecarboxylic acid, cis-4-(amino)cyclohexanecarboxylic acid, trans-4-(amino)cyclohexanecarboxylic acid, (±)-cis-2-(amino)-3-cyclohexene-1-carboxylic acid, (±)-cis-6-(amino)-3-cyclohexene-1-carboxylic acid, 2-(1-aminocyclohexyl)acetic acid, cis-[4-(amino)cyclohexyl]acetic acid, 1-(amino)cyclopentanecarboxylic acid, (±)-cis-2-(amino) cyclopentanecarboxylic acid, (1R,4S)-(+)-4-(amino)-2-cyclopentene-1-carboxylic acid, (±)-cis-2-(amino)-3-cyclopentene-1-carboxylic acid, 2-(1-aminocyclopentyl)acetic acid, 1-(amino)cyclopropanecarboxylic acid, Ethyl 1-aminocyclopropanecarboxylate, 1,2-trans-achec-oh, 1-(amino) cyclobutanecarboxylic acid, 1-(amino)cyclohexanecarboxylic acid, cis-2-(amino)-cyclohexanecarboxylic acid, trans-2-(amino)cyclohexanecarboxylic acid, cis-4-(amino) cyclohexanecarboxylic acid, trans-4-(amino) cyclohexanecarboxylic acid, cis-[4-(amino)cyclohexyl] acetic acid, 1-(amino)cyclopentanecarboxylic acid, (1R,4S)-(+)-4-(amino)-2-cyclopentene-1-carboxylic acid, (1S,4R)-(-)-4-(amino)-2-cyclopentene-1-carboxylic acid, 1-(amino) cyclopropanecarboxylic acid, trans-4-(aminomethyl) cyclohexanecarboxylic acid, β-Dab-OH, 3-Amino-3-(3-bromophenyl)propionic acid, 3-Aminobutanoic acid, cis-2-Amino-3-cyclopentene-1-carboxylic acid, DL-3-Aminoisobutyric acid, (R)-3-Amino-2-phenylpropionic acid, (±)-3-(amino)-4-(4-biphenylyl)butyric acid, cis-3-(amino)cyclohexanecarboxylic acid, (1S,3R)-(+)-3-(amino) cyclopentanecarboxylic acid, (2R,3R)-3-(amino)-2-hydroxy-4-phenylbutyric acid, (2S,3R)-3-(amino)-2-hydroxy-4-phenylbutyric acid, 2-(aminomethyl)phenylacetic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-3-(amino)-5-phenylpentanoic acid, (R)-3-(amino)-2-phenylpropionic acid, Ethyl 3-(benzylamino)propionate, cis-3-(amino)cyclohexanecarboxylic acid, (S)-3-(amino)-5-hexenoic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-(-)-Pyrrolidine-3-carboxylic acid, (S)-(+)-Pyrrolidine-3-carboxylic acid, N-methyl-7-aminobutyrate [Nmgabu], γ-aminobutyric acid [Gabu], N-methyl-α-amino-α-methylbutyrate [Nmaabu], α-amino-α-methylbutyrate [Aabu], N-methyl-α-aminoisobutyrate [Nmaib], α-aminoisobutyric acid [Aib], α-methyl-γ-aminobutyrate [Mgabu]. Each possibility represents a separate embodiment.

Phenyl glycine and its modifications: Phg-OH, D-Phg-OH, 2-(piperazino)-2-(3,4-dimethoxyphenyl)acetic acid, 2-(piperazino)-2-(2-fluorophenyl)acetic acid, 2-(4-piperazino)-2-(3-fluorophenyl)acetic acid, 2-(4-piperazino)-2-(4-methoxyphenyl)acetic acid, 2-(4-piperazino)-2-(3-pyridyl) acetic acid, 2-(4-piperazino)-2-[4-(trifluoromethyl)phenyl] acetic acid, L-(+)-2-Chlorophenylglycine, (+)-2-Chlorophenylglycine, (±)-4-Chlorophenylglycine, (R)-(-)-2-(2,5-Dihydrophenyl)glycine, (R)-(-)-N-(3,5-Dinitrobenzoyl)-α-phenylglycine, (S)-(+)-N-(3,5-Dinitrobenzoyl)-α-phenylglycine, 2,2-Diphenylglycine, 2-Fluoro-DL-α-phenylglycine, 4-Fluoro-D-α-phenylglycine, 4-Hydroxy-D-phenylglycine, 4-Hydroxy-L-phenylglycine, 2-Phenylglycine, D-(-)-α-Phenylglycine, D-(-)-α-Phenylglycine, DL-α-Phenylglycine, L-(+)-α-Phenylglycine, N-Phenylglycine, (R)-(-)-2-Phenylglycine methyl ester, (S)-(+)-2-Phenylglycine methyl ester, 2-Phenylglycinonitrile hydrochloride, α-Phenylglycinonitrile, 3-(Trifluoromethyl)-DL-phenylglycine, and 4-(Trifluoromethyl)-L-phenylglycine. Each possibility represents a separate embodiment.

Penicillamine and its modifications: N-Acetyl-D-penicillamine, D-Penicillamine, L-Penicillamine [Pen], DL-Penicillamine. α-methylpenicillamine [Mpen], N-methylpenicillamine [Nmpen]. Each possibility represents a separate embodiment.

β-Homopyrrolidine. Each possibility represents a separate embodiment.

Aromatic amino acids: 3-Acetamidobenzoic acid, 4-Acetamidobenzoic acid, 4-Acetamido-2-methylbenzoic acid, N-Acetylanthranilic acid, 3-Aminobenzoic acid, 3-Aminobenzoic acid hydrochloride, 4-Aminobenzoic acid, 4-Aminobenzoic acid, 4-Aminobenzoic acid, 4-Aminobenzoic acid, 4-Aminobenzoic acid, 4-Aminobenzoic acid, 2-Aminobenzophenone-2'-carboxylic acid, 2-Amino-4-bromobenzoic acid, 2-Amino-5-bromobenzoic acid, 3-Amino-2-bromobenzoic acid, 3-Amino-4-bromobenzoic acid, 3-Amino-5-bromobenzoic acid, 4-Amino-3-bromobenzoic acid, 5-Amino-2-bromobenzoic acid, 2-Amino-3-bromo-5-methylbenzoic acid, 2-Amino-3-chlorobenzoic acid, 2-Amino-4-chlorobenzoic acid, 2-Amino-5-chlorobenzoic acid, 2-Amino-5-chlorobenzoic acid, 2-Amino-6-chlorobenzoic acid, 3-Amino-2-chlorobenzoic acid, 3-Amino-4-chlorobenzoic acid, 4-Amino-2-chlorobenzoic acid, 4-Amino-3-chlorobenzoic acid, 5-Amino-2-chlorobenzoic acid, 5-Amino-2-chlorobenzoic acid, 4-Amino-5-chloro-2-methoxybenzoic acid, 2-Amino-5-chloro-3-methylbenzoic acid, 3-Amino-2,5-dichlorobenzoic acid, 4-Amino-3,5-dichlorobenzoic acid, 2-Amino-4,5-dimethoxybenzoic acid, 4-(2-Aminoethyl)benzoic acid hydrochloride, 2-Amino-4-fluorobenzoic acid, 2-Amino-5-fluorobenzoic acid, 2-Amino-6-fluorobenzoic acid, 4-Amino-2-fluorobenzoic acid, 2-Amino-5-hydroxybenzoic acid, 3-Amino-4-hydroxybenzoic acid, 4-Amino-3-hydroxybenzoic acid, 2-Amino-5-iodobenzoic acid, 5-Aminoisophthalic acid, 2-Amino-3-methoxybenzoic acid, 2-Amino-4-methoxybenzoic acid, 2-Amino-5-methoxybenzoic acid, 3-Amino-2-methoxybenzoic acid, 3-Amino-4-methoxybenzoic acid, 3-Amino-5-methoxybenzoic acid, 4-Amino-2-methoxybenzoic acid, 4-Amino-3-methoxybenzoic acid, 5-Amino-2-methoxybenzoic acid, 2-Amino-3-methylbenzoic acid, 2-Amino-5-methylbenzoic acid, 2-Amino-6-methylbenzoic acid, 3-(Aminomethyl)benzoic acid, 3-Amino-2-methylbenzoic acid, 3-Amino-4-methylbenzoic acid, 4-(Aminomethyl)benzoic acid, 4-Amino-2-methylbenzoic acid, 4-Amino-3-methylbenzoic acid, 5-Amino-2-methylbenzoic acid, 3-Amino-2-naphthoic acid, 6-Amino-2-naphthoic acid, 2-Amino-3-nitrobenzoic acid, 2-Amino-5-nitrobenzoic acid, 2-Amino-5-nitrobenzoic acid, 4-Amino-5-nitrobenzoic acid, 5-Amino-2-nitrobenzoic acid, 3-(4-Aminophenyl)propionic acid, 3-Aminophthalic acid, 4-Aminophthalic acid, 3-Aminosalicylic acid, 4-Aminosalicylic acid, 5-Aminosalicylic acid, 5-Aminosalicylic acid, 2-Aminoterephthalic acid, 2-Amino-3,4,5,6-tetrafluorobenzoic acid, 4-Amino-2,3,5,6-tetrafluorobenzoic acid, (R)-2-Amino-1,2,3,4-tetrahydronaphthalene-2-carboxylic acid, (S)-2-Amino-1,2,3,4-tetrahydro-2-naphthalenecarboxylic acid, 2-Amino-3-(trifluoromethyl)benzoic acid, 2-Amino-3-(trifluoromethyl)benzoic acid, 3-Amino-5-(trifluoromethyl)benzoic acid, 5-Amino-2,4,6-triiodoisophthalic acid, 2-Amino-3,4,5-trimethoxybenzoic acid, 2-Anilinophenylacetic acid, 2-Abz-OH, 3-Abz-OH, 4-Abz-OH, 2-(aminomethyl)benzoic acid, 3-(aminomethyl)benzoic acid, 4-(aminomethyl)benzoic acid, tert-Butyl 2-aminobenzoate, tert-Butyl 3-aminobenzoate, tert-Butyl 4-aminobenzoate, 4-(Butylamino)benzoic acid, 2,3-Diaminobenzoic acid, 3,4-Diaminobenzoic acid, 3,5-Diaminobenzoic acid, 3,5-Diaminoanthranilic acid, 3,5-Dichloroanthranilic acid, 4-(Diethylamino)benzoic acid, 4,5-Difluoroanthranilic acid, 4-(Dimethylamino)benzoic acid, 4-(Dimethylamino)benzoic acid, 3,5-Dimethylanthranilic acid, 5-Fluoro-2-methoxybenzoic acid, 2-Abz-OH, 3-Abz-OH, 4-Abz-OH, 3-(aminomethyl)benzoic acid, 4-(aminomethyl)benzoic acid, 4-(2-hydrazino)benzoic acid, 3-Hydroxyanthranilic acid, 3-Hydroxyanthranilic acid, Methyl 3-aminobenzoate, 3-(Methylamino)benzoic acid, 4-(Methylamino)benzoic acid, Methyl 2-amino-4-chlorobenzoate, Methyl 2-amino-4,5-dimethoxybenzoate, 4-Nitroanthranilic acid, N-Phenylanthranilic acid, N-Phenylanthranilic acid, and Sodium 4-aminosalicylate. Each possibility represents a separate embodiment.

Other amino acids: (S)-α-Amino-7-butyrolactone, DL-2-Aminocaprylic acid, 7-Aminocephalosporanic acid, 4-Aminocinnamic acid, (S)-(+)-α-Aminocyclohexanepropionic acid, (R)-Amino-(4-hydroxyphenyl)acetic acid methyl ester, 5-Aminolevulinic acid, 4-Amino-nicotinic acid, 3-Aminophenylacetic acid, 4-Aminophenylacetic acid, 2-Amino-2-phenylbutyric acid, 4-(4-Aminophenyl)butyric acid, 2-(4-Aminophenylthio)acetic acid, DL-α-Amino-2-thiopheneacetic acid, 5-Aminovaleric acid, 8-Benzyl (S)-2-aminooctanedioate, 4-(amino)-1-methylpyrrole-2-carboxylic acid, 4-(amino)tetrahydrothiopyran-4-carboxylic acid, (1R,3S,4S)-2-azabicyclo[2.2.1]heptane-3-carboxylic acid, L-azetidine-2-carboxylic acid, azetidine-3-carboxylic acid, 4-(amino)piperidine-4-carboxylic acid, diaminoacetic acid, Inp-OH, (R)-Nip-OH, (S)-4-oxopiperidine-2-carboxylic acid, 2-(4-piperazino)-2-(4-fluorophenyl)acetic acid, 2-(4-piperazino)-2-phenylacetic acid, 4-piperidineacetaldehyde, 4-piperidylacetic acid, (−)-L-thioproline, Tie-OH, 3-piperidinecarboxylic acid, L-(+)-canavanine, (±)-carnitine, chlorambucil, 2,6-diaminopimelic acid, meso-2,3-diaminosuccinic acid, 4-(dimethylamino)cinnamic acid, 4-(dimethylamino)phenylacetic acid, ethyl (S)—N-Boc-piperidine-3-carboxylate, ethyl piperazinoacetate, 4-[2-(amino)ethyl]piperazin-1-ylacetic acid, (R)-4-(amino)-5-phenylpentanoic acid, (S)-azetidine-2-carboxylic acid, azetidine-3-carboxylic acid, guvacine, Inp-OH, (R)-Nip-OH, DL-Nip-OH, 4-phenyl-piperidine-4-carboxylic acid, 1-piperazineacetic acid, 4-piperidineacetic acid, (R)-piperidine-2-carboxylic acid, (S)-piperidine-2-carboxylic acid, (S)-1,2,3,4-tetrahydronorharmane-3-carboxylic acid, Tic-OH, D-Tic-OH, Iminodiacetic acid, Indoline-2-carboxylic acid, DL-Kynurenine, L-aziridine-2-carboxylate, Methyl 4-aminobutyrate, (S)-2-Piperazinecarboxylic acid, 2-(1-Piperazinyl)acetic acid, (R)-(−)-3-Piperidinecarboxylic acid, 2-Pyrrolidone-5-carboxylic acid, (R)-(+)-2-Pyrrolidone-5-carboxylic acid, (R)-1,2,3,4-Tetrahydro-3-isoquinolinecarboxylic acid, (S)-1,2,3,4-Tetrahydro-3-isoquinolinecarboxylic acid, L-4-Thiazolidinecarboxylic acid, (4R)-(−)-2-Thioxo-4-thiazolidinecarboxylic acid, hydrazinoacetic acid, and 3,3',5-Triiodo-L-thyronine. Each possibility represents a separate embodiment.

In some embodiments, the peptides comprise peptidomimetic compounds having further improved stability and cell permeability properties. Some embodiments comprise a peptide according to any of PEPTIDE ID NO: 1-176, 184-190, and 193-475, wherein said peptide bonds (—CO—NH—) within the peptide may be substituted, for example, by N-methylated amide bonds (—N(CH$_3$)—CO—), ester bonds (—C(═O)—O—), ketomethylene bonds (—CO—CH$_2$—), sulfinylmethylene bonds (—S(═O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH═CH—), fluorinated olefinic double bonds (—CF═CH—), or retro amide bonds (—NH—CO—), peptide derivatives (—N ($R^x$)—$CH_2$—CO—), wherein $R^x$ is the "normal" side chain, naturally present on the carbon atom. These modifications can occur at any of the bonds along the peptide chain and even at several (2-3) bonds at the same time. Each possibility represents a separate embodiment.

The present invention further provides conjugates comprising any of the peptides and analogs described herein conjugated to a moiety for extending half life or increasing cell penetration. For example, the half life extending moiety is a peptide or protein and the conjugate is a fusion peptide or chimeric peptide. Alternatively, the half life extending moiety is a polymer, e.g., a polyethylene glycol. The present disclosure furthermore provides dimers and multimers comprising any of the peptides and analogs described herein. Any moiety known in the art to facilitate actively or passively or enhance permeability of the compound into cells may be used for conjugation with the peptide core according to the present invention. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to a preferred embodiment, the hydrophobic moiety is a lipid moiety or an amino acid moiety. The permeability-enhancing moiety may be connected to any position in the peptide moiety, directly or through a spacer or linker, preferably to the amino terminus of the peptide moiety. The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds. Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRUIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-glycerol, 1,3-dipalmitoyl-2-succinylglycerol, 1,2-dipalmitoyl-3-succinylglycerol, l-hexadecyl-2-palmitoylglycerophosphatidylethanolamine, palmitoylhomocystiene, N,N'-bis (dodecyaminocarbonylmethylene)-N,N-bis((-N,N,N-trimethylammoniumethyl-amino carbonylmethylene)ethylenediamine tetraiodide; N,N"-bis(hexadecylaminocarbonylmethylene)-N,N, N"-tris((-N, N,N-trimethylammonium-ethylaminocarbonylmethylenediethylenetri amine hexaiodide; N,N-Bis (dodecylaminocarbonylmethylene)-N,N"-bis((-N,N,N-trimethylammonium ethylaminocarbonylmethylene) cyclohexylene-1,4-diamine tetraiodide; 1,7,7-tetra-((-N,N, N,N-tetramethylammoniumethylamino-carbonylmethylene)-3-hexadecylarninocarbonyl-methylene-1,3,7-triaazaheptane heptaiodide; N,N,N',N'-tetra((-N,N,N-trimethylammonium-ethylaminocarbonylmethylene)-N-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-α-D-mannopyranoside, 12-(((7'-diethylamino-coumarin-3-yl)carbonyl) methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-3-succinyl-glycerol; 1,3-dipalmitoyl-2-succinylglycerol, 1-hexadecyl-2-palmitoylglycero-phosphoethanolamine, and palmitoylhomocysteine.

The peptides of the present invention may be attached (either covalently or non-covalently) to a penetrating agent. As used herein the phrase "penetrating agent" refers to an agent which enhances translocation of any of the attached peptide across a cell membrane. Typically, peptide based penetrating agents have an amino acid composition containing either a high relative abundance of positively charged amino acids such as lysine or arginine, or have sequences that contain an alternating pattern of polar/charged amino acids and non-polar, hydrophobic amino acids. Such CPP may include polyArg [R(n)) where $4<n<17$ (e.g., n=5, 6, 7, 8, 9, 10, 11, 12, 13, 14, 15 or 16) (PEPTIDE ID NO: 177; SEQ ID NOS: 3-14). By way of a non-limiting example, cell penetrating peptide (CPP) sequences may be used in order to enhance intracellular penetration. In other embodiments, it is desirable to separate the highly charged CPP from the inhibitor peptide with a linker. Any of a variety of linkers can be used. The size of the linker can range, e.g., from 1-7 or even more amino acids (e.g., 1, 2, 3, 4, 5, 6 or 7 amino acids). In some embodiments, the linker can be -GG- (PEPTIDE ID NO: 178) or -GGSGG- (PEPTIDE ID NO: 179; SEQ ID NO: 15) fused to the inhibitory peptide. CPPs may include short and long versions of the protein transduction domain (PTD) of HIV TAT protein, such as for example, YARAAARQARA (PEPTIDE ID NO: 180; SEQ ID NO: 16), YGRKKRR (PEPTIDE ID NO: 181; SEQ ID NO: 17), YGRKKRRQRRR (PEPTIDE ID NO: 182; SEQ ID NO: 18), or RRQRR (PEPTIDE ID NO: 183; SEQ ID NO: 19). However, the disclosure is not so limited, and any suitable penetrating agent may be used, as known by those of skill in the art. Another method of enhancing cell penetration is via N-terminal myristoilation. In this protein modification, a myristoyl group (derived from myristic acid) is covalently attached via an amide bond to the alpha-amino group of an N-terminal amino acid of the peptide. Some technologies are described in. Soriaga, et al. "A Designed Inhibitor of p53 Aggregation Rescues p53 Tumor Suppression in Ovarian Carcinomas." Cancer Cell, 29, no. 1 (Jan. 11, 2016): 90-103. Other cell penetrating technology includes that found in patent publications WO2016102339; WO2014131892; WO2016087842; WO2014041505; WO2013098337, WO2010012850; WO2014147193; WO2014001229; WO2015075747, WO2012090150, WO2014056813, WO2014009259 and WO2011157713. In particular, technology for assisting compounds for penetrating the blood brain barrier includes that found in patent publications WO2015124540; WO2014033074, WO2006026184, WO2000009073, WO2006026184, WO2007036021, and WO2013106577.

An embodiment of the invention comprises a CPP of a peptide of Formula I selected from RRRRRRRRRR-GGSGG-rlkvrw (PEPTIDE ID NO: 454); RRRRRRRRRR-GGSGG-lelkikfw (PEPTIDE ID NO: 458); RRRRRRRRRR-GGSGG-elkivw (PEPTIDE ID NO: 468); RRRRRRRRRR-GGSGG-tlkivw (PEPTIDE ID NO: 472); RRRRRRRRRR-GGSGG-wkvqvrlw (PEPTIDE ID NO: 466); RRRRRRRRRR-GGSGG-wrlkvrww (PEPTIDE ID NO: 465); RRRRRRRRRR-GGSGG-wrlkvrww (PEPTIDE ID NO:463); and YGRKKRRQRRR-GGSGG-wrlkvrww (PEPTIDE ID NO: 469); or a pharmaceutically acceptable salt thereof.

An embodiment of the invention comprises a CPP of a peptide of Formula I selected from RRRRRRRRRR-GGSGG-lelkikfw (PEPTIDE ID NO: 458); RRRRRRRRRR-GGSGG-elkivw (PEPTIDE ID NO: 468); RRRRRRRRRR-GGSGG-tlkivw (PEPTIDE ID NO: 472); RRRRRRRRRR-GGSGG-wkvqvrlw (PEPTIDE ID NO: 466); RRRRRRRRRR-GGSGG-wrlkvrww (PEPTIDE ID NO: 465); RRRRRRRRRR-GGSGG-wrlkvrww (PEPTIDE ID NO:463); and YGRKKRRQRRR-GGSGG-wrlkvrww (PEPTIDE ID NO: 469); or a pharmaceutically acceptable salt thereof.

According to some embodiments the peptide is modified, e.g it may include a duration enhancing moiety. The duration enhancing moiety can be a water soluble polymer, or a long chain aliphatic group. In some embodiments, a plurality of duration enhancing moieties are attached to the peptide, in which case each linker to each duration enhancing moiety is independently selected from the linkers described herein.

According to some embodiments the amino terminus of the peptide is modified, e.g., it may be acylated. According to additional embodiments the carboxy terminus is modified, e.g., it may be acylated, amidated, reduced or esterified. In accordance with some embodiments, the peptide comprises an acylated amino acid (e.g., a non-coded acylated amino acid (e.g., an amino acid comprising an acyl group which is non-native to a naturally-occurring amino acid)). In accordance with one embodiment, the peptide comprises an acyl group which is attached to the peptide via an ester, thioester, or amide linkage for purposes of prolonging half-life in circulation and/or delaying the onset of and/or extending the duration of action and/or improving resistance to proteases. Acylation can be carried out at any position within the peptide, (e.g., the amino acid at the C-terminus), provided that activity is retained, if not enhanced. The peptide in some embodiments can be acylated at the same amino acid position where a hydrophilic moiety is linked, or at a different amino acid position. The acyl group can be covalently linked directly to an amino acid of the peptide, or indirectly to an amino acid of the peptide via a spacer, wherein the spacer is positioned between the amino acid of the peptide and the acyl group.

In specific aspects, the peptide is modified to comprise an acyl group by direct acylation of an amine, hydroxyl, or thiol of a side chain of an amino acid of the peptide. In this regard, the acylated peptide can comprise the amino acid sequence of any of PEPTIDE ID NO: 1-176, 184-190, and 193-475, or a modified amino acid sequence thereof comprising one or more of the amino acid modifications described herein.

In some embodiments, the peptide comprises a spacer between the analog and the acyl group. In some embodiments, the peptide is covalently bound to the spacer, which is covalently bound to the acyl group. In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COOH (e.g., Lys, Orn, Ser, Asp, or Glu) is suitable. In some embodiments, the spacer is an amino acid comprising a side chain amine, hydroxyl, or thiol, or a dipeptide or tripeptide comprising an amino acid comprising a side chain amine, hydroxyl, or thiol. When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp, Glu, homoglutamic acid, homocysteic acid, cysteic acid, gamma-glutamic acid. In the instance in which the side chain amine of the amino acid of the spacer is acylated, the amino acid of the spacer is an amino acid comprising a side chain amine. In this instance, it is possible for both the alpha amine and the side chain amine of the amino acid of the spacer to be acylated, such that the peptide is diacylated. Embodiments include such diacylated molecules. When acylation occurs through a hydroxyl group of a spacer, the amino acid or one of the amino acids of the dipeptide or tripeptide can be Ser. When acylation occurs through a thiol group of a spacer, the amino acid or one of the amino acids of the dipeptide or tripeptide can be Cys. In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid. In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups. The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a $C_{12}$ to $C_{18}$ fatty acyl group, e.g., $C_{14}$ fatty acyl group, $C_{16}$ fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms. In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methylalanine (Me-Ala), aminobutyric acid (Abu), γ-aminobutyric acid (7-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), 7-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (x, Met(O)), methionine-sulfone (Met($O_2$)), norleucine (u, Nle), methyl-norleucine (Me-Me), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4-tetrahydroisoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, 7-aminobutyric acid-7-aminobutyric acid, Glu-Glu, and γ-Glu-γ-Glu.

Suitable methods of peptide acylation via amines, hydroxyls, and thiols are known in the art. See, for example, Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989). The acyl group of the acylated amino acid can be of any size, e.g., any length carbon chain, and can be linear or branched. In some specific embodiments, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid. In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid. In some embodiments, the peptide comprises an acylated amino acid by acylation of a long chain alkane on the peptide. In specific aspects, the long chain alkane comprises an amine, hydroxyl, or thiol group (e.g., octadecylamine, tetradecanol, and hexadecanethiol) which reacts with a carboxyl group, or activated form thereof, of the peptide. The carboxyl group, or activated form thereof, of the peptide can be part of a side chain of an amino acid (e.g., glutamic acid, aspartic acid) of the peptide or can be part of the analog backbone. In certain embodiments, the peptide is modified to comprise an acyl group by acylation of the long chain alkane by a spacer which is attached to the peptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form" of a carboxyl group refers to a carboxyl group with the general formula R(C=O)X, wherein X is a leaving group and R is the peptide or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects, in which a long chain alkane is acylated by the peptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

Also, in some embodiments, an amine, hydroxyl, or thiol group of the peptide is acylated with a cholesterol acid. In a specific embodiment, the peptide is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety.

The peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the peptide can of any of PEPTIDE ID NO: 1-176, 184-190, and 193-475, including any of the modifications described herein, in which at least one of the amino acids comprises an acyl group and at least one of the amino acids is covalently bonded to a hydrophilic moiety (e.g., PEG). In some embodiments, the acyl group is attached via a spacer comprising Cys, Lys, Orn, homo-Cys, or Ac-Phe, and the hydrophilic moiety is incorporated at a Cys residue.

Alternatively, the peptides can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with some embodiments, the peptide comprises an alkylated amino acid (e.g., a non-coded alkylated amino acid (e.g., an amino acid comprising an alkyl group which is non-native to a naturally-occurring amino acid)). Alkylation can be carried out at any positions within the peptides, including any of the positions described herein as a site for acylation, including but not limited to, any of amino acid positions, at a position within a C-terminal extension, or at the C-terminus, provided that the biological activity is retained. The alkyl group can be covalently linked directly to an amino acid of the peptides, or indirectly to an amino acid of the peptides via a spacer, wherein the spacer is positioned between the amino acid of the peptides and the alkyl group. The peptides may be alkylated at the same amino acid position where a hydrophilic moiety is linked, or at a different amino acid position. In specific aspects, the peptides are modified to comprise an alkyl group by direct alkylation of an amine, hydroxyl, or thiol of a side chain of an amino acid of the peptides. In this regard, the alkylated peptides can comprise an amino acid sequence with at least one of the amino acids modified to any amino acid comprising a side chain amine, hydroxyl, or thiol. In yet other embodiments, the amino acid comprising a side chain amine, hydroxyl, or thiol is a disubstituted amino acid. In some embodiments, the alkylated peptide comprises a spacer between the peptide and the alkyl group. In some embodiments, the peptide is covalently bound to the spacer, which is covalently bound to the alkyl group. In some exemplary embodiments, the peptide is modified to comprise an alkyl group by alkylation of an amine, hydroxyl, or thiol of a spacer, which spacer is attached to a side chain of an amino acid. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In some embodiments, the spacer is an amino acid comprising a side chain amine, hydroxyl, or thiol or a dipeptide or tripeptide comprising an amino acid comprising a side chain amine, hydroxyl, or thiol. When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the peptide is dialkylated. Embodiments of the invention include such dialkylated molecules. When alkylation occurs through a hydroxyl group of a spacer, the amino acid can be Ser. When alkylation occurs through a thiol group of spacer, the amino acid can be Cys. In some embodiments, the spacer is a hydrophilic bifunctional spacer. Suitable methods of peptide alkylation via amines, hydroxyls, and thiols are known in the art. For example, a Williamson ether synthesis can be used to form an ether linkage between a hydroxyl group of the peptides and the alkyl group. Also, a nucleophilic substitution reaction of the peptide with an alkyl halide can result in any of an ether, thioether, or amino linkage. The alkyl group of the alkylated peptides can be of any size, e.g., any length carbon chain, and can be linear or branched. In some embodiments, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_2$ alkyl, or a $C_{30}$ alkyl. In some embodiments, the alkyl group is a $C_8$ to $C_{20}$ alkyl, e.g., a $C_{14}$ alkyl or a $C_{16}$ alkyl. In some embodiments of the disclosure, the peptide comprises an alkylated amino acid by reacting a nucleophilic, long chain alkane with the peptide, wherein the peptide comprises a leaving group suitable for nucleophilic substitution. In specific aspects, the nucleophilic group of the long chain alkane comprises an amine, hydroxyl, or thiol group (e.g., octadecylamine, tetradecanol, and hexadecanethiol). The leaving group of the peptide can be part of a side chain of an amino acid or can be part of the peptide backbone. Suitable leaving groups include, for example, N-hydroxysuccinimide, halogens, and sulfonate esters. In certain embodiments, the peptide is modified to comprise an alkyl group by reacting the nucleophilic, long chain alkane with a spacer which is attached to the peptide, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group. With regard to these aspects of the disclosure, in which a long chain alkane is alkylated by the peptides or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane. Also, in some embodiments, alkylation can occur between the peptides and a cholesterol moiety. For example, the hydroxyl group of cholesterol can displace a leaving group on the long chain alkane to form a cholesterol-peptides product. The alkylated peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. Alternatively, the alkylated peptides can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In some embodiments, the peptide comprises at position 1 or 2, or at both positions 1 and 2, an amino acid which achieves resistance of the peptides to peptidase cleavage. In some embodiments, the peptide comprises at position 1 an amino acid selected from the group consisting of: D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA). In some embodiments, the peptide comprises at position 2 an amino acid selected from the group consisting of: D-serine, D-alanine, valine, glycine, N-methyl serine, N-methyl alanine, or alpha, aminoisobutyric acid. In some embodiments, the peptide comprises at position 2 an amino acid which achieves resistance of the peptide to peptidases and the amino acid which achieves resistance of the peptide to peptidases is not D-serine. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

In some embodiments, the peptide is modified by amino acid substitutions and/or additions that introduce a charged amino acid into the C-terminal portion of the analog. In some embodiments, such modifications enhance stability and solubility. As used herein the term "charged amino acid" or "charged residue" refers to an amino acid that comprises a side chain that is negative-charged (i.e., de-protonated) or positive-charged (i.e., protonated) in aqueous solution at physiological pH. In some aspects, these amino acid substitutions and/or additions that introduce a charged amino acid modifications are at a C-terminal position. In some embodiments, one, two or three (and in some instances, more than three) charged amino acids are introduced at the C-terminal position. In exemplary embodiments, one, two or all of the charged amino acids are negative-charged. The negative-charged amino acid in some embodiments is aspartic acid, glutamic acid, cysteic acid, homocysteic acid, or homoglutamic acid. In some aspects, these modifications increase solubility.

In accordance with some embodiments, the peptides disclosed herein are modified by truncation of the C-terminus by one or two amino acid residues. In this regard, the peptides can comprise the sequences (PEPTIDE ID NO: 1-176, 184-190, and 193-475), optionally with any of the additional modifications described herein.

In some embodiments, the peptide comprises a modified PEPTIDE ID NO: 1-176, 184-190, and 193-475 in which the carboxylic acid of the C-terminal amino acid is replaced with a charge-neutral group, such as an amide or ester. Accordingly, in some embodiments, the peptide is an amidated peptide, such that the C-terminal residue comprises an amide in place of the alpha carboxylate of an amino acid. As used herein a general reference to a peptide or analog is intended to encompass peptides that have a modified amino terminus, carboxy terminus, or both amino and carboxy termini. For example, an amino acid chain composing an amide group in place of the terminal carboxylic acid is intended to be encompassed by an amino acid sequence designating the standard amino acids.

In accordance with some embodiments, the peptides disclosed herein may be modified by conjugation on at least one amino acid residue. In this regard, the peptides can comprise the sequences (PEPTIDE ID NO: 1-176, 184-190, and 193-475), optionally with any of the additional conjugations described herein.

The invention further provides conjugates comprising one or more of the peptides described herein conjugated to a heterologous moiety. As used herein, the term "heterologous moiety" is synonymous with the term "conjugate moiety" and refers to any molecule (chemical or biochemical, naturally-occurring or non-coded) which is different from the peptides described herein. Exemplary conjugate moieties that can be linked to any of the analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments, a conjugate is provided comprising a peptide of the present invention and a plasma protein, wherein the plasma protein is selected from the group consisting of albumin, transferin, fibrinogen and globulins. In some embodiments, the plasma protein moiety of the conjugate is albumin or transferin.

The conjugate in some embodiments comprises one or more of the peptides described herein and one or more of: a different peptide (which is distinct from the peptides described herein), a polypeptide, a nucleic acid molecule, an antibody or fragment thereof, a polymer, a quantum dot, a small molecule, a toxin, a diagnostic agent, a carbohydrate, an amino acid. In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In some aspects, the polymer is a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is attached via non-covalent or covalent bonding to the peptide of the present disclosure. In certain aspects, the heterologous moiety is attached to the peptide of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. The peptide in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, copolymers thereof, and mixed polymers of these amino acids and others, e.g., serines, to confer desirable solubility properties on the resultant loaded carrier. Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-3-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Parabromophenacyl bromide also is useful; the reaction is preferably performed in 0.1 M sodium cacodylate at pH 6.0. Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions. Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group. Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981). In some embodiments, the peptide is conjugated to a heterologous moiety via covalent linkage between a side chain of an amino acid of the peptides and the heterologous moiety. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety. In some embodiments, the conjugate comprises a linker that joins the peptide to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long.

In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in some embodiments, the peptides are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC). For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE. Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain. Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004). Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety. In certain embodiments, a peptide described herein is inserted into a loop region within the immunoglobulin molecule. In other embodiments, a peptide described herein replaces one or more amino acids of a loop region within the immunoglobulin molecule.

The peptides described herein can be further modified to improve its solubility and stability in aqueous solutions at physiological pH, while retaining the biological activity. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995). In specific aspects, an amino acid residue of the peptides having a thiol is modified with a hydrophilic moiety such as PEG. In some embodiments, the thiol is modified with maleimide-activated PEG in a Michael addition reaction to result in a PEGylated analog comprising a thioether linkage. In some embodiments, the thiol is modified with a haloacetyl-activated PEG in a nucleophilic substitution reaction to result in a PEGylated analog comprising a thioether linkage. Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-($C_1$-$C_{10}$) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyalkylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by al-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog. In some embodiments, the peptide is conjugated to a hydrophilic moiety via covalent linkage between a side chain of an amino acid of the peptide and the hydrophilic moiety.

In some embodiments, the peptide is conjugated to a hydrophilic moiety via the side chain of an amino acid, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG). In some embodiments, the conjugate of the present disclosure comprises the peptide fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly (Gly-Pro), poly(Ser-Glu), etc. In some aspects, the rPEG comprises three different types of amino acids, e.g., poly (Gly-Ser-Glu). In specific aspects, the rPEG increases the half-life of the peptide. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the peptide of the present disclosure through a peptide bond or a proteinase cleavage site, or is inserted into the loops of the peptide of the present disclosure. The rPEG in some aspects comprises an affinity tag or is linked to a PEG that is greater than 5 kDa. In some embodiments, the rPEG confers the peptide of the present disclosure with an increased hydrodynamic radius, serum half-life, protease resistance, or solubility and in some aspects confers the analog with decreased immunogenicity.

The peptides comprising the sequences (PEPTIDE ID NO: 1-176, 184-190, and 193-475), optionally with any of the conjugations described herein are contemplated as an embodiment.

The invention further provides multimers or dimers of the peptides disclosed herein, including homo- or hetero-multimers or homo- or hetero-dimers. Two or more of the analogs can be linked together using standard linking agents and procedures known to those skilled in the art. For example, dimers can be formed between two peptides through the use of bifunctional thiol crosslinkers and bi-functional amine crosslinkers, particularly for the analogs that have been substituted with cysteine, lysine ornithine, homocysteine or acetyl phenylalanine residues. The dimer can be a homodimer or alternatively can be a heterodimer. In certain embodiments, the linker connecting the two (or more) analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

Peptides of the invention are made in a variety of ways known in the art. Suitable methods of de novo synthesizing peptides are described in, for example, Merrifield, J. Am. Chem. Soc, 85, 2149 (1963); Davis et al., Biochem. Intl., 10, 394-414 (1985); Larsen et al., J. Am. Chem. Soc, 115, 6247 (1993); Smith et al., J. Peptide Protein Res., 44, 183 (1994); O'Donnell et al., J. Am. Chem. Soc, 118, 6070 (1996); Stewart and Young, Solid Phase Peptide Synthesis, Freeman (1969); Finn et al., The Proteins, 3 ed., vol. 2, pp. 105-253 (1976); Erickson et al., The Proteins, $3^{rd}$ ed., vol. 2, pp. 257-527 (1976); and Chan et al., Fmoc Solid Phase Peptide Synthesis, Oxford University Press, Oxford, United Kingdom, 2005. The invention contemplates synthetic peptides.

Alternatively, the peptide is expressed recombinantly by introducing a nucleic acid encoding a peptide of the invention into host cells, which are cultured to express the peptide using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N.Y., 1994. Such peptides are purified from the culture media or cell pellets.

In some embodiments, the peptides of the disclosure are isolated. In some embodiments, the peptides of the disclosure are purified. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In some embodiments, the peptides described herein are commercially synthesized by companies, such as Innopep Inc. (San Diego, Calif.). In this respect, the peptides can be synthetic, recombinant, isolated, and/or purified.

In some embodiments, the peptides described herein can be provided in accordance with one embodiment as part of a kit. Accordingly, in some embodiments, a kit for administering a peptide, to a patient in need thereof is provided wherein the kit comprises a peptide as described herein.

In one embodiment, the kit is provided with a device for administering the composition to a patient, e.g., syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the peptide in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment, the kit comprises a syringe and a needle, and in one embodiment the sterile composition is prepackaged within the syringe.

A further embodiment includes a method of supplying a peptide for treating a disease, said method comprises reimbursing a physician, a formulary, a patient or an insurance company for the sale of said peptide.

A further embodiment of the invention includes a method of supplying a peptide for treating a disease, said method comprises reimbursing a physician, a formulary, a patient or an insurance company for the sale of said peptide.

Definitions

The terms "peptide" refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified peptides. A peptide may be monomeric or polymeric. In certain embodiments, "peptides" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "therapeutic peptide" refers to peptides or fragments or variants thereof, having one or more therapeutic and/or biological activities.

The term "analog" as used herein describes a peptide comprising one or more amino acid modifications, such as but not limited to substitution and/or one or more deletion and/or one or more addition of any one of the amino acid residues for any natural or unnatural amino acid, synthetic amino acids or peptidomimetics and/or the attachment of a side chain to any one of the natural or unnatural amino acids, synthetic amino acids or peptidomimetics at any available position. The addition or deletion of amino acid residues can take place at the N-terminal of the peptide and/or at the C-terminal of the peptide.

Peptide sequences are indicated using standard one- or three-letter abbreviations. Unless otherwise indicated, peptide sequences have their amino termini at the left and their carboxy termini at the right. A particular section of a peptide can be designated by amino acid residue number such as amino acids 3 to 6, or by the actual residue at that site such as Met3 to Gly6. A particular peptide sequence also can be described by explaining how it differs from a reference sequence.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If anywhere in this invention reference is made to a peptide, analog or derivative or peptides according to this invention comprising or not comprising G, P, A, V, L, I, M, C, F, Y, H, K, R, Q, N, E, D, S or T, without specifying further, amino acids are meant. If not otherwise indicated amino acids indicated with a single letter code in CAPITAL letters indicate the L-isoform, if however the amino acid is indicated with a lower case letter, this amino acid is used/applied as it's D-form. In formulas herein, the isoform(s) represented by the placeholder "Xaa" is defined on a case-by-case basis.

As used herein, the use of "b" (lower case b) in the context of a peptide sequence means "D-Cha" and D-cyclohexylalanine.

As used herein, the use of "u" (lower case u) in the context of a peptide sequence means "D-Nle" and refers to D-norleucine.

As used herein, the use of "x" (lower case x) in the context of a peptide sequence means "D-Met(O)" and D-methionine sulfone.

As used herein, the use of "z" (lower case z) in the context of a peptide sequence means "D-Cit" and refers to D-citruline.

If, due to typing errors, there are deviations from the commonly used codes, the commonly used codes apply. The amino acids present in the peptides of the present invention are, preferably, amino acids which can be coded for by a nucleic acid. As is apparent from the above examples, amino acid residues may be identified by their full name, their one-letter code, and/or their three-letter code. These three ways are fully equivalent.

A "non-conservative amino acid substitution" refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within +2 is included. In certain embodiments, those that are within +1 are included, and in certain embodiments, those within +0.5 are included. It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +2 is included, in certain embodiments, those that are within +1 are included, and in certain embodiments, those within +0.5 are included.

Other exemplary amino acid substitutions are set forth in Table 4.

TABLE 4

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg, |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein the term "charged amino acid" or "charged residue" refers to an amino acid that comprises a side chain that is negative-charged (i.e., de-protonated) or positive-charged (i.e., protonated) in aqueous solution at physiological pH. For example, negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

A skilled artisan will be able to determine suitable variants of peptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar peptides. In further embodiments, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, the skilled artisan can predict the importance of amino acid residues in a peptide that correspond to amino acid residues important for activity or structure in similar peptides. One skilled in the art may opt for chemically similar amino acid substitutions for such predicted important amino acid residues.

One skilled in the art can also analyze the three-dimensional structure and amino acid sequence in relation to that structure in similar peptides. In view of such information, one skilled in the art may predict the alignment of amino acid residues of a peptide with respect to its three-dimensional structure. In certain embodiments, one skilled in the art may choose to not make radical changes to amino acid residues predicted to be on the surface of the peptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

Size variants of the peptides described herein are specifically contemplated. Exemplary peptides are composed of 6 to 50 amino acids. All integer sub-ranges of 6-50 amino acids (e.g., 7-50 aa, 8-50 aa, 9-50 aa, 6-49 aa, 6-48 aa, 7-49 aa, and so on) are specifically contemplated as genera of the invention; and all integer values (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids) are contemplated as species of the invention. Size variants, like other variants described herein, can be screened to verify/select variants that retain a desired activity, such as aggregation inhibitory or anti-amyloid activity.

The term "derivative" as used herein means a chemically modified peptide, in which one or more side chains have been covalently attached to the peptide. The term "side chain" may also be referred to as a "substituent". A derivative comprising such side chains will thus be "derivatized" peptide or "derivatized" analog. The term may also refer to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated. The term may also refer to peptides of the invention as used herein which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

The term "substituent" or "side chain" as used herein means any suitable moiety bonded, in particular covalently bonded, to an amino acid residue, in particular to any available position on an amino acid residue. Typically, the suitable moiety is a chemical moiety.

The term "fatty acid" refers to aliphatic monocarboxylic acids having from 4 to 28 carbon atoms, it is preferably un-branched, and it may be saturated or unsaturated. In the present invention fatty acids comprising 10 to 16 amino acids are preferred.

The term "fatty diacid" refers to fatty acids as defined above but with an additional carboxylic acid group in the omega position. Thus, fatty diacids are dicarboxylic acids. In the present invention fatty acids comprising 14 to 20 amino acids are preferred.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homolog of a given sequence has greater than 80% sequence homology over a length of the given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. (Id). In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance.

The term "conformation" with respect to a protein is directed to the structural arrangement (folding) of a protein in space.

A "pharmaceutical composition" refers to a composition suitable for pharmaceutical use in an animal or human. A pharmaceutical composition comprises a pharmacologically and/or therapeutically effective amount of an active agent and a pharmaceutically acceptable carrier. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration. The term also encompasses any of the agents listed in the US Pharmacopeia for use in animals, including humans. Suitable pharmaceutical carriers and formulations are described in Remington's Pharmaceutical Sciences, 21st Ed. 2005, Mack Publishing Co, Easton.

Pharmaceutically acceptable carrier" or "pharmaceutically acceptable excipient" refers to compositions that do not produce adverse, allergic, or other untoward reactions when administered to an animal or a human. As used herein, "pharmaceutically acceptable carrier" or "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, the excipients will include isotonic agents, for example, sugars, polyalcohols such as mannitol, sorbitol, or sodium chloride in the composition. Additional examples of pharmaceutically acceptable excipients are wetting agents or minor amounts of auxiliary substances such as wetting or emulsifying agents, preservatives or buffers, which enhance the shelf life or effectiveness of the peptide.

As used herein the term "pharmaceutically acceptable salt" refers to salts of peptides that retain the biological activity of the parent peptide, and which are not biologically or otherwise undesirable. Many of the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, a "therapeutically effective amount" of a peptide that when provided to a subject in accordance with the disclosed and claimed methods effects biological activities such as treating aggregation.

As used herein, "aggregation" means the collection and association of peptide moieties, whether the resulting structure is regular or irregular, repeating or non-repeating, stable or unstable or with ordered or disordered native states. Such association can occur through intermolecular interactions, ionic bonds, hydrophobic interactions, hydrogen bonds, van der Waals forces, i.e. "London dispersion forces," and dipole-dipole bonds, or any force or substance that can result in the collection or association together of two or more peptides or peptide regions. As used herein, "aggregation" encompasses, for example, fibrillation, or the formation of fibrils. "Aggregation" also encompasses the formation of a steric zipper. As used herein, a "target protein" or "target polypeptide" means any peptide structure that has a tendency to form fibrils, for example amyloid fibrils.

As used herein, "steric zipper region," also referred to as a "steric zipper sequence" or "zipper-forming sequence," means a sequence of amino acid residues in an aggregating polypeptide, such as a fibril-forming polypeptide, that interacts with similar sequences on other polypeptides to form steric zipper constructs such as, for example, fibrils. In one example, a steric zipper region can involve an amino acid sequence in a 3 sheet which is capable of interdigitating with its neighboring n-sheet across an interface, often with a similar amino acid sequence on the neighboring n-sheet. Such interdigitation can occur through, for example, the side chains of the amino acid residues.

The terms "treat", "treating" and "treatment" refer refers to an approach for obtaining beneficial or desired clinical results. Further, references herein to "treatment" include references to curative, palliative and prophylactic treatment. The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

For clarity, the term "instructing" is meant to include information on a label approved by a regulatory agency, in addition to its commonly understood definition.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

When used herein "consisting of" excludes any element, step, or ingredient not specified in the claim element. "Consisting essentially of" means that the amino acid sequence can vary by about 1, 2, 3, 4, 5, 6, 7, 8, 9, 10, 11, 12, 13, 14, or 15% relative to the recited PEPTIDE ID NO: sequence and still retain biological activity, as described herein. When used herein, "consisting essentially of" does not exclude materials or steps that do not materially affect the basic and novel characteristics of the claim.

The term "Tau aggregates" is defined as Tau protein which has undergone the process of aggregation, namely assembly of the protein into a multimeric assembly of various unspecified size and shape. Tau amyloid or fibril is a specific case of aggregates which is characterized by ordered aggregation into ribbon-like fibril assemblies of varied and undefined length Tau monomer is defined as one protein molecule not in a multimeric or aggregated state.

Throughout this specification and the claims which follow, "Tau40" is isoform 2 of the human MAPT gene residues 1-441 (SEQ ID NO: 24). Other forms of Tau are also capable of aggregating, namely containing the microtubule binding region. Some of these constructs are listed below. The tau segment embodying residues Residues 244-394 of Tau40 is referred to as K12: [MQTAPVPMPDLKNVKSKIGSTENLKHQPGGGKVQI-VYKPVDLSKVTSKCGSLGNIH HKPGGGQVEVKSEKLDFKDRVQSKIGSLD-NITHVPGGGNKKIETHKLTFRENAKAKT DHGAEIVY, SEQ ID NO: 20]. The tau segment embodying residues Residues 244-372 of Tau40 is referred to as K18:

[MQTAPVPMPDLKNVKSKIGSTENLKHQPGGGKVQIVYKPVDLSKVTSK

CGSLGNIHHKPGGGQVEVKSEKLDFKDRVQSKIGSLDNITHVPGGGNKK

IE SEQ ID NO: 21].

The tau segment embodying residues Residues 244-372 of Tau40 and excluding residues 277-307 is referred to as K19:

[MQTAPVPMPDLKNVKSKIGSTENLKHQPGGGKVQIVYKPVDLSKVTSK

CGSLGNIHHKPGGGQVEVKSEKLDFKDRVQSKIGSLDNITHVPGGGNKK

IE SEQ ID NO: 22].

(The K12, K18, and K19 constructs shown include an optional methionine start codon.)

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range, but is not intended to designate any value or range of values to only this broader definition. Each value or range of values preceded by the term "about" is also intended to encompass the embodiment of the stated absolute value or range of values.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

The pharmaceutical compositions of the present invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

In various embodiments, the peptide is admixed with a pharmaceutically acceptable carrier to form a pharmaceutical composition that can be systemically administered to the subject orally or via intravenous injection, intramuscular injection, subcutaneous injection, intraperitoneal injection, transdermal injection, intra-arterial injection, intrasternal injection, intrathecal injection, intraventricular injection, intraurethral injection, intracranial injection, intrasynovial injection or via infusions. The pharmaceutical composition preferably contains at least one component that is not found in nature.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain carriers such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

Transdermal administration is a still further option, e.g. by needle-free injection, from a patch such as an iontophoretic patch, or via a transmucosal route, e.g. buccally. The present invention includes compositions and methods for transdermal or topical delivery, to act locally at the point of application, or to act systemically once entering the body's blood circulation. In these systems, delivery may be achieved by techniques such as direct topical application of a substance or drug in the form of an ointment or the like, or by adhesion of a patch with a reservoir or the like that holds the drug (or other substance) and releases it to the skin in a time-controlled fashion. For topical administration, the compositions of the present invention can be in the form of emulsions, lotions, gels, creams, jellies, solutions, suspensions, ointments, and transdermal patches. Some topical delivery compositions may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid. Such topical formaulations may comprise one or more emulsifiers, one or more surfactants, one or more polyglycols, one or more lecithins, one or more fatty acid esters, or one or more transdermal penetration enhancers. Preparations can include sterile aqueous or nonaqueous solutions, suspensions and emulsions, which can be isotonic with the blood of the subject in certain embodiments. Examples of non-aqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like.

For example, in one aspect, sterile injectable solutions can be prepared by incorporating a peptide in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind known in the art. Injectable formulations are in accordance with the invention. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)).

Additionally, the peptides of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the peptides of the disclosure can be formulated as inclusion complexes, such as cyclodextrin inclusion complexes, or liposomes.

The peptide of the present invention can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops. The pressurized container, pump, spray, atomizer, or nebulizer generally contains a solution or suspension of a peptide of the invention comprising, for example, a suitable agent for dispersing, solubilizing, or extending release of the active, a propellant (s) as solvent. Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying. Capsules, blisters and cartridges for use in an inhaler or insufflator may be formulated to contain a powder mix of the peptide of the invention, a suitable powder base and a performance modifier. Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release. Modified release formulations include delayed-, sustained-, pulsed-, controlled-, targeted and programmed release. In the case of dry powder inhalers and aerosols, the dosage unit is determined by means of a valve which delivers a metered amount. Units in accordance with the invention are typically arranged to administer a metered dose or "puff" of a peptide of the invention. The overall daily dose will typically be administered in a single dose or, more usually, as divided doses throughout the day.

A person skilled in the art may recognize that a target cell may require a specific promoter including but not limited to a promoter that is species specific, inducible, tissue-specific, or cell cycle-specific Parr et al, Nat. Med. 3:1145-9 (1997); the contents of which are herein incorporated by reference in its entirety).

Delivery of peptides or compositions of this invention to the CNS may, in some embodiments of this invention, be by systemic administration, injection into CSF pathways, or direct injection into the brain, and in some embodiments, the compositions of this invention are formulated for any of these routes. In one embodiment, the compositions of the present invention are administered by systemic or direct administration into the CNS for targeted action in the CNS, and in some embodiments, the compositions of this invention are formulated for any of these routes. In one embodiment, the composition as set forth herein is formulated for brain-specific delivery, and in some embodiments, the compositions of this invention are formulated for any of these routes. In one embodiment, strategies for drug delivery to the brain include osmotic and chemical opening of the blood-brain barrier (BBB), as well as the use of transport or carrier systems, enzymes, and receptors that control the penetration of molecules in the blood-brain barrier endothelium, and in some embodiments, the compositions of this invention are formulated for any of these routes. In another embodiment, receptor-mediated transcytosis can transport peptides and proteins across the BBB, and in some embodiments, the compositions of this invention are formulated for any of these routes. In other embodiments, strategies for drug delivery to the brain involve bypassing the BBB, and in some embodiments, the compositions of this invention are formulated for any of these routes. In some embodiments, various pharmacological agents are used to open the BBB, and in some embodiments, the compositions of this invention are formulated for any of these routes. In one embodiment, the route of administration may be directed to an organ or system that is affected by neurodegenerative conditions. For example, compounds may be administered topically. In another embodiment, the route of administration may be directed to a different organ or system than the one that is affected by neurodegenerative conditions. For example, compounds may be administered parenterally to treat neurodegenerative conditions. Thus, the present invention provides for the use of various dosage forms suitable for administration using any of the routes listed herein, and any routes which avail the CNS of such materials, as will be appreciated by one skilled in the art.

In some embodiments, the compositions/agents of the invention are specifically formulated such that they cross the blood-brain barrier (BBB). One example of such formulation comprises the use of specialized liposomes, which may be manufactured, for example as described U.S. Pat. Nos. 4,522,811; 5,374,548; and 5,399,331. In some embodiments, the liposomes comprise one or more moieties which are selectively transported into specific cells or organs ("targeting moieties" or "targeting groups" or "transporting vectors"), thus providing targeted drug delivery (see, e.g., V. V. Ranade J. Clin. Phamacol. 29, 685 (1989) fully incorporated by reference herein). In some embodiments the agents are linked to targeting groups that facilitate penetration of the blood brain barrier. In some embodiments, to facilitate transport of agents of the invention across the BBB, they may be coupled to a BBB transport vector (see, for example, Bickel et ah, Adv. Drug Delivery Reviews 46, 247-79 (2001) folly incorporated by reference herein). In some embodiments, transport vectors include cationized albumin or the 0X26 monoclonal antibody to the transferrin receptor; which undergo absorptive-mediated and receptor-mediated transcytosis through the BBB, respectively. Natural cell metabolites that may be used as targeting groups include, inter alia, putrescine, spermidine, spermine, or DHA. Other exemplary targeting moieties include folate or biotin (see, e.g., U.S. Pat. No. 5,416,016 fully incorporated by reference herein); mannosides (Umezawa et ah, Biochem. Biophys. Res. Commun. 153, 1038 (1988) fully incorporated by reference, herein); antibodies (P. G. Bloeman et al, FEBS Lett. 357, 140 (1995); M. Owais et al, Antimicrob. Agents Chemother. 39, 180 (1995)); surfactant protein A receptor (Briscoe et al., Am. J. Physiol. 1233, 134 (1995 fully incorporated by reference herein)); gpl20. (Schreier et al., J. Biol. Chem. 269, 9090 (1994)); see also, K. Keinanen and M. L. Laukkanen, FEBS Lett. 346, 123 (1994); J J. Killion and I J. Fidler, Immunomethods 4, 273 (1994) all of which are fully incorporated by reference herein).

In some embodiments, BBB transport vectors that target receptor-mediated transport systems into the brain comprise factors such as insulin, insulin-like growth factors ("IGF-I," and "IGF-II"), angiotensin II, atrial and brain natriuretic peptide ("ANP," and "BNP"), interleukin I ("IL-I") and transferrin. Monoclonal antibodies to the receptors that bind these factors may also be used as BBB transport vectors. BBB transport vectors targeting mechanisms for absorptive-mediated transcytosis include cationic moieties such as cationized LDL, albumin or horseradish peroxidase coupled with polylysine, cationized albumin or cationized immunoglobulins. Small basic oligopeptides such as the dynorphin analogue E-2078 and the ACTH analogue ebiratide may also cross the brain via absorptive-mediated transcytosis and are potential transport vectors. Other BBB transport vectors target systems for transporting nutrients into the brain. Examples of such BBB transport vectors include hexose moieties, e.g., glucose and monocarboxylic acids, e.g., lactic acid and neutral amino acids, e.g., phenylalanine and amines, e.g., choline and basic amino acids, e.g., arginine, nucleosides, e.g., adenosine and purine bases, e.g., adenine, and thyroid hormone, e.g., triiodothyridine. Antibodies to the extracellular domain of nutrient transporters may also be used as transport vectors. Other possible vectors include angiotensin II and ANP, which may be involved in regulating BBB permeability.

In some cases, the bond linking the therapeutic agent to the transport vector may be cleaved following transport into the brain in order to liberate the biologically active agent. Exemplary linkers include disulfide bonds, ester-based linkages, thioether linkages, amide bonds, acid-labile linkages, and Schiff base linkages. Avidin/biotin linkers, in which avidin is covalently coupled to the BBB drug transport vector, may also be used. Avidin itself may be a drug transport vector. Transcytosis, including receptor-mediated transport of compositions across the blood brain barrier, may also be suitable for the agents of the invention. Transferrin receptor-mediated delivery is disclosed in U.S. Pat. Nos. 5,672,683; 5,383,988; 5,527,527; 5,977,307; and 6,015,555, all of which are fully incorporated herein by reference. Transferrin-mediated transport is also known. P. M. Friden et al, Pharmacol. Exp. Ther. 278, 1491-98 (1996); H J. Lee, J. Pharmacol. Exp. Titer. 292, 1048-52 (2000) all of which are fully incorporated herein by reference. EGF receptor-mediated delivery is disclosed in Y. Deguchi et ah, Bioconjug. Chem. 10, 32-37 (1999), and transcytosis is described in A. Cerletti et al, J. Drug Target. 8, 435-46 (2000) all of which are fully incorporated herein by reference. Insulin fragments have also been used as carriers for delivery across the blood brain barrier. M. Fukuta et al, Pharm. Res. 11. 1681-88 (1994). Delivery of agents via a conjugate of neutral avidin and cationized human albumin has also been described. Y. S. Kang et al, Pharm. Res. 1, 1257-64 (1994) all of which are fully incorporated herein by reference. Other modifications in order to enhance penetration of the agents of the invention across the blood brain barrier may be accomplished using methods and derivatives known in the art. For example, U.S. Pat. No. 6,024,977 discloses covalent polar lipid conjugates for targeting to brain and central nervous system. U.S. Pat. No. 5,017,566 discloses cyclodextrin derivatives comprising inclusion complexes of lipoidal forms of dihydropyridine redox targeting moieties. U.S. Pat. No. 5,023,252 discloses the use of pharmaceutical compositions comprising a neurologically active drug and a compound for facilitating transport of the drug across the blood-brain barrier including a macrocyclic ester, diester, amide, diamide, amidine, diamidine, thioester, dithioester, thioamide, ketone or lactone. U.S. Pat. No. 5,024,998 discloses parenteral solutions of aqueous-insoluble drugs with cyclodextrin derivatives. U.S. Pat. No. 5,039,794 discloses the use of a metastatic tumor-derived egress factor for facilitating the transport of compounds across the blood-brain barrier. U.S. Pat. No. 5,112,863 discloses the use of N-acyl amino acid derivatives as antipsychotic drugs for delivery across the blood-brain barrier. U.S. Pat. No. 5,124, 146 discloses a method for delivery of therapeutic agents across the blood-brain barrier at sites of increase permeability associated with brain lesions. U.S. Pat. No. 5,153,179 discloses acylated glycerol and derivatives for use in a medicament for improved penetration of cell membranes. U.S. Pat. No. 5,177,064 discloses the use of lipoidal phosphonate derivatives of nucleoside antiviral agents for delivery across the blood-brain barrier. U.S. Pat. No. 5,254,342 discloses receptor-mediated transcytosis of the blood-brain barrier using the transferrin receptor in combination with pharmaceutical compounds that enhance or accelerate this process. U.S. Pat. No. 5,258,402 discloses treatment of epilepsy with imidate derivatives of anticonvulsive sulfamate. U.S. Pat. No. 5,270,312 discloses substituted piperazines as central nervous system agents. U.S. Pat. No. 5,284,876 discloses fatty acid conjugates of dopamine drugs. U.S. Pat. No. 5,389,623 discloses the use of lipid dihydropyridine derivatives of anti-inflammatory steroids or steroid sex hormones for delivery across the blood-brain barrier. U.S. Pat. No. 5,405,834 discloses prodrug derivatives of thyrotropin releasing hormone. U.S. Pat. No. 5,413, 996 discloses acyloxyalkyl phosphonate conjugates of neurologically-active drugs for anionic sequestration of such drugs in brain tissue. U.S. Pat. No. 5,434,137 discloses methods for the selective opening of abnormal brain tissue capillaries using bradykinin infused into the carotid artery. U.S. Pat. No. 5,442,043 discloses a peptide conjugate between a peptide having a biological activity and incapable of crossing the blood-brain barrier and a peptide which exhibits no biological activity and is capable of passing the blood-brain barrier by receptor-mediated endocytosis. U.S. Pat. No. 5,466,683 discloses water soluble analogues of an anticonvulsant for the treatment of epilepsy. U.S. Pat. No. 5,525,727 discloses compositions for differential uptake and retention in brain tissue comprising a conjugate of a narcotic analgesic and agonists and antagonists thereof with a lipid form of dihydropyridine that forms a redox salt upon uptake across the blood-brain barrier that prevents partitioning back to the systemic circulation all of which are fully incorporated herein by reference.

Nitric oxide is a vasodilator of the peripheral vasculature in normal tissue of the body. Increasing generation of nitric oxide by nitric oxide synthase causes vasodilation without loss of blood pressure. The blood-pressure-independent increase in blood flow through brain tissue increases cerebral bioavailability of blood-born compositions. This increase in nitric oxide may be stimulated by administering L-arginine. As nitric oxide is increased, cerebral blood flow is consequently increased, and drugs in the blood stream are carried along with the increased flow into brain tissue. Therefore, L-arginine may be used in the pharmaceutical compositions of the invention to enhance delivery of agents to brain tissue after introducing a pharmaceutical composition into the blood stream of the subject substantially contemporaneously with a blood flow enhancing amount of L-arginine, as described in WO 00/56328.

Still further examples of modifications that enhance penetration of the blood brain barrier are described in International (PCT) Application Publication Number WO 85/02342, which discloses a drug composition comprising a glycerolipid or derivative thereof. PCT Publication Number WO 089/11299 discloses a chemical conjugate of an antibody with an enzyme which is delivered specifically to a brain lesion site for activating a separately-administered neurologically-active prodrug. PCT Publication Number WO 91/04014 discloses methods for delivering therapeutic and diagnostic agents across the blood-brain barrier by encapsulating the drugs in liposomes targeted to brain tissue using transport-specific receptor ligands or antibodies. PCT Publication Number WO 91/04745 discloses transport across the blood-brain barrier using cell adhesion molecules and fragments thereof to increase the permeability of tight junctions in vascular endothelium. PCT Publication Number WO 91/14438 discloses the use of a modified, chimeric monoclonal antibody for facilitating transport of substances across the blood-brain barrier. PCT Publication Number WO 94/01131 discloses lipidized proteins, including antibodies. PCT Publication Number WO 94/03424 discloses the use of amino acid derivatives as drug conjugates for facilitating transport across the blood-brain barrier. PCT Publication Number WO 94/06450 discloses conjugates of neurologically-active drugs with a dihydropyridine-type redox targeting moiety and comprising an amino acid linkage and an aliphatic residue. PCT Publication Number WO 94/02178 discloses antibody-targeted liposomes for delivery across the blood-brain barrier. PCT Publication Number WO 95/07092 discloses the use of drug-growth factor conjugates for delivering drugs across the blood-brain barrier. PCT Publication Number WO 96/00537 discloses polymeric microspheres as injectable drug-delivery vehicles for delivering bioactive agents to sites within the central nervous system. PCT Publication Number WO 96/04001 discloses omega-3-fatty acid conjugates of neurologically-active drugs for brain tissue delivery. PCT Publication Number WO 96/22303 discloses fatty acid and glycerolipid conjugates of neurologically-active drugs for brain tissue delivery. In one embodiment, the active compound can be delivered in a vesicle, for example, a liposome. In another embodiment, the active compound can be delivered as a nanoparticle. In one embodiment, delivery may be specifically targeted to the CNS. In another embodiment, the active compounds may be delivered by any method described herein. The compositions of this invention may comprise ingredients known to the skilled artisan to be useful in formulating compositions for administration to a subject. In some embodiments, the compositions will comprise pharmaceutically acceptable carriers or diluents, n some embodiments, the phrase "pharmaceutically acceptable carriers or diluents" may comprise a solid carrier or diluent for solid formulations, a liquid carrier or diluent for liquid formulations, or mixtures thereof.

In some embodiments, the compositions/agents of the invention comprise a "piggyback mechanism" to deliver specific desirable agents, or combinations thereof to the CNS, i.e. to ensure that they cross the blood-brain barrier (BBB).

In one embodiment, technologies modifications that enhance penetration of the blood brain barrier are described in WO2009117041 [use of pyrene to carry peptides across the blood brain barrier], US20060182684 [Method for transporting a compound across the blood-brain barrier], U.S. Pat. No. 6,258,780 [Method and composition for enabling passage through the blood-brain-barrier], or US20060293242 [Transporting of taxoid derivatives through the blood brain barrier].

In some embodiments, the compositions/agents of the invention are administered by intraperitoneal injection or by intracerebro ventricular injection.

The pharmaceutical compositions of viral vectors described herein may be characterized by one or more of bioavailability, therapeutic window and/or volume of distribution.

In some embodiments, peptide-related nucleotides and/or peptide-related nucleotide compositions of the present invention may be combined with, coated onto or embedded in a device. Devices may include, but are not limited to stents, pumps, and/or other implantable therapeutic device. Additionally, peptide-related nucleotides and/or peptide-related nucleotide compositions may be delivered to a subject while the subject is using a compression device such as, but not limited to, a compression device to reduce the chances of deep vein thrombosis (DVT) in a subject. The present invention provides for devices which may incorporate viral vectors that encode one or more peptide-related polynucleotide payload molecules. These devices contain in a stable formulation the viral vectors which may be immediately delivered to a subject in need thereof, such as a human patient.

Devices for administration may be employed to deliver the viral vectors comprising an peptide-related nucleotides of the present invention according to single, multi- or split-dosing regimens taught herein.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

In some embodiments, peptide-related nucleotides and/or peptide-related polynucleotide compositions of the present invention may be delivered using a device such as, but not limited to, a stent, a tube, a catheter, a pipe, a straw, needle and/or a duct. Methods of using these devices are described herein and are known in the art.

In one embodiment, the peptide-related polynucleotides of the present invention may be administered to a subject using delivery systems which integrate image guided therapy and integrate imaging such as, but not limited to, laser, MRgFUS, endoscopic and robotic surgery devices.

In one embodiment, the peptide-related polynucleotides of the present invention may be administered to a subject using the CLEARPOINT® neuro intervention system by MRI Interventions, Inc. The CLEARPOINT® neuro intervention system may be used alone or in combination with any of the other administration methods and devices described herein. The CLEARPOINT® neuro intervention system helps to provide stereotactic guidance in the placement and operation of instruments or devices during the planning and operation of neurological procedures.

In one embodiment, the peptide-related polynucleotides of the present invention may be administered to a subject using the NEUROMATE® stereotactic robot system by Renishaw PLC. The NEUROMATE® system may be used alone or in combination with any of the other administration methods and devices described herein. As a non-limiting example, the NEUROMATE® system may be used with head holders, CT image localizers, frame attachments, remote controls and software. [000146] In one embodiment, the peptide-related polynucleotides of the present invention may be administered to a subject using the Elekta MICRODRIVE™ device by Elekta AB. The MICRODRIVE™ device may be used alone or in combination with any of the other administration methods and devices described herein. As a non-limiting example, the MICRODRIVE™ device may be used to position electrodes (e.g., for micro electrode recording (MER), macro stimulation and deep brain stimulation (DBS) electrode implantation), implantation of catheters, tubes or DBS electrodes using cross-hair and A-P holders to verify position, biopsies, injections and aspirations, brain lesioning, endoscope guidance and GAMMA KNIFE® radiosurgery.

In one embodiment, the peptide-related polynucleotides of the present invention may be administered to a subject using the AXIIIS® stereotactic miniframe by MONTERIS® Medical, Inc. The AXIIIS® stereotactic miniframe may be used alone or in combination with any of the other administration methods and devices described herein. The AXIIIS® stereotactic miniframe is a trajectory alignment device which may be used for laser coagulation, biopsies, catheter placement, electrode implant, endoscopy, and clot evacuation. The miniframe allows for 360 degree interface and provides access to multiple intracranial targets with a simple adjustment. Further, the miniframe is compatible with MRI.

In one embodiment, the peptide-related polynucleotides of the present invention may be administered to a subject using the INTEGRA™ CRW® system by Integra Life-Sciences Corporation. The INTEGRA™ CRW® system may be used alone or in combination with any of the other administration methods and devices described herein. The CRW® system may be used for various applications such as, but not limited to, stereotactic surgery, microsurgery, catheterization and biopsy. The CRW® system is designed to provide accuracy to those who use the system (e.g., thumb lock screws, Vernier scaling, double bolt fixation, and a solid frame).

In one embodiment, the peptide-related polynucleotides of the present invention may be administered to a subject using the EPOCH® solution system by Stereotaxis, Inc. which may include the NIOBE® ES magnetic navigation system, the VDRIVE® robotic navigation system and/or the ODYSSEY® information solution (all by Stereotaxis, Inc.). The EPOCH® solution system may be used alone or in combination with any of the other administration methods and devices described herein. As a non-limiting example, the NIOBE® ES magnetic navigation system may be used to accurately contact a subject. As another non-limiting example the NIOBE® ES magnetic system may be used with the VDRIVE® robotic navigation system to provide precise movement and stability.

In one embodiment, the peptide-related polynucleotides of the present invention may be administered to a subject using a Neuro Station workstation which uses frameless stereotactic methods to provide image-guidance for applications such as, but not limited to, surgical planning, biopsies, craniotomies, endoscopy, intra-operative ultrasound and radiation therapy.

In one embodiment, the peptide-related polynucleotides of the present invention may be administered to a subject using a robotic stereotaxis system such as, but not limited to the device described in U.S. Pat. No. 5,078,140, the contents of which are herein incorporated by reference in its entirety. The robotic arm of the device may be used to precisely orient the surgical tools or other implements used to conduct a procedure.

In one embodiment, the peptide-related polynucleotides of the present invention may be administered to a subject using an automatic delivery system such as, but not limited to the device described in U.S. Pat. No. 5,865,744, the contents of which are herein incorporated by reference in its entirety. Based on the images gathered by the delivery system, the computer adjusts the administration of the needle to be the appropriate depth for the particular subject.

Pharmaceutical compositions intended for transdermal use may be prepared according to any method known to the art for the manufacture of pharmaceutical compositions.

According to one aspect, the compounds of the invention are for use in medicine, particularly human medicine. The peptides are effective to treat tau protein aggregation related diseases.

The present invention also includes methods of treating tau protein aggregation related diseases comprising administering an effective amount of a peptide or a variant thereof to a subject in need of treatment.

The disclosure also provides fibrillation-inhibitory peptides. For example, fibrillation-inhibitory peptides associated with tau fibrillation include those of PEPTIDE ID NO: 1-176, 184-190, and 193-475. Each of these peptides binds to the tau fibrils, generally at the steric zipper region, which comprises the amino acid residues VQIVYK (PEPTIDE ID NO: 191; SEQ ID NO: 2). Each of these peptides binds to the tau fibrils, generally at the steric zipper region, which comprises the amino acid residues VQIINK (PEPTIDE ID NO: 192; SEQ ID NO: 1). The inhibitory peptides include a zipper-inhibitory feature comprising side chains that project out from the inhibitory peptide sequence backbone in such a way as to interfere with binding of subsequent zipper sequences to the nascent fibril.

Tau proteins are characterised as one family among a larger number of protein families which co-purify with microtubules during repeated cycles of assembly and disassembly (Shelanski et al. (1973) Proc. Natl. Acad. Sci. USA, 70, 765-768), and known as microtubule-associated-proteins (MAPs). The tau family in addition is characterised by the presence of a characteristic N-terminal segment which is shared by all members of the family, sequences of ~50 amino acids inserted in the N-terminal segment, which are developmentally regulated in the brain, a characteristic tandem repeat region consisting of 3 or 4 tandem repeats of 31-32 amino acids, and a C-terminal tail.

Tau oligomer includes an aggregate of tau protein subunits. The minimal size of a tau oligomer is two subunits, and the maximal size of a tau oligomer referred to in this application is 12 tau subunits. These tau oligomers are tau dimer, tau trimer, tau tetramer, tau pentamer, tau hexamer, tau septamer, tau octamer, tau nonamer, tau decamer, tau unadecamer, tau dodecamer. In some embodiments, the subunits may be composed of any 3R or 4R tau.

The tau oligomer can be substantially purified and/or isolated. In some embodiments, tau protein can be purified by cation exchange using SP Sepharose, heat denaturation in Laemmli sample buffer 5 min at 95° C., and fraction collection from continuous SDS-PAGE. Tau oligomers can be formed by incubation of tau subunits in buffer (50 mM Tris pH 7.4) at 37° C. The size range of the oligomers may be controlled by modulation of tau concentration, length of incubation, buffer composition, and/or choice of tau isoforms, fragment or peptide and/or mixtures thereof.

The tau oligomer subunits may or may not be linked by disulfide bonds. In some embodiments, the tau oligomer can be stabilized by disulfide bonds and is stable for at least two months in a non-reductive environment.

Tau filaments bind the dye thioflavine S (ThS) and yield fluorescent signal and have a cross-beta diffraction pattern (Berriman et al., 2003; Friedhoff et al., 1998). The association of tau with several diseases including Alzheimer's disease and senile dementia makes it an important target for disrupting fibrillation. Tau contains four microtubule-binding regions, which have been implicated in the assembly of tau filaments. These repeat domains are found in the core of PHFs from multiple tau isoforms and can assemble into PHF-like fibrils in isolation (Kondo et al., 1988; Wille et al., 1992; Wischik et al., 1988). The fibrillation of tau depends on the formation of β sheets by the short segment VQIVYK (PEPTIDE ID NO: 191; SEQ ID NO: 2) from the third repeat and that this segment in isolation forms amyloid-like fibrils. Consequently, this segment of tau involved in the fibril spine can be used as a target for disrupting tau fibrillation. Because full-length tau isoforms are about 400 amino acids long, several smaller constructs with similar properties have been created for experimental convenience.

One of these constructs, termed K12, contains three tau microtubule-binding repeats and its sequence contains residues Q244-Y394 with a starting Met residue, without the second microtubule-binding repeat V275-S305 (Schweers et al., 1995; Wille et al., 1992). This 13 kDa derivative of tau contains the VQIVYK (PEPTIDE ID NO: 191; SEQ ID NO: 2) segment and forms PHFs in vitro (Schweers et al., 1995; Wille et al., 1992).

The structures of several short segments from proteins that form amyloid and amyloid-like fibrils have been determined. These segment structures, including VQIVYK (PEPTIDE ID NO: 191; SEQ ID NO: 2) from tau, reveal the molecular basis for the common features observed in amyloid-like fibrils. The main common structural feature of all these segments, termed a steric zipper, contains a pair of β-sheets, in which the amino acid side chains from one β-sheet interdigitate with its neighboring β-sheet across an interface that excludes all solvent. These segment structures contain molecular features that are important for the fibrillation of its parent protein, and disrupting packing of the segment structure can be applicable to disrupting the fibrillation of the full-length protein. The methods disclosed herein provide an approach to designing D-amino acid fibril-capping peptides, which involves creating a novel interface between the inhibitor molecule and a steric zipper segment structure. Starting with the atomic-level structure of the VQIVYK (PEPTIDE ID NO: 191; SEQ ID NO: 2) segment from tau, a D-amino acid fibril blocker is designed which interacts favorably with its fibril-like scaffold, but also projects side chains away from the scaffold to prevent the addition of molecules to the fibril spine. ThS fluorescence assays and electron microscopy can be used to demonstrate that these D-amino acid peptides inhibit fibril formation. This structure-based approach can be used to design inhibitors of amyloid fibrils formed by other proteins if the structure of fibril-forming segments is known or can be accurately predicted.

The inhibitory peptides of the invention may be used in methods of treating fibrillation-associated diseases. The invention provides pharmaceutical compositions useful for treating fibrillation-associated diseases. The pharmaceutical composition comprises a fibrillation-inhibitory peptide and a pharmaceutically acceptable excipient. Suitable excipients for use with these compositions can assist the inhibitory peptide in crossing physiological barriers, such as the blood-brain barrier.

Such peptides are useful to treat, prevent, or ameliorate neurodegenerative diseases, including tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau in an animal.

The term "tauopathy" encompasses all neurological diseases that are accompanied by the appearance of abnormal forms of microtubule associated protein tau in the brains of patients, such as in which accumulation of phosphorylated tau occurs in neuronal cells and glia cells, and involves the pathological aggregation of tau within the brain. The term includes, but is not limited to, the following diseases: Alzheimer's disease, Gerstmann-Straussier-Scheinker disease, British dementia, Danish dementia, Pick's disease, Progressive supranuclear palsy, Corticobasal degeneration, Argyrophilic grain disease, Guam Parkinsonism-dementia complex, Tangle-only dementia, White matter tauopathy with globular glial inclusions, Frontotemporal dementia (e.g., FTDP-17), and Parkinsonism linked to chromosome 17.

In addition to familial and sporadic AD, other exemplary tauopathies are frontotemporal dementia with parkinsonism linked to chromosome 17 (FTDP-17), progressive subcortical gliosis, tangle only dementia, diffuse neurofibrillary tangles with calcification, amyotrophic lateral sclerosis parkinsonism-dementia complex, Down syndrome, Hallervorden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy, such as dementia pugulistica (boxing disease). (Morris, et al. Neuron 70:410-26, 2011).

Prevention of tauopathies means preventing occurrence of a tauopathy. Therapy of tauopathies means preventing or improving/reducing progress of tauopathy disorder.

A tauopathy-related behavioral phenotype includes cognitive impairments, early personality change and disinhibition, apathy, abulia, mutism, apraxia, perseveration, stereotyped movements ehaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and Aβ42 levels. Elevated tau and decreased Aβ42 levels signify the presence of AD. Individuals suffering from AD can also be diagnosed by AD and Related Disorders Association criteria.

In some embodiments, the method generally includes administering to a subject having or at risk of having a tauopathic condition an amount of a pharmaceutical composition as described herein effective to inhibit to any of degree caspase-2 tau cleavage. In other embodiments, the method generally includes administering to a subject having or at risk of having a tauopathic condition an amount of a pharmaceutical composition as described herein effective to ameliorate at least one clinical sign or symptom characteristic of the tauopathic condition. In other embodiments, the method generally includes administering to a subject having or at risk of having a tauopathic condition an amount of a pharmaceutical composition as described herein effective to protect the subject against development of a tauopathic condition.

As used herein. "at risk" refers to a subject that may or may not actually possess the described risk. Thus, for example, a subject "at risk" for developing a tauopathic condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of tauopathic conditions can include, for example, mutations in certain genes (e.g., APP, PSEN1, PSEN2, CHMP2B, FUS, GRN, MAPT, TARDBP, VCP, and/or the APOE4 variant of APOE) and/or a family history of Alzheimer's disease or frontotemporal dementia. As used herein, "protect" refers to any delay in the onset of at least one symptom or clinical sign characteristic of a particular condition, or any reduction in the extent, severity, frequency, and/or likelihood of the onset of at least one symptom or clinical sign characteristic of a particular condition.

"Amyloidosis," as used herein, encompasses a variety of conditions in which amyloid proteins are abnormally deposited in organs and/or tissues. A protein is described as being amyloid if, due for example to an alteration in its secondary structure, it takes on an aggregated insoluble form similar to the beta-pleated sheet. Examples of conditions involving amyloidosis include, for example, Alzheimer's disease.

"Polypeptide aggregation-associated condition," as used herein, means conditions characterized by the aggregation of polypeptides of a kind, or to a degree, that is not commonly observed in healthy subjects. Examples of such conditions include, for example, Alzheimer's disease.

The phrases "concurrent administration," "co-administration," "simultaneous administration," and "administered simultaneously" mean that the compounds are administered in combination.

The present invention includes the use of a combination of a compound as provided in PEPTIDE ID NO: 1-176, 184-190, and 193-475, and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of PEPTIDE ID NO: 1-176, 184-190, and 193-475 or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) amyloid-β (or fragments thereof), such as $A\beta_{1-5}$ conjugated to pan HLA DR-binding epitope (PADRE®), ACC-001 (Elan/Wyeth), and Affitope;

(ii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos. WO04/032868, WO05/025616, WO06/036291, WO06/069081, WO06/1 18959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAI D®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORI L®), sulindac sulfide, diflunisal (DOLOBID®), naproxen (NAPROSYN®), naproxen sodium (ANAPROX®, ALEVE®), insulin-degrading enzyme (also known as insulysin), the gingko *biloba* extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LI PITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(iv) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(v) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(vi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(vii) monoamine oxidase (MAO) inhibitors, such as selegiline (EMSAM), selegiline hydrochloride (1-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(viii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/01 1 1372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(ix) serotonin (5-hydroxytryptamine) 1 A (5-HT-IA) receptor antagonists, such as spiperone, /evo-pindolol, lecozotan;

(x) serotonin (5-hydroxytryptamine) 2C (5-HT$_2$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xi) serotonin (5-hydroxytryptamine) 3C (5-HTk) receptor antagonists, such as Ondansetron (Zofran);

(xii) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xiii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xiv) Glycine transporter-1 inhibitors such as paliflutine, ORG-25935, and ORG-26041; and mGluR modulators such as AFQ-059 and amantidine;

(xv) AMPA-type glutamate receptor modulators such as perampanel, mibampator, selurampanel, GSK-729327, and N-{(3 S,4S)-4-[4-(5-cyanothiophen-2-yl)phenoxy]tetrahydrofur-3-yl}propane-2-sulfonamide;

(xvi) P450 inhibitors, such as ritonavir;

(xvii) tau therapy targets, such as davunetide; and (xviii) BACE inhibitors; and the like.

Examples of AD therapeutic agents include, but are not limited to, the BACE-1 inhibitors described herein, BACE-1 inhibitors CTS-21 166 (CoMentis Inc.), AZD3293 (AstraZeneca), E-2609 (Eisai), TAK-070 (Takeda), and HPP-854 (Transtech), gamma secretase inhibitors (e.g., as described in WO2007/084595 and WO2009/008980), gamma secretase modulators (as described e.g., in WO2008/153793 and WO2010/056849), solanezumab (Eli Lilly), liraglutide (Lancaster University), bexarotene (brand name TARGRETIN®), ACC-001 (vaccine), muscarinic antagonists (e.g., mi agonists (such as acetylcholine, oxotremorine, carbachol, or McNa343), or m$_2$ antagonists (such as atropine, dicycloverine, tolterodine, oxybutynin, ipratropium, methoctramine, tripitamine, or gallamine); cholinesterase inhibitors (e.g., acetyl- and/or butyrylchlolinesterase inhibitors such as donepezil (ARICEPT®), galantamine (RAZADYNE®), and rivastigimine (EXELON®); N-methyl-D-aspartate receptor antagonists (e.g., NAMENDA® (memantine HC1, available from Forrest Pharmaceuticals, Inc.); combinations of cholinesterase inhibitors and N-methyl-D-aspartate receptor antagonists; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., REMBER®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin VYTORIN®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., SIMCOR® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inliibitors; agents that can induce Abeta efflux such as gelsolin; Metal-protein attenuating compound (e.g, PBT2); and GPR3 modulators; and antihistamines such as Dimebolin (e.g., DIMEBON®, Pfizer).

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure. Treatment of a subject with a therapeutically effective amount of a peptide, of the invention can include a single treatment or, preferably, can include a series of treatments. In a preferred example, a subject is treated with peptide daily, one time per week or biweekly.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

The dose of the peptide of the present disclosure also will be determined by the existence, nature and extent of any adverse side effects that might accompany the administration of a particular peptide of the present disclosure. Typically, the attending physician will decide the dosage of the peptide of the present disclosure with which to treat each individual patient, taking into consideration a variety of factors, such as age, body weight, general health, diet, sex, peptide of the present disclosure to be administered, route of administration, and the severity of the condition being treated. By way of example and not intending to limit the invention, the dose of the peptide of the present disclosure can be about 0.0001 to about 100 mg/kg body weight of the subject being treated/day. The peptide can be administered in one or more doses, such as from 1 to 3 doses.

In some embodiments, the pharmaceutical composition comprises any of the analogs disclosed herein at a purity level suitable for administration to a patient. In some embodiments, the analog has a purity level of at least about 90%, preferably above about 95%, more preferably above about 99%, and a pharmaceutically acceptable diluent, carrier or excipient.

The pharmaceutical compositions may be formulated to achieve a physiologically compatible pH. In some embodiments, the pH of the pharmaceutical composition may be at least 5, or at least 6, or at least 7, depending on the formulation and route of administration.

In various embodiments, single or multiple administrations of the pharmaceutical compositions are administered depending on the dosage and frequency as required and tolerated by the subject. In any event, the composition should provide a sufficient quantity of at least one of the peptide disclosed herein to effectively treat the subject. The dosage can be administered once but may be applied periodically until either a therapeutic result is achieved or until side effects warrant discontinuation of therapy.

The dosing frequency of the administration of the peptide pharmaceutical composition depends on the nature of the therapy and the particular disease being treated. Treatment of a subject with a therapeutically effective amount of a peptide, of the invention can include a single treatment or, preferably, can include a series of treatments. In a preferred example, a subject is treated with peptide daily, one time per week or biweekly.

In one aspect, the peptides of the present invention can be used to identify agents that reduce or increase a level of tau aggregates in a cell. Methods of identifying such agents can be useful for identifying new therapies for tau aggregate-related diseases. In one aspect, a method includes: measuring the interaction between tau aggregate fibrils and a peptide inhibitor of tau aggregation (referred to as the "probe") to form a pre-formed fibril-probe complex, and utilizing this measurement to determine the ability of a test compound to disrupt the interaction of the said fibril-probe complex; detecting or measuring a level of probe displacement is known as a "competition assay"

In one aspect, the fibril-probe interaction can take place in vitro (with or without cells present), in vivo (e.g., by administration of a test compound to a subject), or ex vivo (e.g., by interacting with a biological sample obtained from a subject with a test compound). Test compounds that bind tau at the same aggregation-driving sites as the probe, cause an increased level of displacement of probe, as compared to said pre-formed fibril-probe complex before said interaction, or as compared to a control pre-formed fibril-probe complex that does not form a complex with the said test compound, and can be identified and/or selected as potential therapeutic agents. Therefore, in some embodiments, the therapy comprises administration of an agent that has been identified as a potential therapeutic agent that binds tau at the same aggregation-driving sites as the probe, using a method described herein.

In one aspect, the competition assay can include monitoring probe-fiber interaction by various means such as fluorescence, fluorescence polarization, time-resolved fluorescence, fluorescence energy transfer (FRET), luminescence, radiolabeling, and the like. In the case of a fluorescence readout, a probe can be a peptide of the covalently linked at its N-terminus to a fluorophore, for example tetramethylrhodamine (TAMRA) (InnoPep, San Diego, Calif.). Preferably a probe selectively binds to tau amyloid aggregates over the monomeric (non-aggregated) form.

In one aspect, the competition assay utilizes probe peptides of the current invention, but other tau aggregation inhibitors can be utilized, such as those described in PCT/US18/36507. In another aspect, the competition assay can be utilized using other protein aggregates such as of transthyretin and amylin, and peptide inhibitors of such protein aggregates. In one aspect, the competition assay utilizes probe peptides found to be p53 aggregation inhibitors, such as those described in PCT/US18/19417.

In one aspect, provided is a method of identifying a compound which binds to tau aggregates and displaces or blocks binding of a probe comprising a peptide of the invention comprising: i. exposing tau aggregates with a probe peptide; and ii. identifying a compound that displaces or blocks binding of said probe peptide.

In one aspect, provided is a method of using a peptide of the invention in screening for candidate compounds which inhibit the activity of the peptide in its interaction with tau aggregates.

The invention having been described, the following examples are offered by way of illustration, and not limitation.

EXAMPLES

The present disclosures provide peptides comprising a variety of sequences.

Example 1

The peptides of the invention are prepared via solid phase synthesis on a suitable resin using t-Boc or Fmoc chemistry or other well-established techniques, (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989; Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000) by a method similar to that described below, unless specified otherwise.

Solid phase synthesis is initiated by attaching an N-terminally protected amino acid with its carboxy terminus to an inert solid support carrying a cleavable linker. This solid support can be any polymer that allows coupling of the initial amino acid, e.g. a Pam resin, trityl resin, a chlorotrityl resin, a Wang resin or a Rink resin in which the linkage of the carboxy group (or carboxamide for Rink resin) to the resin is sensitive to acid (when Fmoc strategy is used). The polymer support is stable under the conditions used to deprotect the α-amino group during the peptide synthesis. After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyl-uronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc. Usually, reactive side-chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999). In some cases, it might be desirable to have side-chain protecting groups that can selectively be removed while other side-chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side-chain functionalities are protected with acid labile protecting groups, the ivDde ([1-(4,4-dimethyl-2,6-dioxocyclohex-1-ylidene)-3-methylbutyl) group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids. Finally, the peptide is cleaved from the resin. This can be achieved by using HF or King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Those peptides, analogs or derivatives of the invention which include non-natural amino acids and/or a covalently attached N-terminal mono- or dipeptide mimetic may be produced as described in the experimental part. Or see e.g., Hodgson et al: "The synthesis of peptides and proteins containing non-natural amino acids", and Chemical Society Reviews, vol. 33, no. 7 (2004), p. 422-430.

The peptides are prepared according to the below-mentioned peptide synthesis and the peptides presented in the Tables 1-2 can be prepared similar to the below-mentioned synthesis, unless specified otherwise.

One method of peptide synthesis is by Fmoc chemistry on a microwave-based Liberty peptide synthesizer (CEM Corp., North Carolina). The resin is Tentagel S RAM with a loading of about 0.25 mmol/g or PAL-ChemMatrix with a loading of about 0.43 mmol/g or PAL AM matrix with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are 5 minutes at up to 70° C. Deprotection is with 10% piperidine in NMP at up to 70° C. The protected amino acids used are standard Fmoc-amino acids (supplied from e.g. Anaspec or Novabiochem or Protein Technologies).

Another method of peptide synthesis is by Fmoc chemistry on a Prelude peptide synthesizer (Protein Technologies, Arizona). The resin is Tentagel S RAM with a loading of about 0.25 mmol/g or PAL-ChemMatrix with a loading of about 0.43 mmol/g or PAL AM with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are single or double couplings for 1 or 2 hours at room temperature. Deprotection is with 20% piperidine in NMP. The protected amino acids used are standard Fmoc-amino acids (supplied from e.g. Anaspec or Novabiochem or Protein Technologies). The crude peptides are purified such as by semipreparative HPLC on a 20 mm×250 mm column packed with either 5 μm or 7 μm C-18 silica. Peptide solutions are pumped onto the HPLC column and precipitated peptides are dissolved in 5 ml 50% acetic acid $H_2O$ and diluted to 20 ml with $H_2O$ and injected on the column which then is eluted with a gradient of 40-60% $CH_3CN$ in 0.1% TFA 10 ml/min during 50 min at 40° C. The peptide containing fractions are collected. The purified peptide is lyophilized after dilution of the eluate with water.

All peptides with C terminal amides described herein are prepared by a method similar to described below unless specified otherwise. MBHA resin (4-methylbenzhydrylamine polystyrene resin is used during peptide synthesis.

MBHA resin, 100-180 mesh, 1% DVB cross-linked polystyrene; loading of 0.7-1.0 mmol/g), Boc-protected and Fmoc protected amino acids can be purchased from Midwest Biotech. The solid phase peptide syntheses using Boc-protected amino acids are performed on an Applied Biosystem 430A Peptide Synthesizer. Fmoc protected amino acid synthesis is performed using the Applied Biosystems Model 433 Peptide Synthesizer.

Synthesis of the peptides is performed on the Applied Biosystem Model 430A Peptide Synthesizer. Synthetic peptides are constructed by sequential addition of amino acids to a cartridge containing 2 mmol of Boc protected amino acid. Specifically, the synthesis is carried out using Boc DEPBT-activated single couplings. At the end of the coupling step, the peptidyl-resin is treated with TFA to remove the N-terminal Boc protecting group. It is washed repeatedly with DMF and this repetitive cycle is repeated for the desired number of coupling steps. After the assembly, the sidechain protection, Fmoc, is removed by 20% piperidine treatment and acylation was conducted using DIC. The peptidyl-resin at the end of the entire synthesis is dried by using DCM, and the peptide is cleaved from the resin with anhydrous HF. The peptidyl-resin is treated with anhydrous HF, and this typically yielded approximately 350 mg (~50% yield) of a crude deprotected-peptide. Specifically, the peptidyl-resin (30 mg to 200 mg) is placed in the hydrogen fluoride (HF) reaction vessel for cleavage. 500 µL of p-cresol was added to the vessel as a carbonium ion scavenger. The vessel is attached to the HF system and submerged in the methanol/dry ice mixture. The vessel is evacuated with a vacuum pump and 10 ml of HF is distilled to the reaction vessel. This reaction mixture of the peptidyl-resin and the HF is stirred for one hour at 0° C., after which a vacuum is established and the HF is quickly evacuated (10-15 min). The vessel is removed carefully and filled with approximately 35 ml of ether to precipitate the peptide and to extract the p-cresol and small molecule organic protecting groups resulting from HF treatment. This mixture is filtered utilizing a teflon filter and repeated twice to remove all excess cresol. This filtrate is discarded. The precipitated peptide dissolves in approximately 20 ml of 10% acetic acid (aq). This filtrate, which contained the desired peptide, is collected and lyophilized.

Example 2

His-Tau40 WT (SEQ ID NO: 26) Expression

Make 6×950 mL of LB broth by adding 25 g lysogeny broth "LB" powder [Fisher Chemicals, cat #BP9723-5] to flask, then fill to 950 mL with DI water in 2 L plastic Erlenmeyer flasks, and 1×350 mL by adding 8.75 g LB powder to flask, then fill to 350 mL with DI water in 1 L glass flask. Autoclave to sterilize. Inoculate sterilized 350 mL LB flask with BL21 bacteria containing protein expression plasmid by the following process: Add 350 uL of 35 mg/mL Kanamycin (1000×) and 1.75 mL of 40% glucose (500 uL per 100 mL of culture). Then pick a colony from stored LB-agar plate or add a scoop of glycerol stock and incubate overnight at 225 rpm, 37° C. [Innova 4330 incubator shaker, made by New Brunswick Scientific]. The next morning, add 1 mL of 35 mg/mL Kanamycin to each 950 mL LB flask (1000×). Inoculate each of the 6×950 mL LB flasks with 50 mL of overnight culture. Incubate the 6×1 L flasks at 37° C. and 225 rpm, until $OD_{600}$ is 0.8-1.0 (approx. 1 hour). Add isopropyl beta-D thiogalactopyranoside to 1 mM final concentration (add 1 mL of 1M solution per flask). The solution is incubated at 37° C. for 4 hours at 180 rpm. Centrifuge culture at 5,000 rpm for 15 min at 4° C. Pour off the supernatant and scoop bacteria pellets into a 50 mL conical tube. Store at −20° C.

Example 3

Lysis

From 12 L of frozen bacteria pellet from Example 1, stored at −20° C. in a 50 mL conical tube. The cells are first lysed by the following procedure: Thaw bacteria pellet at room temp. Prepare 500 mL of (incomplete) cell lysis buffer (150 mL per 6 L of pellet) with 20 mM MES (pH 6.8, 0.22 um filtered), 200 mM NaCl and fill to 500 mL with DI water. Scoop thawed bacteria pellet into a clean 500 mL glass beaker and resuspend pellet in ~200 mL of lysis buffer. Break up the pellets. Add remaining lysis buffer reagents to the 500 mL beaker, [1 mM PMSF, 1 mM DTT, DNase1, ~10 ug/mL; lysozyme, ~125 ug/mL.]. Fill beaker to ~300 mL with lysis buffer. Stir lysate at room temp for 30 min-1 hour. Place lysis beaker into an ice water bath deep enough for all of the lysate to be cooled. Sonicate the lysate, using the macrotip on the sonicator. Pulse 1 second on, 1 second off for 15 min pulsing (30 min total run time) at 70% amp. Transfer lysate to 40 mL centrifuge tubes. Spin at 30,000×g for 30 min at 4° C. Vacuum filter supernatant into a clean 500 mL bottle. Use a 0.8 um filter first, then a 0.22 um filter. If the lysate is too thick to filter, add more DNase and/or lysozyme and incubate at room temp.

Example 4

Purification of His-Tau40 WT (SEQ ID NO: 26) Via His-Tag Affinity (20 mL HisPrep FF 16/10 Column)

Prepare FPLC Buffers:
a. Buffer A—20 mM MES, pH 6.8, 20 mM Imidazole, 100 mM NaCl, 0.22 um filtered;
b. Buffer B—20 mM MES, pH 6.8, 0.5M Imidazole, 100 mM NaCl 0.22 um filtered Load lysate onto a 20 mL HisPrep FF column, flow rate at 5 mL/min. Wash column with 6 CVs of buffer A. Elute into 10 mL fractions using 20 CVs of buffer B added on a 0-100% gradient at 5 mL/min. Pool desired fractions. Store at 4° C. overnight if necessary.

Example 5

Inhibition of His Tau40 WT with Peptide Inhibitors—Thioflavin T Assay

The following describes the experimental method used to evaluate the $IC_{50}$ of Tau amyloid inhibition by the peptide inhibitors described above. The physical setup of inhibitor peptides in these dose responses is done automatically with an 8-span head on a BioMek3000 liquid handler into Costar optically 96-well clear bottom black plates. Inhibitor peptides are kept frozen at −80 C in 100% DMSO solution at a concentration of 20 mM and thawed immediately before the assay. The Biomek makes two serial dilutions of a single inhibitor for a duplicate 6-point dose response curve. This is followed by addition a 5× reaction buffer. The final reaction buffer concentration in the assay is 50 mM MES, pH 6.8, 125 mM NaCl, 10 µM Heparin, 50 µM ThT. The Tau substrate is added by a 96-head Multimek liquid handler making a 4:10 dilution of Tau40 P301L protein (SEQ ID NO: 25) to which DTT is added directly before setting up the assay. The final concentrations of Tau40 P301L and DTT in the assay is 2.5 μM and 5 mM, respectively. Amyloid formation is measured by monitoring Thioflavin T fluorescence every 10 minutes with excitation and emission wavelengths of 440 and 485 nm using fluorescence plate readers. The assay plates are kept in the plate reader during the whole duration of the assay and incubated at 37° C. with continuous shaking for 24 hours. Plate reader models Genios and Spectrafluor Plus produced by Tecan are used and data is acquired using Magellan software. The calculation of $IC_{50}$ is done by an automatic algorithm developed using the R statistical programming language. Briefly, the algorithm uses data exported in excel format from the plate reader to average the cumulative ThT fluorescence for each inhibitor concentration in the 6-point dose response. The $IC_{50}$ is calculated as the midpoint of a sigmoid curve fitted to the correlation of normalized ThT fluorescence and inhibitor concentration. The results are reported in Table 5.

TABLE 5

| Tau40 assay | | |
| --- | --- | --- |
| Peptide | PEP ID NO: | IC50 (μM) |
| wrlrihw | 101 | 0.31 |
| wrlrihw | 101 | 0.32 |
| rlkirihy | 451 | 0.51 |
| wrlrimw | 452 | 0.54 |
| wrlrihm | 453 | 0.58 |
| lkirihyl | 193 | 0.65 |
| lkiriryh | 194 | 0.65 |
| wklwlrw | 91 | 0.65 |
| wwrvklrw | 195 | 0.66 |
| lkirihyh | 147 | 0.67 |
| vrwwklrw | 196 | 0.68 |
| wrlkvrwl | 197 | 0.68 |
| wlkirihy | 198 | 0.69 |
| wkvwvryw | 92 | 0.7 |
| lkvrwwwr | 199 | 0.7 |
| wrlrlrw | 200 | 0.7 |
| ririrw | 75 | 0.71 |
| kvrwwlrw | 201 | 0.71 |
| lwrlkvrw | 202 | 0.72 |
| ukirihy | 203 | 0.73 |
| vrwwwrlk | 204 | 0.74 |
| fririhhf | 113 | 0.74 |
| wrlkvrww | 3 | 0.75 |
| twrlkvrw | 205 | 0.75 |
| lkiriwyh | 206 | 0.78 |

TABLE 5-continued

| Tau40 assay | | |
| --- | --- | --- |
| Peptide | PEP ID NO: | IC50 (μM) |
| kwrlkvrw | 207 | 0.78 |
| lkirilyh | 208 | 0.79 |
| gwrlkvrw | 209 | 0.79 |
| fririhhf | 113 | 0.81 |
| lrlkvrwl | 210 | 0.81 |
| lkirfhy | 211 | 0.81 |
| lkiwikyh | 212 | 0.81 |
| wkvwvryw | 92 | 0.81 |
| wkvqvrlw | 2 | 0.82 |
| hrlkvrwh | 213 | 0.82 |
| lkirifyh | 214 | 0.82 |
| wrfkfrw | 215 | 0.82 |
| fklklrwf | 57 | 0.83 |
| lkfrihy | 216 | 0.83 |
| rwrlkvrw | 217 | 0.83 |
| wrlkvrwf | 218 | 0.84 |
| lkirimy | 219 | 0.84 |
| wrrkvrww | 220 | 0.85 |
| lrlkvrww | 221 | 0.85 |
| lkiriryh | 194 | 0.85 |
| wrlkvrwh | 222 | 0.86 |
| lkilihyh | 223 | 0.86 |
| rlkvrwww | 224 | 0.87 |
| frlkvrwf | 4 | 0.87 |
| rrlkvrww | 225 | 0.88 |
| wrfkvrw | 226 | 0.88 |
| rkirihyh | 227 | 0.89 |
| lkirirfh | 414 | 0.9 |
| lkirbhy | 228 | 0.9 |
| ewrlkvrw | 229 | 0.9 |
| wrlkvrwr | 230 | 0.91 |
| frlkvrww | 231 | 0.91 |
| fkirihyf | 232 | 0.91 |
| fkirihhy | 122 | 0.91 |
| klklrww | 448 | 0.92 |
| lqfdlqyf | 142 | 0.93 |
| lkikihy | 233 | 0.93 |
| wwrlkvrw | 234 | 0.93 |

TABLE 5-continued

Tau40 assay

| Peptide | PEP ID NO: | IC50 (μM) |
|---|---|---|
| wwlrihw | 425 | 0.94 |
| wklklwww | 14 | 0.94 |
| tlkirihy | 235 | 0.94 |
| glkirihy | 236 | 0.96 |
| lrikirfh | 421 | 0.97 |
| lrirlhyh | 420 | 0.97 |
| lkiwiyyh | 237 | 0.97 |
| lqfdlqyf | 142 | 0.98 |
| wkvwvrgw | 93 | 0.99 |
| wrlrvrww | 238 | 1 |
| lririhyh | 239 | 1 |
| lkirihlh | 240 | 1 |
| lklhlhfh | 434 | 1.01 |
| lklrirhh | 415 | 1.01 |
| wrlkerww | 241 | 1.01 |
| mrlrihw | 242 | 1.01 |
| klkirihy | 243 | 1.01 |
| wklwlrw | 91 | 1.02 |
| lkirizy | 244 | 1.03 |
| lkirihy | 245 | 1.04 |
| wrmrihw | 246 | 1.04 |
| flkirihy | 247 | 1.04 |
| fklklrw | 413 | 1.05 |
| lkirlhhw | 143 | 1.07 |
| fklrlrhw | 123 | 1.07 |
| fklkikw | 132 | 1.08 |
| wrlkvaw | 248 | 1.08 |
| lkiklrhy | 144 | 1.09 |
| bkirihy | 249 | 1.09 |
| lkiklrhy | 144 | 1.09 |
| fklkikw | 132 | 1.1 |
| lririkhy | 145 | 1.1 |
| wrlrihww | 20 | 1.11 |
| wlrvqvklw | 416 | 1.11 |
| lkirihyf | 250 | 1.11 |
| wikirw | 21 | 1.12 |
| fririkhy | 114 | 1.12 |
| lkiriuy | 251 | 1.12 |

TABLE 5-continued

Tau40 assay

| Peptide | PEP ID NO: | IC50 (μM) |
|---|---|---|
| wwrfhwr | 43 | 1.13 |
| frlkirhw | 117 | 1.15 |
| fririkhy | 114 | 1.15 |
| lhlkiryh | 410 | 1.16 |
| lkbrihy | 252 | 1.16 |
| elkirihy | 253 | 1.16 |
| mrlkvrw | 254 | 1.17 |
| wrlktrw | 255 | 1.17 |
| ylkirihy | 256 | 1.19 |
| lririkhy | 145 | 1.19 |
| whlrlhw | 109 | 1.19 |
| frlkirhw | 117 | 1.2 |
| frlrihw | 270 | 1.2 |
| rlkirw | 23 | 1.21 |
| wikirw | 21 | 1.21 |
| lrirlhhf | 146 | 1.22 |
| fririhhw | 115 | 1.24 |
| frlklrhw | 116 | 1.24 |
| lkirihyh | 147 | 1.25 |
| walkvrw | 257 | 1.25 |
| wrukvrw | 258 | 1.25 |
| hlkirihy | 259 | 1.25 |
| fhirirhw | 138 | 1.26 |
| yrvriewl | 159 | 1.27 |
| wkvwvrgw | 93 | 1.27 |
| wrlrmhw | 260 | 1.28 |
| wrlwihw | 428 | 1.29 |
| lkihirhw | 148 | 1.29 |
| wrlrihww | 20 | 1.29 |
| frvrirhw | 118 | 1.31 |
| fhirirhw | 138 | 1.31 |
| fririhhw | 115 | 1.31 |
| fwrlkvrw | 261 | 1.32 |
| wrlriht | 262 | 1.33 |
| fklklrhw | 125 | 1.34 |
| fkihlrhw | 124 | 1.34 |
| fklklrhw | 125 | 1.36 |
| wrlkfrw | 263 | 1.36 |

TABLE 5-continued

Tau40 assay

| Peptide | PEP ID NO: | IC50 (µM) |
|---|---|---|
| friklrw | 47 | 1.37 |
| fwlklrwf | 15 | 1.38 |
| fklhlrhw | 126 | 1.39 |
| welkvrww | 264 | 1.39 |
| lkihirhw | 148 | 1.39 |
| rikirw | 26 | 1.4 |
| frlriww | 423 | 1.41 |
| lririrfh | 152 | 1.41 |
| hrlkvrww | 265 | 1.41 |
| lkirlhhw | 143 | 1.42 |
| hwrlkvrw | 266 | 1.42 |
| lkiruhy | 267 | 1.43 |
| ywrlkvrw | 268 | 1.43 |
| yrvriewl | 159 | 1.43 |
| lkirihya | 269 | 1.45 |
| rwrwrw | 17 | 1.46 |
| frirlrw | 56 | 1.46 |
| friklrw | 47 | 1.46 |
| ririrw | 75 | 1.47 |
| frlrihw | 270 | 1.47 |
| lkiriay | 271 | 1.48 |
| wrlriaw | 272 | 1.49 |
| wqlkvrw | 273 | 1.49 |
| rikirw | 26 | 1.49 |
| fklhlrhw | 129 | 1.51 |
| lkirihrh | 274 | 1.51 |
| wrlkvrwe | 275 | 1.52 |
| eirlhw | 74 | 1.54 |
| lrirlhhf | 146 | 1.54 |
| wrvqvrw | 102 | 1.54 |
| whlrirw | 19 | 1.54 |
| wkvkiqyh | 100 | 1.56 |
| wrtkvrw | 276 | 1.56 |
| mrlkvrw | 254 | 1.57 |
| lkiriyy | 277 | 1.57 |
| wrvqvrw | 102 | 1.57 |
| fkikikw | 60 | 1.57 |
| wrlkvrrw | 278 | 1.58 |

TABLE 5-continued

Tau40 assay

| Peptide | PEP ID NO: | IC50 (µM) |
|---|---|---|
| lkurihy | 279 | 1.59 |
| wrlqvrw | 280 | 1.6 |
| wrlkvrww | 3 | 1.61 |
| rlrirw | 27 | 1.61 |
| wkvkiqyh | 100 | 1.61 |
| wrlkvqw | 281 | 1.62 |
| whlrirw | 19 | 1.63 |
| urlkvrw | 282 | 1.63 |
| tkirihy | 283 | 1.63 |
| wrlkvrew | 284 | 1.64 |
| lkiqihy | 285 | 1.64 |
| lrlhlrhw | 149 | 1.64 |
| fkihikhy | 127 | 1.65 |
| fkikikw | 60 | 1.65 |
| lhiklrwh | 151 | 1.65 |
| wrbkvrw | 286 | 1.65 |
| lkuruhy | 287 | 1.65 |
| rtlkivwr | 22 | 1.67 |
| klklrwf | 438 | 1.67 |
| wkvnvrlw | 95 | 1.67 |
| rrlkvrwr | 439 | 1.68 |
| rlkirw | 23 | 1.68 |
| wkvkfqhw | 94 | 1.69 |
| wkvnvrlw | 95 | 1.71 |
| fklhirhw | 128 | 1.71 |
| wrlevrww | 288 | 1.72 |
| wkvqvrw | 89 | 1.73 |
| fkiklkw | 35 | 1.74 |
| wkvqvrw | 89 | 1.76 |
| fklhirhw | 128 | 1.76 |
| frlklrfh | 426 | 1.77 |
| wfkiklel | 110 | 1.77 |
| wrlkvrw | 289 | 1.77 |
| lrlrikhf | 150 | 1.78 |
| fkihikhy | 127 | 1.79 |
| rrlrihw | 290 | 1.79 |
| lkirihyr | 291 | 1.81 |
| wrlhvrww | 292 | 1.82 |

TABLE 5-continued

Tau40 assay

| Peptide | PEP ID NO: | IC50 (µM) |
|---|---|---|
| brlkvrw | 293 | 1.82 |
| wnlkvrw | 294 | 1.82 |
| lhiklrwh | 151 | 1.83 |
| fkiklkw | 35 | 1.84 |
| lhirlrhw | 153 | 1.84 |
| lkihihyh | 295 | 1.85 |
| fhirlewh | 139 | 1.86 |
| lririrfh | 152 | 1.87 |
| frlkvrwf | 4 | 1.87 |
| kikikw | 66 | 1.87 |
| wrlkvnw | 296 | 1.87 |
| lkirixy | 297 | 1.88 |
| lhirlrhw | 153 | 1.88 |
| fkirihhy | 122 | 1.89 |
| rlkvrww | 298 | 1.9 |
| wrirlryw | 104 | 1.91 |
| lkiwihyh | 299 | 1.91 |
| frlkvrwf | 4 | 1.91 |
| prirlhw | 33 | 1.94 |
| hyhirikl | 300 | 1.94 |
| wrlavrw | 301 | 1.94 |
| prirlhw | 33 | 1.95 |
| wrlriww | 103 | 1.98 |
| lkifiyyh | 302 | 1.99 |
| rirwrw | 50 | 2.02 |
| wikiwr | 29 | 2.02 |
| fhihikfh | 437 | 2.02 |
| riklrw | 24 | 2.03 |
| lkiriayh | 303 | 2.03 |
| rirlrw | 38 | 2.04 |
| rlrihww | 164 | 2.05 |
| rlrihww | 164 | 2.05 |
| riklrw | 24 | 2.06 |
| lrlhlrhw | 149 | 2.06 |
| wmlrihw | 304 | 2.07 |
| wtlrihw | 305 | 2.07 |
| wrlnvrw | 306 | 2.07 |
| fwlklrwf | 15 | 2.08 |

TABLE 5-continued

Tau40 assay

| Peptide | PEP ID NO: | IC50 (µM) |
|---|---|---|
| felrlhwh | 133 | 2.11 |
| wrlkbrw | 307 | 2.11 |
| wrlkurw | 308 | 2.12 |
| lrvqvrl | 441 | 2.13 |
| yhlklhyw | 440 | 2.17 |
| wlrvqvkw | 111 | 2.18 |
| fhirlewh | 139 | 2.19 |
| lairihyh | 309 | 2.19 |
| rirlrw | 38 | 2.2 |
| wlrvqvkw | 111 | 2.21 |
| lklkikhf | 154 | 2.21 |
| wrlwvrww | 310 | 2.23 |
| wkvqvrlw | 2 | 2.26 |
| rirwywk | 311 | 2.27 |
| arlrihw | 312 | 2.28 |
| wrlkveww | 313 | 2.3 |
| felhikwh | 134 | 2.34 |
| wrlritw | 314 | 2.36 |
| wriwiryw | 105 | 2.38 |
| wkvqvrlw | 2 | 0.95; 2.39 |
| wrlevrw | 315 | 2.4 |
| felrlhwh | 133 | 2.41 |
| lkleirwh | 429 | 2.42 |
| lrlrikhf | 150 | 2.43 |
| leirihy | 316 | 2.43 |
| lkimihy | 317 | 2.44 |
| lkiriehy | 155 | 2.45 |
| lkiriheh | 318 | 2.45 |
| wrirlryw | 104 | 2.45 |
| wqlkvqw | 319 | 2.47 |
| lkizihy | 320 | 2.47 |
| frvkiqhw | 120 | 2.49 |
| wwlklrww | 81 | 2.52 |
| wfkiklel | 110 | 2.53 |
| lkiuihy | 321 | 2.54 |
| frikirw | 61 | 2.56 |
| wklklrww | 13 | 2.56 |
| frikirw | 61 | 2.57 |

TABLE 5-continued

Tau40 assay

| Peptide | PEP ID NO: | IC50 (μM) |
|---|---|---|
| welrihw | 322 | 2.58 |
| feirihyh | 442 | 2.59 |
| wrlkvra | 323 | 2.61 |
| wriwiryw | 105 | 2.61 |
| lkiriey | 324 | 2.63 |
| wrlaihw | 325 | 2.65 |
| wklwlrww | 12 | 2.67 |
| hwrwrwr | 326 | 2.69 |
| rlrihwf | 446 | 2.69 |
| trlrihw | 327 | 2.7 |
| wrlkvdw | 328 | 2.7 |
| lelkikfw | 5 | 2.73 |
| lklkikhf | 154 | 2.75 |
| fkirihyh | 329 | 2.76 |
| wrltihw | 330 | 2.76 |
| wdlkvrw | 331 | 2.76 |
| wrlrifw | 332 | 2.79 |
| wklvvw | 79 | 2.81 |
| lkixihy | 333 | 2.81 |
| lelkikfw | 5 | 2.85 |
| whvkfelf | 424 | 2.88 |
| lkiriha | 334 | 2.92 |
| kikikw | 66 | 2.92 |
| lkiyihy | 335 | 2.93 |
| wklwlrww | 12 | 2.94 |
| rlrirw | 27 | 2.96 |
| lkiaihy | 336 | 2.96 |
| klklkw | 80 | 2.97 |
| wrirow | 337 | 3.0 |
| wrlriww | 103 | 3.06 |
| fkirikwh | 130 | 3.06 |
| erlkvrw | 338 | 3.07 |
| felhikwh | 134 | 3.11 |
| wrldvrw | 339 | 3.13 |
| lkirihrh | 274 | 3.16 |
| lkiwiwyh | 340 | 3.19 |
| fhirlrhh | 141 | 3.21 |
| lkirrhyh | 341 | 3.21 |

TABLE 5-continued

Tau40 assay

| Peptide | PEP ID NO: | IC50 (μM) |
|---|---|---|
| arlkvrw | 342 | 3.23 |
| wrakvrw | 343 | 3.23 |
| wrlkarw | 344 | 3.23 |
| walrihw | 345 | 3.23 |
| wrlrahw | 346 | 3.23 |
| wrlriha | 347 | 3.23 |
| wrleihw | 348 | 3.23 |
| wrlriew | 349 | 3.23 |
| wrlmihw | 350 | 3.23 |
| wrtrihw | 351 | 3.23 |
| wrlnvnw | 352 | 3.23 |
| frirlrw | 56 | 3.23 |
| wrlkvrww | 3 | 3.23 |
| wkvhiqhw | 99 | 3.29 |
| fhlkirhh | 140 | 3.29 |
| lkirihye | 353 | 3.32 |
| lkieihy | 354 | 3.32 |
| frlwihw | 417 | 3.33 |
| wrarihw | 355 | 3.33 |
| wrlrthw | 356 | 3.33 |
| wnlnvrw | 357 | 3.33 |
| lkifiwyh | 358 | 3.33 |
| erlkvrww | 359 | 3.36 |
| fhlkirhh | 140 | 3.36 |
| fkielhwh | 129 | 3.37 |
| rlkvrw | 165 | 3.38 |
| tlkivw | 78 | 3.38 |
| fkleiryh | 411 | 3.38 |
| feirlwhh | 412 | 3.38 |
| rlrlkw | 450 | 3.43 |
| ldlrfkly | 422 | 3.43 |
| fkielhwh | 129 | 3.44 |
| wwlklrw | 433 | 3.54 |
| wkvqvryw | 449 | 3.54 |
| akirihyh | 360 | 3.54 |
| kwrwyrr | 361 | 3.55 |
| wklklrw | 90 | 3.56 |
| rihyhikl | 362 | 3.59 |

TABLE 5-continued

Tau40 assay

| Peptide | PEP ID NO: | IC50 (μM) |
|---|---|---|
| rlkvrw | 165 | 3.59; 3.81 |
| wlkivw | 83 | 3.62 |
| lkieihyh | 363 | 3.64 |
| rwkvrw | 444 | 3.7 |
| rlrvrw | 166 | 3.71 |
| fhlhlkhw | 443 | 3.74 |
| wrlriww | 16 | 3.76 |
| frlrihwf | 58 | 3.77 |
| kvrwwwrl | 364 | 3.84 |
| hkirihyh | 365 | 3.84 |
| friklkwh | 121 | 3.88 |
| friklkwh | 121 | 3.9 |
| lairihy | 366 | 3.98 |
| hrfkvqly | 445 | 4.03 |
| leirihyh | 367 | 4.07 |
| wwlrihww | 30 | 4.09 |
| wklklrww | 13 | 4.13 |
| fklwlrwf | 9 | 4.19 |
| feirlhhw | 430 | 4.2 |
| fhirlrhh | 141 | 4.3 |
| frlwihwf | 10 | 4.39 |
| klkwlw | 368 | 4.41 |
| lhiklkhf | 156 | 4.44 |
| lkiriehy | 155 | 4.53 |
| lkifihyh | 369 | 4.57 |
| kirihyhl | 370 | 4.59 |
| lhiklkhf | 156 | 4.64 |
| yrlkvrw | 371 | 4.69 |
| yhvkfrhw | 160 | 4.71 |
| rlrvrw | 166 | 4.76 |
| rlkvrw | 165 | 4.79 |
| wnlkvnw | 372 | 4.86 |
| kirihyh | 373 | 4.92 |
| felklrwh | 135 | 4.94 |
| lkirih | 374 | 4.95 |
| whvrirhv | 107 | 5.03 |
| ihyhrikl | 375 | 5.12 |
| yrvriqhi | 161 | 5.13 |
| frvkiehw | 119 | 5.25 |
| felklrwh | 135 | 5.3 |
| leikirhw | 157 | 5.38 |
| wrlriww | 16 | 5.41 |
| fkirikwh | 130 | 5.46 |
| wrlrvw | 42 | 5.48 |
| wrhkvrw | 376 | 5.5 |
| wrlrvw | 42 | 5.5 |
| wlkvrw | 46 | 5.51 |
| ekirihy | 377 | 5.58 |
| wwlrihww | 30 | 5.61 |
| rlkwrw | 432 | 5.62 |
| wrlkhrw | 378 | 5.86 |
| lrieiewh | 158 | 5.89 |
| klklrw | 39 | 5.92 |
| wrlwihww | 11 | 5.99 |
| klklrw | 39 | 5.99 |
| fhieirhf | 431 | 6.06 |
| yrirlehv | 162 | 6.3 |
| whvrlnhl | 108 | 6.39 |
| lkirihah | 379 | 6.41 |
| wrllvrww | 380 | 6.46 |
| lkvrww | 381 | 6.48 |
| yririnhl | 163 | 6.5 |
| tlkivw | 78 | 6.81; 11.23 |
| wrfhihfy | 8 | 6.53 |
| felrikhy | 136 | 6.57 |
| wqlqvrw | 382 | 6.57 |
| rihyhlki | 383 | 6.63 |
| tlkivw | 78 | 6.66 |
| wrlkvew | 384 | 6.67 |
| vkvwgrlw | 419 | 6.72 |
| frlriwwf | 18 | 6.85 |
| wrvhfehw | 106 | 6.86 |
| rlrihw | 36 | 6.87 |
| klkikw | 34 | 6.87 |
| fhleirhw | 427 | 6.87 |
| frlwihwf | 10 | 6.88 |

TABLE 5-continued

Tau40 assay

| Peptide | PEP ID NO: | IC50 (μM) |
|---|---|---|
| klkivw | 52 | 6.9 |
| rirlhw | 41 | 6.97 |
| wikivr | 31 | 6.97 |
| wrfhihfy | 8 | 7 |
| rlkvww | 436 | 7.01 |
| fklwlrwf | 9 | 7.03 |
| frlrihwf | 58 | 7.09 |
| fklhlkhy | 131 | 7.19 |
| wrukurw | 385 | 7.21 |
| fklklwwf | 6 | 7.22 |
| fwlrihwf | 7 | 7.28 |
| irihyhlk | 386 | 7.39 |
| wklklrw | 90 | 7.39 |
| ekirihyh | 387 | 7.42 |
| twrlvl | 73 | 7.46 |
| fklhlkhy | 131 | 7.53 |
| wrlwihww | 11 | 7.56 |
| fwlrihwf | 7 | 7.56 |
| wwlklrww | 81 | 7.64 |
| welkvrw | 388 | 7.92 |
| rlwvrw | 44 | 8.02 |
| tlkiew | 87 | 8.08 |
| lkirieyh | 389 | 8.14 |
| wdlrlqyw | 112 | 8.33 |
| awakvrw | 390 | 8.38 |
| wkvwgrvw | 98 | 8.42 |
| wflrihw | 391 | 8.71 |
| leikirhw | 157 | 8.72 |
| wrtktrw | 392 | 8.93 |
| ilkivw | 53 | 9.32 |
| wrbkbrw | 393 | 9.33 |
| lrieiewh | 158 | 9.68 |
| ihyhlkir | 394 | 9.7 |
| erlrihw | 395 | 9.9 |
| wklklwww | 14 | 9.91 |
| wrlrihe | 396 | 10 |
| welkvew | 397 | 10 |
| wdlrlqyw | 112 | 10.09 |

TABLE 5-continued

Tau40 assay

| Peptide | PEP ID NO: | IC50 (μM) |
|---|---|---|
| tlkivw | 78 | 10.24 |
| fkieieyh | 418 | 10.34 |
| wkvwgkvw | 96 | 10.44 |
| lkarihyh | 398 | 10.44 |
| wkvwgkvw | 96 | 10.63 |
| frlriwwf | 18 | 10.79 |
| wklklwww | 14 | 10.83 |
| arlkarw | 399 | 11.24 |
| frlkirw | 37 | 11.72 |
| wevqvew | 435 | 11.72 |
| felrikhy | 136 | 11.96 |
| frlkirw | 37 | 12.18 |
| lktrihy | 400 | 12.53 |
| ararihw | 401 | 12.64 |
| wrakarw | 402 | 12.73 |
| tiklvw | 167 | 13.72 |
| wdldvrw | 403 | 13.97 |
| wkvwgrvw | 98 | 14.07 |
| feleiewh | 137 | 14.31 |
| tiklvw | 167 | 14.35 |
| fklklwwf | 6 | 14.96 |
| wrlkv | 404 | 15.08 |
| lkrrihyh | 405 | 15.43 |
| elkivw | 86 | 15.96 |
| elkivw | 86 | 16.62 |
| wrlkvr | 406 | 18.49 |
| wkvpvryw | 97 | 19.03 |
| wrhkhrw | 407 | 19.17 |
| wrekvrww | 408 | 19.27 |
| feleiewh | 137 | 19.46 |
| lkiaihyh | 409 | 19.51 |
| lefelkyw | 447 | 19.73 |
| wkvpvryw | 97 | 19.8 |

Example 6

Modified Peptide Inhibitors

Additional peptides were prepared that included linkers and CPP sequences. Using standard peptide synthetic methods described in Example 1, modified peptides were prepared that included linkers and CPP sequences. TAMRA and TAMRA5 are isomers of tetramethyl rhodamine dyes. The following sequences were prepared and tested in the assay described in Example 5. "X" means no IC50 observed at the highest dose tested. The results are reported in Table 6.

TABLE 6

Tau40 assay-Modified peptedes

| Peptide | PEP ID NO: | IC50 (μM) |
|---|---|---|
| RRRRRRRR-GGSGG-rlkvrw | 454 | 6.07 |
| Tam-RRRRRRRR-GGSGG-rlkvrw | 455 | 20.05 |
| Tam-YGRKKRRQRRR-GGSGG-rlkvrw | 456 | 6.60 |
| YGRKKRRQRRR-GGSGG-rlkvrw | 457 | 1.73 |
| Tam-RRRRRRRRR-GGSGG-lelkikfw | 475 | 8.71 |
| Tam-RRRRRRRRR-GGSGG-elkivw | 459 | x |
| Tam-RRRRRRRRR-GGSGG-tlkivw | 460 | 4.92 |
| Tam-RRRRRRRRR-GGSGG-wkvqvrlw | 461 | 5.53 |
| Tam-RRRRRRRRR-GGSGG-wrlkvrww | 462 | 20.50 |
| RRRRRRRRR-GGSGG-wrlkvrww | 463 | x |
| Tam-YGRKKRRQRRR-GGSGG-wrlkvrww | 464 | 6.60 |
| Tam-RRRRRRRRR-GGSGG-wriwiryw | 465 | 4.94 |
| TAMRA5-PEG2-wrakaraw-OH | 466 | 9.17 |

Example 7

Pre-Dosing of Peptide Inhibitors

HEK293 cells stably expressing the TauRD (P301S)-Nluc and TauRD (P301S)-Cluc split luciferase compliment pair, originally developed and described by Mirbaha et al., [THE JOURNAL OF BIOLOGICAL CHEMISTRY VOL. 290, NO. 24, pp. 14893-14903, Jun. 12, 2015] were obtained from Washington University. Luciferin potassium salt was obtained from Gold Biotechnology USA, luciferase cell lysis buffer obtained from New England Biolabs, Lipofectamine 2000, DMEM and OPTI-MEM obtained from Thermo Fisher Scientific and Heparin (average MW of 18000) was obtained from Sigma. Tau fibrils were prepared by incubating His-Tau40 P301L Tau (SEQ ID NO: 27) at 20 μM in a 1.0 mL volume of reaction buffer (50 mM MES, pH 6.8, 125 mM NaCl, 10 μM Heparin, 5 mM DTT) for 24 hours at 37° C. with continuous shaking in a capped 1.5 mL polypropylene sample tube. The Tau aggregation reporter cells were plated in white 96 well tissue culture treated plates (Greiner Bio-one Cat #655083) at a starting density of 30,000 cells/well in 100 μL/well DMEM containing 10% v/v fetal bovine serum. The plates were then incubated overnight in a humidified incubator set at 37° C. and 5% $CO_2$ before adding the test compounds. Peptide stocks, pre-dissolved at 4 mM in water, were serially diluted in OPTIMEM at 10 times their reported test concentration across a 10-point dose curve. 10 μL of each concentration was then added to triplicate cell culture wells 4 hours before inducing a cellular tau aggregation response with tau fibril: Lipofectamine 2000 complexes. Immediately before seeding the cell assays, the Tau fibrils were sonicated for 5 minutes with a microtip sonicator, and an aliquot (50-200 μL) diluted to 12 μM in OPTIMEM. One volume of 12.5% v/v Lipofectamine 2000 in OPTIMEM is added, creating a 6 μM Tau fibril solution, and allowed to complex at room temperature for 20 minutes. The solution is diluted again with OPTIMEM to a 650 nM Tau concentration, and 20 μL/well added to the pre-dosed cells for a final Tau concentration, in fibril form, of 100 nM. After 48 hours in the incubator, the assay plate is aspirated and wells lysed with 20 μL of luciferase cell lysis buffer. An additional 20 μL of luciferase cell lysis buffer, containing 10 mM MgCl2, 300 μM ATP and 940 μM Luciferin, is added immediately before reading the luciferase compliment response intensity on a Perkin Elmer Envision 2110 using a 1 second integration time of relative light units. $IC_{50}$ values are calculated by normalizing peptide treated samples as a percent of the treatment free controls and plotting the normalized values vs the Log of inhibitor concentration. The $IC_{50}$ value is determined with the log(inhibitor) vs. normalized response—variable slope curve fitting algorithm performed by GraphPad Prism version 7.00 for Windows, GraphPad Software, La Jolla Calif. The results are reported in Table 7 and 7a. "X" means no EC50 observed at the highest dose tested

TABLE 7

HEKCell Assay with CPP Linked peptides

| Sequence | PEP ID NO | $EC_{50}$ (μM) |
|---|---|---|
| Tam-RRRRRRRRRPI-kfrfyhr | 467 | x |
| YGRKKRQRRRRPI-kfrfyhr | 468 | x |
| RRRRRRRR-GGSGG-rlkvrw | 454 | x |
| RRRRRRRRRPI-ltritle [comparator] | 469 | x |
| Tam-RRRRRRRRR-GGSGG-lelkikfw | 475 | 12.1 |
| Tam-RRRRRRRRR-GGSGG-elkivw | 459 | 5.6 |
| Tam-RRRRRRRRR-GGSGG-tlkivw | 460 | 3.6 |
| Tam-RRRRRRRRR-GGSGG-wkvqvrlw | 461 | 1.5 |
| Tam-RRRRRRRRR-GGSGG-wrlkvrww | 462 | 1.5 |
| RRRRRRRRR-GGSGG-wrlkvrww | 463 | 1.7 |
| Tam-YGRKKRRQRRR-GGSGG-wrlkvrww | 464 | 1.8 |

TABLE 7a

HEKCell Assay with CPP Linked peptides

| Sequence | PEP ID NO | DOSE | $EC_{50}$ (μM) |
|---|---|---|---|
| RRRRRRRR-PI-kfrfyhr | 470 | 20 | inactive |
| RRRRRRRR-GGSGG-rlkvrw | 454 | 30 | inactive |
| YGRKKRRQRRR-GGSGG-rlkvrw | 457 | 30 | inactive |
| RRRRRRRRR-GGSGG-lelkikfw | 458 | 20 | 16.4 |
| RRRRRRRRR-GGSGG-elkivw | 468 | 20 | 11.7 |
| RRRRRRRRR-GGSGG-tlkivw | 472 | 20 | 2.9 |
| RRRRRRRRR-GGSGG-wkvqvrlw | 466 | 20 | 2.1 |

TABLE 7a-continued

HEKCell Assay with CPP Linked peptides

| Sequence | PEP ID NO | DOSE | EC$_{50}$ (μM) |
|---|---|---|---|
| RRRRRRRRR-GGSGG-wrlkvrww | 465 | 30 | 1.3-1.9 |
| RRRRRRRRR-GGSGG-wrlkvrww | 463 | 20 | 2.3 |
| RRRRRRRRR-GGSGG-wriwiryw | 471 | 20 | 0.9 |

Example 8

Inhibition of VQIINK (SEQ ID NO: 1; PEPTIDE ID NO: 192) Aggregation with Peptide Inhibitors The following describes the experimental method used to evaluate the IC$_{50}$ of aggregation of VQIINK (SEQ ID NO: 1; PEPTIDE ID NO: 192) inhibition by the peptide inhibitors described above. The peptide sequence comprising Ac-VQIINK-NH$_2$ (SEQ ID NO: 23) (C-terminal amidated) is prepared using the peptide synthetic method described above. The Ac-VQIINK-NH$_2$ (SEQ ID NO: 23) is stored at 10 mM in 100% DMSO at −80 C, and an aliquot volume sufficient for a single aggregation assay plate is removed. The stock aggregation buffer (5×) is prepared with the following: 250 mM NaPhosphate (pH 8.0), 125 mM KCl, and 500 micromolar ThioflavinT (ThT). The aggregation assay is conducted with shaking, at room temperature, on a plate reader model FLX-800 by BioTek. Water for primary Ac-VQIINK-NH$_2$ (SEQ ID NO: 23) dissolution is cooled to 4 degrees Celsius (7.245 milliliters). Buffer is added from the 5× stock (40 microliters, final volume in assay plate is 130 microliters, final buffer concentrations 50 millimolar NaPO$_4$ (pH 8.0); 25 milllimolar KCl; and 100 micromolar ThioflavinT). The assay plate is cooled to 4 degrees Celcius. The Ac-VQIINK-NH$_2$ (SEQ ID NO: 23) (105 microliters) is added to the chilled water (final volume of 7.350 milliliters), this is added into a pooled reservoir, and using a 96-channel robotic pipettor, 70 microliters diluted Ac-VQIINK-NH$_2$ (SEQ ID NO: 23) is added to the assay plate to achieve a final concentration of 50 micromolar in a 200 microliter final assay volume (per well). Data is acquired using Magellan software. The calculation of IC$_{50}$ is done by an automatic algorithm developed using the R statistical programming language. Briefly, the algorithm uses data exported in excel format from the plate reader to average the cumulative ThT fluorescence for each inhibitor concentration in the 6-point dose response. The IC$_{50}$ is calculated as the midpoint of a sigmoid curve fitted to the correlation of normalized ThT fluorescence and inhibitor concentration. Compounds of the current invention inhibit aggregation of VQIINK (SEQ ID NO: 1; PEPTIDE ID NO: 192). The results are reported in Table 8.

TABLE 8

VQIINK Inhibition

| PEP ID NO | Peptide | IC50 (μm) |
|---|---|---|
| 335 | lkiyihy | 0.17 |
| 388 | welkvrw | 0.26 |
| 321 | lkiuihy | 0.26 |
| 307 | wrlkbrw | 0.35 |
| 286 | wrbkvrw | 0.41 |
| 294 | wnlkvrw | 0.41 |
| 354 | lkieihy | 0.65 |
| 221 | lrlkvrww | 0.67 |
| 37 | frlkirw | 0.69 |
| 100 | wkvkiqyh | 0.75 |
| 231 | frlkvrww | 0.76 |
| 244 | lkirizy | 0.76 |
| 316 | leirihy | 0.77 |
| 393 | wrbkbrw | 0.77 |
| 238 | wrlrvrww | 0.79 |
| 115 | fririhhw | 0.82 |
| 287 | lkuruhy | 0.87 |
| 210 | lrlkvrwl | 0.93 |
| 2 | wkvqvrlw | 0.94 |
| 300 | hyhirikl | 0.96 |
| 273 | wqlkvrw | 0.97 |
| 135 | felklrwh | 1.03 |
| 324 | lkiriey | 1.05 |
| 111 | wlrvqvkw | 1.08 |
| 138 | fhirirhw | 1.1 |
| 203 | ukirihy | 1.12 |
| 6 | fklklwwf | 1.15 |
| 157 | leikirhw | 1.15 |
| 437 | fhihikfh | 1.16 |
| 412 | feirlwhh | 1.17 |
| 413 | fklklrw | 1.2 |
| 105 | wriwiryw | 1.2 |
| 224 | rlkvrwww | 1.21 |
| 414 | lkirirfh | 1.24 |
| 416 | wlrvqvklw | 1.25 |
| 4 | frlkvrwf | 1.26 |
| 134 | felhikwh | 1.29 |
| 95 | wkvnvrlw | 1.29 |
| 48 | fklklww | 1.3 |
| 130 | fkirikwh | 1.3 |
| 103 | wrlriww | 1.34 |

TABLE 8-continued

VQIINK Inhibition

| PEP ID NO | Peptide | IC50 (µm) |
|---|---|---|
| 8 | wrfhihfy | 1.35 |
| 197 | wrlkvrwl | 1.37 |
| 447 | lefelkyw | 1.38 |
| 352 | wrlnvnw | 1.38 |
| 423 | frlriww | 1.4 |
| 129 | fkielhwh | 1.41 |
| 223 | lkilihyh | 1.41 |
| 271 | lkiriay | 1.41 |
| 308 | wrlkurw | 1.41 |
| 270 | frlrihw | 1.44 |
| 14 | wklklwww | 1.44 |
| 208 | lkirilyh | 1.46 |
| 61 | frikirw | 1.47 |
| 441 | lrvqvrl | 1.48 |
| 194 | lkiriryh | 1.49 |
| 279 | lkurihy | 1.5 |
| 121 | friklkwh | 1.52 |
| 92 | wkvwvryw | 1.53 |
| 214 | lkirifyh | 1.53 |
| 275 | wrlkvrwe | 1.54 |
| 200 | wrlrlrw | 1.54 |
| 35 | fkiklkw | 1.55 |
| 422 | ldlrfkly | 1.55 |
| 155 | lkiriehy | 1.57 |
| 133 | felrlhwh | 1.57 |
| 195 | wwrvklrw | 1.57 |
| 12 | wklwlrww | 1.58 |
| 242 | mrlrihw | 1.58 |
| 15 | fwlklrwf | 1.63 |
| 226 | wrfkvrw | 1.66 |
| 230 | wrlkvrwr | 1.7 |
| 366 | lairihy | 1.71 |
| 428 | wrlwihw | 1.73 |
| 337 | wrirrw | 1.73 |
| 385 | wrukurw | 1.73 |
| 110 | wfkiklel | 1.74 |
| 16 | wrlriwww | 1.75 |
| 318 | lkiriheh | 1.75 |
| 13 | wklklrww | 1.76 |
| 429 | lkleirwh | 1.76 |
| 127 | fkihikhy | 1.77 |
| 265 | hrlkvrww | 1.77 |
| 430 | feirlhhw | 1.78 |
| 427 | fhleirhw | 1.79 |
| 426 | frlklrfh | 1.8 |
| 58 | frlrihwf | 1.81 |
| 240 | lkirihlh | 1.81 |
| 30 | wwlrihww | 1.83 |
| 152 | lririrfh | 1.84 |
| 20 | wrlrihww | 1.88 |
| 206 | lkiriwyh | 1.89 |
| 222 | wrlkvrwh | 1.92 |
| 91 | wklwlrw | 1.95 |
| 215 | wrfkfrw | 1.95 |
| 233 | lkikihy | 1.96 |
| 3 | wrlkvrww | 1.97 |
| 213 | hrlkvrwh | 1.97 |
| 309 | lairihyh | 1.98 |
| 349 | wrlriew | 1.98 |
| 433 | wwlklrw | 1.99 |
| 147 | lkirihyh | 1.99 |
| 139 | fhirlewh | 2.01 |
| 113 | fririhhf | 2.02 |
| 267 | lkiruhy | 2.07 |
| 158 | lrieiewh | 2.1 |
| 258 | wrukvrw | 2.1 |
| 425 | wwlrihw | 2.11 |
| 424 | whvkfelf | 2.12 |
| 280 | wrlqvrw | 2.12 |
| 320 | lkizihy | 2.13 |
| 281 | wrlkvqw | 2.15 |
| 93 | wkvwvrgw | 2.17 |
| 57 | fklklrwf | 2.2 |
| 348 | wrleihw | 2.2 |
| 89 | wkvqvrw | 2.21 |
| 101 | wrlrihw | 2.23 |

TABLE 8-continued

VQIINK Inhibition

| PEP ID NO | Peptide | IC50 (μm) |
|---|---|---|
| 263 | wrlkfrw | 2.23 |
| 409 | lkiaihyh | 2.26 |
| 319 | wqlkvqw | 2.27 |
| 18 | frlriwwf | 2.29 |
| 282 | urlkvrw | 2.29 |
| 293 | brlkvrw | 2.31 |
| 60 | fkikikw | 2.35 |
| 148 | lkihirhw | 2.38 |
| 339 | wrldvrw | 2.42 |
| 289 | wrlkvrw | 2.45 |
| 47 | friklrw | 2.49 |
| 9 | fklwlrwf | 2.52 |
| 218 | wrlkvrwf | 2.53 |
| 4 | frlkvrwf | 2.57 |
| 56 | frirlrw | 2.58 |
| 452 | wrlrimw | 2.61 |
| 132 | fklkikw | 2.66 |
| 421 | lrikirfh | 2.69 |
| 382 | wqlqvrw | 2.74 |
| 5 | lelkikfw | 2.78 |
| 305 | wtlrihw | 2.82 |
| 285 | lkiqihy | 2.82 |
| 272 | wrlriaw | 2.86 |
| 434 | lklhlhfh | 2.87 |
| 314 | wrlritw | 2.89 |
| 194 | lkiriryh | 2.92 |
| 291 | lkirihyr | 3.02 |
| 345 | walrihw | 3.12 |
| 330 | wrltihw | 3.16 |
| 328 | wrlkvdw | 3.21 |
| 257 | walkvrw | 3.32 |
| 199 | lkvrwwwr | 3.34 |
| 239 | lririhyh | 3.34 |
| 304 | wmlrihw | 3.34 |
| 353 | lkirihye | 3.39 |
| 322 | welrihw | 3.46 |
| 372 | wnlkvnw | 3.5 |
| 248 | wrlkvaw | 3.57 |

TABLE 8-continued

VQIINK Inhibition

| PEP ID NO | Peptide | IC50 (μm) |
|---|---|---|
| 81 | wwlklrww | 3.79 |
| 269 | lkirihya | 3.83 |
| 331 | wdlkvrw | 3.87 |
| 301 | wrlavrw | 3.89 |
| 83 | wlkivw | 3.93 |
| 417 | frlwihw | 4.01 |
| 418 | fkieieyh | 4.03 |
| 196 | vrwwklrw | 4.06 |
| 11 | wrlwihww | 4.07 |
| 53 | ilkivw | 4.13 |
| 201 | kvrwwlrw | 4.35 |
| 384 | wrlkvew | 4.36 |
| 276 | wrtkvrw | 4.41 |
| 7 | fwlrihwf | 4.42 |
| 225 | rrlkvrww | 4.44 |
| 419 | vkvwgrlw | 4.51 |
| 336 | lkiaihy | 4.77 |
| 283 | tkirihy | 4.77 |
| 78 | tlkivw | 5.02 |
| 371 | yrlkvrw | 5.12 |
| 303 | lkiriayh | 5.21 |
| 333 | lkiriha | 5.3 |
| 90 | wklklrw | 5.33 |
| 298 | rlkvrww | 5.35 |
| 167 | tiklvw | 5.37 |
| 379 | lkirihah | 5.54 |
| 227 | rkirihyh | 5.59 |
| 22 | rtlkivwr | 5.65 |
| 254 | mrlkvrw | 5.67 |
| 284 | wrlkvrew | 5.77 |
| 332 | wrlrifw | 6.33 |
| 220 | wrrkvrww | 6.43 |
| 325 | wrlaihw | 6.49 |
| 350 | wrlmihw | 6.58 |
| 312 | arlrihw | 6.61 |
| 381 | lkvrww | 6.63 |
| 270 | frlrihw | 6.7 |
| 86 | elkivw | 6.85 |

TABLE 8-continued

VQIINK Inhibition

| PEP ID NO | Peptide | IC50 (μm) |
|---|---|---|
| 368 | klkwlw | 6.93 |
| 52 | klkivw | 6.95 |
| 278 | wrlkvrrw | 7.04 |
| 370 | kirihyhl | 7.25 |
| 262 | wrlriht | 7.32 |
| 408 | wrekvrww | 7.34 |
| 274 | lkirihrh | 7.35 |
| 453 | wrlrihm | 7.39 |
| 389 | lkirieyh | 7.95 |
| 78 | tlkivw | 7.98 |
| 391 | wflrihw | 8.18 |
| 255 | wrlktrw | 8.61 |
| 386 | irihyhlk | 8.69 |
| 360 | akirihyh | 8.93 |
| 260 | wrlrmhw | 8.93 |
| 204 | vrwwwrlk | 9.47 |
| 347 | wrlriha | 9.75 |
| 398 | lkarihyh | 10 |
| 341 | lkirrhyh | 10.5 |
| 26 | rikirw | 10.79 |
| 23 | rlkirw | 10.94 |
| 397 | welkvew | 11 |
| 246 | wrmrihw | 11.7 |
| 290 | rrlrihw | 12.12 |
| 392 | wrtktrw | 13.06 |
| 378 | wrlkhrw | 13.52 |
| 395 | erlrihw | 13.56 |
| 396 | wrlrihe | 14.47 |
| 364 | kvrwwwrl | 15.22 |
| 245 | lkirihy | 17.57 |
| 355 | wrarihw | 19.12 |
| 359 | erlkvrww | 20.44 |
| 323 | wrlkvra | 20.53 |
| 405 | lkrrihyh | 31.77 |

Example 9

Seeding Inhibition Assay (Pre-Capping)

To determine whether pre-capping Tau fibrils with inhibitors reduces the aggregation seeding potential of these fibrils, inhibitors were titrated against a fixed fibril concentration prior to seeding biosensor cell assays. Tau40P301L (SEQ ID NO: 25) fibrils were prepared as in Example 7, then diluted to 2.5 μM in OptiMEM. 20 μL of inhibitors dissolved in OptiMEM, were added to 20 μL of 2.5 μM Tau40P301L (SEQ ID NO: 25) fibrils at inhibitor concentrations 20-fold greater than the final concentration introduced into the biosensor-cell test wells. The resultant 1.25 μM fibril solutions were incubated with inhibitors for 16 h at room temperature prior to addition of Lipofectamine 2000 working solution. 40 μL of Lipofectamine 2000 working solution, prepared by diluting 1 volume of Lipofectamine 2000 transfection reagent into 19 volumes of OptiMEM. was incubated with the pre-capped fibrils for 20 minutes. 10 μL of these pre-capped fibril: Lipofectamine solutions were added to 90 μL of biosensor cells to achieve the final reported inhibitor concentration. This method was adapted from that described by P. M. Seidler et al. Nat Chem. February 2018. 10(2):170-176. 2018. The peptides of the invention inhibit fibril seeding at a concentration below 20 μM. The results are reported in Table 9.

TABLE 9

Seeding Inhibition

| PEP ID NO | Peptide | 50% inhibition at 16 μM |
|---|---|---|
| 463 | RRRRRRRRR-GGSGG-wrlkvrww | yes |
| 3 | wrlkvrww | yes |

Example 10

Identification of Aggregation Inhibitors of Tau40 Utilizing a Competition Assay

The following describes the experimental method used to evaluate the competition $IC_{50}$ of an interaction with a test compound and its interaction with Tau amyloid. This assay measures binding of a peptide inhibitor probe to tau amyloid aggregates, allowing identification of molecules that displace this probe by binding tau at the same aggregation-driving sites. His-Tau40P301L fibrils are prepared similar to that described in the Examples above. His-Tau40P301L at 100 μM in the presence of DTT [5 mM], heparin sulfate [20 μM], and buffer [pH 6.8, MES (20 mM, NaCl (100 mM)] is shaken at 37° C. with 1400 rpm using a microfuge tube shaker. A solution of probe peptide, such as one conjugated at the N-terminal amine of a peptide inhibitor with a flouresence tracer [e.g. TAMRA5-PEG2] is prepared as described above. An assay buffer is prepared [pH6.8, MES (50 mM), NaCl (125 mM) and TWEEN-20 (0.01% w/v)]. Probe peptide [10 nM] is added to His-Tau40P301L (SEQ ID NO: 27) [1-2.5 μM], and the interaction between the two is measured using fluorescence polarization in a Tecan ULTRA instrument at excitation wavelength of 535 and emission wavelength of 585. After addition of potential competitive binding compounds to the fibril-probe mixture, measurement with fluoresence polarization can be used to quantitate the amount of free probe relative to probe bound to the fibril relating to the amount of probe displaced by the test compound.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

```
Sequence Listings
                                          (SEQ ID NO: 24)
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L
```

What is claimed:
1. A peptide comprising:
(a)
(i) an amino acid sequence of formula IX:

(IX)
(PEPTIDE ID NO: 175)
Xaa54-Xaa55-Xaa56-Xaa57-Xaa58-D-Trp wherein
Xaa54 is selected from D-Trp, D-Glu, D-Thr, D-Lys and D-Arg;
Xaa55 is selected from D-Arg, D-Ile, and D-Leu;
Xaa56 is selected from D-Leu, D-Lys and D-Arg;
Xaa57 is selected from D-Arg, D-Val, D-Ile and D-Leu; and
Xaa58 is selected from D-Lys, D-Arg, and D-Val; or
(ii) a variant of (i) in which one amino acid from Formula IX is replaced with a conservative substitution or a synthetic, or chemically modified cationic amino acid residue;
(b) a C-terminal acid or amide of (a); or
(c) an N-acetyl derivative of (a) or (b);
or a pharmaceutically acceptable salt thereof,
wherein the peptide inhibits aggregation of tau protein, and
wherein the sequence is not PEPTIDE ID NO: 75.

2. A peptide of claim 1 comprising:
(a) an amino acid sequence of formula IX:

(IX)
(PEPTIDE ID NO: 175)
Xaa54-Xaa55-Xaa56-Xaa57-Xaa58-D-Trp wherein
Xaa54 is selected from D-Trp, D-Glu, D-Thr, D-Lys and D-Arg;
Xaa55 is selected from D-Arg, D-Ile, and D-Leu;
Xaa56 is selected from D-Leu, D-Lys and D-Arg;
Xaa57 is selected from D-Arg, D-Val, D-Ile and D-Leu; and
Xaa58 is selected from D-Lys, D-Arg, and D-Val; or
(b) a C-terminal acid or amide of (a); or
(c) an N-acetyl derivative of (a) or (b);
or a pharmaceutically acceptable salt thereof.

3. A composition of matter comprising the peptide of claim 2 or the C-terminal acid or amide thereof; or the N-acetyl derivative thereof; or the pharmaceutically acceptable salt thereof; and a pharmaceutically acceptable carrier.

4. A peptide according to claim 1 that comprises the peptide of formula IX or the variant in which one amino acid is replaced with a conservative substitution; or the C-terminal acid or amide thereof; or the N-acetyl derivative thereof; or the pharmaceutically acceptable salt thereof.

5. The peptide of claim 1, further comprising a duration enhancing moiety; or the C-terminal acid or amide thereof; or the N-acetyl derivative thereof; or the pharmaceutically acceptable salt thereof.

6. An isolated peptide of claim 1 or the C-terminal acid or amide thereof; or the N-acetyl derivative thereof; or the pharmaceutically acceptable salt thereof.

7. A composition of matter comprising the peptide of claim 1 or the C-terminal acid or amide thereof; or the N-acetyl derivative thereof; or the pharmaceutically acceptable salt thereof; and a pharmaceutically acceptable carrier.

8. The composition according to claim 7 that includes a peptide-stabilizing excipient.

9. A method of affecting VQIINK- (PEPTIDE ID NO: 192; SEQ ID NO: 1) related aggregation comprising treatment with a peptide of claim 1 or the C-terminal acid or amide thereof; or the N-acetyl derivative thereof; or the pharmaceutically acceptable salt thereof.

10. A method of treating aggregation of tau protein that comprises contacting the tau protein with the peptide of claim 1 or the C-terminal acid or amide thereof; or the N-acetyl derivative thereof; or the pharmaceutically acceptable salt thereof.

11. A method of treating a disease or condition to inhibit disease progression or provide palliative treatment; the disease selected from tauopathies; Alzheimer's disease; Parkinson's disease (a-synuclein amyloidosis); amyotrophic lateral sclerosis; type II diabetes (islet amyloid polypeptide (IAPP) amyloidosis); lysozyme amyloidosis; familial amyloidosis, senile amyloidosis; variant Creutzfeldt-Jakob disease (vCJD), Gerstmann-Straussler-Scheinker syndrome (GSS); cardiac amyloidosis; human immunodeficiency virus (HIV) sexual transmission associated with the semen-derived enhancer of viral infection (SEVI) form of prostate activating protein of semen, and antibody light chain amyloidosis affecting kidney function, in a patient in need of such treatment, the method comprising administering to the patient:
(A) a peptide of claim 1 or the C-terminal acid or amide thereof; or the N-acetyl derivative thereof; or the pharmaceutically acceptable salt thereof; or
(B) a composition comprising (A) and a pharmaceutically acceptable carrier or peptide-stabilizing excipient;
in an amount effective to inhibit disease progression or provide palliative treatment.

12. A method of using a peptide of claim 1 in screening for candidate compounds which inhibit the activity of the peptide in its interaction with tau aggregates, the method comprising contacting the peptide and the tau aggregates in the presence and absence of a test compound; and screening for candidate compounds which inhibit the activity of the peptide by measuring free peptide in the presence and in the absence of the test compound.

13. The peptide according to claim 1 comprising an amino acid sequence selected from wikirw (PEPTIDE ID NO: 21), rikirw (PEPTIDE ID NO: 26), and rlkirw (PEPTIDE ID NO: 23); or C-terminal acids or amides, or N-acetyl derivatives thereof; or pharmaceutically acceptable salts thereof.

14. The peptide according to claim 1, wherein the C-terminal amino acid of the peptide is the D-Trp of Formula IX.

15. The peptide of claim 1, further comprising a cell penetrating peptide (CPP); or the C-terminal acid or amide thereof; or the N-acetyl derivative thereof; or the pharmaceutically acceptable salt thereof.

16. The peptide of claim 15 wherein the CPP modified peptide is not (PEPTIDE ID NO: 454)
RRRRRRRRR-GGSGG-rlkvrw.

17. The peptide of claim 15, further comprising a linker of the sequence -GGSGG- (PEPTIDE ID NO: 179, SEQ ID NO: 15) between the CPP and the amino acid sequence of Formula IX; or the C-terminal acid or amide thereof; or the N-acetyl derivative thereof; or the pharmaceutically acceptable salt thereof.

18. The peptide of claim 15 selected from RRRRRRRRR-GGSGG-tlkivw (PEPTIDE ID NO: 472); RRRRRRRRR-GGSGG-wrlkvrww (PEPTIDE ID NO:

465); RRRRRRRRR-GGSGG-wrlkvrww (PEPTIDE ID NO: 463); or the C-terminal acid or amide thereof; or the N-acetyl derivative thereof; or the pharmaceutically acceptable salt thereof.

19. An assay comprising:

contacting a tau aggregate with a probe comprising a peptide of claim 1, under conditions in which the probe binds to the tau aggregate;

adding a test compound; and detecting or measuring a level of probe bound to the tau aggregate or displaced from the tau aggregate.

20. The assay according to claim 19, wherein the probe further comprises a detectable label.

21. The assay according to claim 19 that comprises measuring probe bound to tau aggregate in the presence and in the absence of the test compound; and identifying a difference in probe bound to tau aggregate in the presence of the test compound, compared to probe bound in the absence of the test compound.

22. The assay according to claim 21, further comprising identifying the test compound as an agent that inhibits tau aggregation, from the difference in binding.

23. A method of identifying a compound which binds to aggregated protein and displaces or blocks binding of a probe comprising a peptide that interacts with said aggregated protein comprising the steps:

i. adding a probe peptide to an aggregated form of a protein, said probe comprising a peptide of claim 1; and ii. identifying a compound that displaces or blocks binding of said probe peptide.

24. The method of claim 23 wherein the aggregated protein is tau, transthyretin, p53, or amylin.

25. The method of claim 24 wherein the aggregated protein is tau.

26. A method of inhibiting Tau protein seeding, the method comprising contacting a cell that contains Tau protein with the peptide of claim 1.

27. The method of claim 26, wherein the contacting comprises administering a composition comprising the peptide to a subject, wherein inhibiting Tau protein seeding inhibits development or progression of a tauopathy in the subject.

28. The peptide according to claim 1, further comprising a cell penetrating peptide (CPP), wherein the CPP comprises a poly-arginine sequence of 5-16 arginine residues; or C-terminal acids or amides, or N-acetyl derivatives thereof; or pharmaceutically acceptable salts thereof.

29. The peptide according to claim 28, further comprising a linker comprised of the sequence -GG- or -GGSGG- (SEQ ID NO: 179) linking the amino acid having the sequence of Formula IX with the CPP.

30. A peptide of claim 1 comprising
(a) an amino acid sequence selected from

| | |
|---|---|
| wrlrihw, | (PEPTIDE ID NO: 101) |
| rlkirihy, | (PEPTIDE ID NO: 451) |
| wrlrimw, | (PEPTIDE ID NO: 452) |
| wrlrihm, | (PEPTIDE ID NO: 453) |
| lkirihyl, | (PEPTIDE ID NO: 193) |
| lkiriryh, | (PEPTIDE ID NO: 194) |
| wwrvklrw, | (PEPTIDE ID NO: 195) |
| lkirihyh, | (PEPTIDE ID NO: 147) |
| vrwwklrw, | (PEPTIDE ID NO: 196) |
| wrlkvrwl, | (PEPTIDE ID NO: 197) |
| wlkirihy, | (PEPTIDE ID NO: 198) |
| wkvwvryw, | (PEPTIDE ID NO: 92) |
| lkvrwwwr, | (PEPTIDE ID NO: 199) |
| wrlrlrw, | (PEPTIDE ID NO: 200) |
| wikirw | (PEPTIDE ID NO: 21) |
| kvrwwlrw, | (PEPTIDE ID NO: 201) |
| lwrlkvrw, | (PEPTIDE ID NO: 202) |
| ukirihy, | (PEPTIDE ID NO: 203) |
| vrwwwrlk, and | (PEPTIDE ID NO: 204) |
| wrlkvrww, | (PEPTIDE ID NO: 3) | or (b) a C-terminal acid or amide of (a); or
(c) an N-acetyl derivative of (a) or (b); or
a pharmaceutically acceptable salt thereof.

\* \* \* \* \*

SEQUENCE LISTING

```
<160> NUMBER OF SEQ ID NOS: 481

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Phe, D-Arg, D-Leu, D-Tyr, D-Pro, D-Trp
      or is absent
<220> FEATURE:
<221> NAME/KEY: MISC_FEATURE
<222> LOCATION: (2)..(2)
<223> OTHER INFORMATION: Xaa is D-Arg, D-His, D-Thr, D-Gln, D-Glu,
      D-Ala, D-Ile, D-Asp, D-Leu, D-Phe, D-Pro, D-Trp or D-Lys
<220> FEATURE:
<221> NAME/KEY: MISC_FEATURE
<222> LOCATION: (3)..(3)
<223> OTHER INFORMATION: Xaa is D-Leu, D-Val, D-Ile, D-Phe, D-Lys, D-Arg
      or D-Trp
<220> FEATURE:
<221> NAME/KEY: MISC_FEATURE
<222> LOCATION: (4)..(4)
<223> OTHER INFORMATION: Xaa is D-Phe, D-Leu, D-Glu, D-Gln, D-Gly,
      D-Val, D-Asp, D-Asn, D-Pro, D-His, D-Trp, D-Ile, D-Arg or D-Lys
<220> FEATURE:
<221> NAME/KEY: MISC_FEATURE
<222> LOCATION: (5)..(5)
<223> OTHER INFORMATION: Xaa is D-His, D-Ile, D-Val, D-Ala, D-Gly,
      D-Phe, D-Gln, D-Arg, D-Lys, D-Leu or D-Trp
<220> FEATURE:
<221> NAME/KEY: MISC_FEATURE
<222> LOCATION: (6)..(6)
<223> OTHER INFORMATION: Xaa is D-His, D-Lys, D-Trp, D-Gln, D-Asn,
      D-Glu, D-Leu, D-Ala, D-Val or D-Arg
<220> FEATURE:
<221> NAME/KEY: MISC_FEATURE
<222> LOCATION: (7)..(7)
<223> OTHER INFORMATION: Xaa is D-Arg, D-His, D-Leu, D-Lys, D-Glu,
```

D-Val, D-Gly, D-Tyr, D-Phe, D-Thr or D-Trp
<220> FEATURE:
<221> NAME/KEY: MISC_FEATURE
<222> LOCATION: (8)..(8)
<223> OTHER INFORMATION: Xaa is D-Arg, D-Trp, D-Leu, D-Ile, D-Val,
      D-His, D-Phe, D-Tyr or is absent

<400> SEQUENCE: 1

Xaa Xaa Xaa Xaa Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Gln
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Leu
<220> FEATURE:
<221> NAME/KEY: MISC_FEATURE
<222> LOCATION: (8)..(8)
<223> OTHER INFORMATION: D-Trp

<400> SEQUENCE: 2

Trp Lys Val Gln Val Arg Leu Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)

```
<223> OTHER INFORMATION: D-Lys
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 3

Trp Arg Leu Lys Val Arg Trp Trp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 4

Phe Arg Leu Lys Val Arg Trp Phe
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
```

```
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MISC_FEATURE
<222> LOCATION: (8)..(8)
<223> OTHER INFORMATION: D-Trp

<400> SEQUENCE: 5

Leu Glu Leu Lys Ile Lys Phe Trp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 6

Phe Lys Leu Lys Leu Trp Trp Phe
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 7

Phe Trp Leu Arg Ile His Trp Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
```

<223> OTHER INFORMATION: D-Phe
<220> FEATURE:
<221> NAME/KEY: MISC_FEATURE
<222> LOCATION: (8)..(8)
<223> OTHER INFORMATION: D-Tyr

<400> SEQUENCE: 8

Trp Arg Phe His Ile His Phe Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 9

Phe Lys Leu Trp Leu Arg Trp Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp

```
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 10

Phe Arg Leu Trp Ile His Trp Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 11

Trp Arg Leu Trp Ile His Trp Trp
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
```

```
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 12

Trp Lys Leu Trp Leu Arg Trp Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 13

Trp Lys Leu Lys Leu Arg Trp Trp
1               5
```

```
<210> SEQ ID NO 14
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 14

Trp Lys Leu Lys Leu Trp Trp Trp
 1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
```

```
<220> FEATURE:
<221> NAME/KEY: MISC_FEATURE
<222> LOCATION: (8)..(8)
<223> OTHER INFORMATION: D-Phe

<400> SEQUENCE: 15

Phe Trp Leu Lys Leu Arg Trp Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 16

Trp Arg Leu Arg Ile Trp Trp Trp
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp
<220> FEATURE:
```

```
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 17

Arg Trp Arg Trp Arg Trp
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 18

Phe Arg Leu Arg Ile Trp Trp Phe
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
```

```
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 19

Trp His Leu Arg Ile Arg Trp
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 20

Trp Arg Leu Arg Ile His Trp Trp
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
```

```
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 21

Trp Ile Lys Ile Arg Trp
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Thr
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Arg

<400> SEQUENCE: 22

Arg Thr Leu Lys Ile Val Trp Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
```

```
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 23

Arg Leu Lys Ile Arg Trp
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 24

Arg Ile Lys Leu Arg Trp
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Ile
<220> FEATURE:
```

```
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Arg

<400> SEQUENCE: 25

Trp Ile Lys Ile Arg Arg
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 26

Arg Ile Lys Ile Arg Trp
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
```

```
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 27

Arg Leu Arg Ile Arg Trp
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Trp

<400> SEQUENCE: 28

Lys Ile Lys Leu Lys Trp
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
```

```
<223> OTHER INFORMATION: D-Trp
<220> FEATURE:
<221> NAME/KEY: MISC_FEATURE
<222> LOCATION: (6)..(6)
<223> OTHER INFORMATION: D-Arg

<400> SEQUENCE: 29

Trp Ile Lys Ile Trp Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 30

Trp Trp Leu Arg Ile His Trp Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
```

```
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg

<400> SEQUENCE: 31

Trp Ile Lys Ile Val Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Thr
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (7)..(7)
<223> OTHER INFORMATION: D-Trp

<400> SEQUENCE: 32

Arg Thr Leu Lys Ile Val Trp
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
```

```
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp

<400> SEQUENCE: 33

Pro Arg Ile Arg Leu His Trp
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Trp

<400> SEQUENCE: 34

Lys Leu Lys Ile Lys Trp
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
```

```
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp

<400> SEQUENCE: 35

Phe Lys Ile Lys Leu Lys Trp
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 36

Arg Leu Arg Ile His Trp
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
```

```
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 37

Phe Arg Leu Lys Ile Arg Trp
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 38

Arg Ile Arg Leu Arg Trp
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Arg
```

```
<220> FEATURE:
<221> NAME/KEY: MISC_FEATURE
<222> LOCATION: (6)..(6)
<223> OTHER INFORMATION: D-Trp

<400> SEQUENCE: 39

Lys Leu Lys Leu Arg Trp
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Trp

<400> SEQUENCE: 40

Trp Arg Leu Arg Trp Trp
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp
```

```
<400> SEQUENCE: 41

Arg Ile Arg Leu His Trp
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 42

Trp Arg Leu Arg Val Trp
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Arg

<400> SEQUENCE: 43
```

Trp Trp Arg Phe His Trp Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Trp
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 44

Arg Leu Trp Val Arg Trp
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 45

Thr Leu Lys Ile Arg Trp
1               5

```
<210> SEQ ID NO 46
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 46

Trp Leu Lys Val Arg Trp
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 47

Phe Arg Ile Lys Leu Arg Trp
1               5

<210> SEQ ID NO 48
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp

<400> SEQUENCE: 48

Phe Lys Leu Lys Leu Trp Trp
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 49

Arg Leu Arg Ile Val Trp
1               5

<210> SEQ ID NO 50
<211> LENGTH: 6
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 50

Arg Ile Arg Trp Arg Trp
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 51

Phe Lys Leu Trp Leu Arg Trp
1               5

<210> SEQ ID NO 52
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 52

Lys Leu Lys Ile Val Trp
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 53

Ile Leu Lys Ile Val Trp
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 54

Thr Ile Lys Ile Val Trp
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Pro
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (7)..(7)
<223> OTHER INFORMATION: D-Trp

<400> SEQUENCE: 55

Arg Pro Leu Lys Ile Val Trp
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 56

Phe Arg Ile Arg Leu Arg Trp
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 57

Phe Lys Leu Lys Leu Arg Trp Phe
1               5

<210> SEQ ID NO 58
<211> LENGTH: 8
```

-continued

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Phe

<400> SEQUENCE: 58

Phe Arg Leu Arg Ile His Trp Phe
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 59

Pro Leu Lys Ile Val Trp
1               5
```

```
<210> SEQ ID NO 60
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 60

Phe Lys Ile Lys Ile Lys Trp
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
```

```
<223> OTHER INFORMATION: D-Trp

<400> SEQUENCE: 61

Phe Arg Ile Lys Ile Arg Trp
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Val
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Thr

<400> SEQUENCE: 62

Trp Val Ile Lys Leu Thr
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 63

Pro Leu Arg Ile Val Trp
```

```
<210> SEQ ID NO 64
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 64

Thr Leu Lys Ile His Trp
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Glu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 65

Arg Ile Glu Leu His Trp
1               5

<210> SEQ ID NO 66
<211> LENGTH: 6
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Trp

<400> SEQUENCE: 66

Lys Ile Lys Ile Lys Trp
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg

<400> SEQUENCE: 67

Thr Leu Lys Ile Val Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: D-Gln
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 68

Gln Leu Arg Ile His Trp
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ile
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Tyr
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-His

<400> SEQUENCE: 69

Ile Arg Leu Tyr Trp His
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
```

```
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 70

Phe Arg Leu Arg Ile Arg Trp
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 71

Arg Ile Ala Leu His Trp
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
```

```
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 72

Trp Leu Lys Ile Arg Trp
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Leu

<400> SEQUENCE: 73

Thr Trp Arg Leu Val Leu
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Glu
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
```

```
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

<400> SEQUENCE: 74

Glu Ile Arg Leu His Trp
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 75

Arg Ile Arg Ile Arg Trp
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
```

```
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
<222> LOCATION: (6)..(6)
<223> OTHER INFORMATION: D-Trp

<400> SEQUENCE: 76

Thr Leu Lys Ile Ala Trp
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Trp
<220> FEATURE:
<221> NAME/KEY: MISC_FEATURE
<222> LOCATION: (6)..(6)
<223> OTHER INFORMATION: D-Trp

<400> SEQUENCE: 77

Thr Leu Lys Ile Trp Trp
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
```

```
<222> LOCATION: (6)..(6)
<223> OTHER INFORMATION: D-Trp

<400> SEQUENCE: 78

Thr Leu Lys Ile Val Trp
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 79

Trp Lys Leu Val Val Trp
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Trp

<400> SEQUENCE: 80
```

Lys Leu Lys Leu Lys Trp
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Trp

<400> SEQUENCE: 81

Trp Trp Leu Lys Leu Arg Trp Trp
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp

```
<400> SEQUENCE: 82

Ala Ile Arg Leu His Trp
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 83

Trp Leu Lys Ile Val Trp
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 84

Thr Leu Lys Leu Val Trp
1               5
```

```
<210> SEQ ID NO 85
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 85

Trp Ile Lys Leu Arg Trp
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Glu
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 86

Glu Leu Lys Ile Val Trp
1               5

<210> SEQ ID NO 87
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Glu
<220> FEATURE:
<221> NAME/KEY: MISC_FEATURE
<222> LOCATION: (6)..(6)
<223> OTHER INFORMATION: D-Trp

<400> SEQUENCE: 87

Thr Leu Lys Ile Glu Trp
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Phe

<400> SEQUENCE: 88

Thr Leu Lys Ile Val Phe
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Gln
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 89

Trp Lys Val Gln Val Arg Trp
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 90

Trp Lys Leu Lys Leu Arg Trp
1               5

<210> SEQ ID NO 91
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Arp

<400> SEQUENCE: 91

Trp Lys Leu Trp Leu Arg Trp
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Trp

<400> SEQUENCE: 92

Trp Lys Val Trp Val Arg Tyr Trp
1               5
```

```
<210> SEQ ID NO 93
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Gly
<220> FEATURE:
<221> NAME/KEY: MISC_FEATURE
<222> LOCATION: (8)..(8)
<223> OTHER INFORMATION: D-Trp

<400> SEQUENCE: 93

Trp Lys Val Trp Val Arg Gly Trp
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
```

```
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 94

Trp Lys Val Lys Phe Gln His Trp
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Asn
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Leu
<220> FEATURE:
<221> NAME/KEY: MISC_FEATURE
<222> LOCATION: (8)..(8)
<223> OTHER INFORMATION: D-Trp

<400> SEQUENCE: 95

Trp Lys Val Asn Val Arg Leu Trp
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
```

```
<223> OTHER INFORMATION: D-Trp
<220> FEATURE:
<221> NAME/KEY: MISC_FEATURE
<222> LOCATION: (5)..(5)
<223> OTHER INFORMATION: D-Gly
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (8)..(8)
<223> OTHER INFORMATION: D-Trp

<400> SEQUENCE: 96

Trp Lys Val Trp Gly Lys Val Trp
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Pro
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Trp

<400> SEQUENCE: 97

Trp Lys Val Pro Val Arg Tyr Trp
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
```

```
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Gly
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (8)..(8)
<223> OTHER INFORMATION: D-Trp

<400> SEQUENCE: 98

Trp Lys Val Trp Gly Arg Val Trp
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 99

Trp Lys Val His Ile Gln His Trp
1               5
```

```
<210> SEQ ID NO 100
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-His

<400> SEQUENCE: 100

Trp Lys Val Lys Ile Gln Tyr His
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
```

<223> OTHER INFORMATION: D-Trp

<400> SEQUENCE: 101

Trp Arg Leu Arg Ile His Trp
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Gln
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp

<400> SEQUENCE: 102

Trp Arg Val Gln Val Arg Trp
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Trp

```
<220> FEATURE:
<221> NAME/KEY: MISC_FEATURE
<222> LOCATION: (7)..(7)
<223> OTHER INFORMATION: D-Trp

<400> SEQUENCE: 103

Trp Arg Leu Arg Ile Trp Trp
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Trp

<400> SEQUENCE: 104

Trp Arg Ile Arg Leu Arg Tyr Trp
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Trp
<220> FEATURE:
```

```
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Trp

<400> SEQUENCE: 105

Trp Arg Ile Trp Ile Arg Tyr Trp
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 106

Trp Arg Val His Phe Glu His Trp
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
```

```
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Val

<400> SEQUENCE: 107

Trp His Val Arg Ile Arg His Val
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Asn
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Leu

<400> SEQUENCE: 108

Trp His Val Arg Leu Asn His Leu
1               5

<210> SEQ ID NO 109
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 109

Trp His Leu Arg Leu Arg His Trp
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Phe
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (7)..(7)
<223> OTHER INFORMATION: D-Glu
<220> FEATURE:
```

```
<221> NAME/KEY: MISC_FEATURE
<222> LOCATION: (8)..(8)
<223> OTHER INFORMATION: D-Leu

<400> SEQUENCE: 110

Trp Phe Lys Ile Lys Leu Glu Leu
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Gln
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (7)..(7)
<223> OTHER INFORMATION: D-Lys
<220> FEATURE:
<221> NAME/KEY: MISC_FEATURE
<222> LOCATION: (8)..(8)
<223> OTHER INFORMATION: D-Trp

<400> SEQUENCE: 111

Trp Leu Arg Val Gln Val Lys Trp
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Asp
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
```

```
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Trp

<400> SEQUENCE: 112

Trp Asp Leu Arg Leu Gln Tyr Trp
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Phe

<400> SEQUENCE: 113

Phe Arg Ile Arg Ile His His Phe
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
```

```
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 114

Phe Arg Ile Arg Ile Lys His Tyr
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 115

Phe Arg Ile Arg Ile His His Trp
1               5

<210> SEQ ID NO 116
<211> LENGTH: 8
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 116

Phe Arg Leu Lys Leu Arg His Trp
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
```

```
<222> LOCATION: (8)..(8)
<223> OTHER INFORMATION: D-Trp

<400> SEQUENCE: 117

Phe Arg Leu Lys Ile Arg His Trp
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 118

Phe Arg Val Arg Ile Arg His Trp
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
```

```
<223> OTHER INFORMATION: D-Ile
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 119

Phe Arg Val Lys Ile Glu His Trp
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 120

Phe Arg Val Lys Ile Gln His Trp
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
```

```
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 121

Phe Arg Ile Lys Leu Lys Trp His
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 122

Phe Lys Ile Arg Ile His His Tyr
1               5

<210> SEQ ID NO 123
<211> LENGTH: 8
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 123

Phe Lys Leu Arg Leu Arg His Trp
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
```

<223> OTHER INFORMATION: D-Trp

<400> SEQUENCE: 124

Phe Lys Ile His Leu Arg His Trp
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 125

Phe Lys Leu Lys Leu Arg His Trp
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Leu

```
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 126

Phe Lys Leu His Leu Arg His Trp
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 127

Phe Lys Ile His Ile Lys His Tyr
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
```

```
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 128

Phe Lys Leu His Ile Arg His Trp
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Glu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 129

Phe Lys Ile Glu Leu His Trp His
1               5

<210> SEQ ID NO 130
<211> LENGTH: 8
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 130

Phe Lys Ile Arg Ile Lys Trp His
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr
```

<400> SEQUENCE: 131

Phe Lys Leu His Leu Lys His Tyr
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp

<400> SEQUENCE: 132

Phe Lys Leu Lys Ile Lys Trp
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-His
<220> FEATURE:

```
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 133

Phe Glu Leu Arg Leu His Trp His
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 134

Phe Glu Leu His Ile Lys Trp His
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
```

```
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 135

Phe Glu Leu Lys Leu Arg Trp His
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 136

Phe Glu Leu Arg Ile Lys His Tyr
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: D-Phe
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Glu
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 137

Phe Glu Leu Glu Ile Glu Trp His
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 138

Phe His Ile Arg Ile Arg His Trp
1               5
```

```
<210> SEQ ID NO 139
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 139

Phe His Ile Arg Leu Glu Trp His
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
```

```
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-His

<400> SEQUENCE: 140

Phe His Leu Lys Ile Arg His His
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-His

<400> SEQUENCE: 141

Phe His Ile Arg Leu Arg His His
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Gln
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
```

```
<223> OTHER INFORMATION: D-Asp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: D-Phe

<400> SEQUENCE: 142

Leu Gln Phe Asp Leu Gln Tyr Phe
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 143

Leu Lys Ile Arg Leu His His Trp
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
```

-continued

```
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 144

Leu Lys Ile Lys Leu Arg His Tyr
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 145

Leu Arg Ile Arg Ile Lys His Tyr
1               5
```

```
<210> SEQ ID NO 146
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Phe

<400> SEQUENCE: 146

Leu Arg Ile Arg Leu His His Phe
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
```

```
<223> OTHER INFORMATION: D-Tyr
<220> FEATURE:
<221> NAME/KEY: MISC_FEATURE
<222> LOCATION: (8)..(8)
<223> OTHER INFORMATION: D-His

<400> SEQUENCE: 147

Leu Lys Ile Arg Ile His Tyr His
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-His
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 148

Leu Lys Ile His Ile Arg His Trp
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-His
```

```
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 149

Leu Arg Leu His Leu Arg His Trp
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Phe

<400> SEQUENCE: 150

Leu Arg Leu Arg Ile Lys His Phe
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
```

```
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 151

Leu His Ile Lys Leu Arg Trp His
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MISC_FEATURE
<222> LOCATION: (8)..(8)
<223> OTHER INFORMATION: D-His

<400> SEQUENCE: 152

Leu Arg Ile Arg Ile Arg Phe His
1               5
```

```
<210> SEQ ID NO 153
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 153

Leu His Ile Arg Leu Arg His Trp
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
```

```
<220> FEATURE:
<221> NAME/KEY: MISC_FEATURE
<222> LOCATION: (8)..(8)
<223> OTHER INFORMATION: D-Phe

<400> SEQUENCE: 154

Leu Lys Leu Lys Ile Lys His Phe
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Tyr

<400> SEQUENCE: 155

Leu Lys Ile Arg Ile Glu His Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
```

```
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Phe

<400> SEQUENCE: 156

Leu His Ile Lys Leu Lys His Phe
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 157

Leu Glu Ile Lys Ile Arg His Trp
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
```

```
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Glu
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-His

<400> SEQUENCE: 158

Leu Arg Ile Glu Ile Glu Trp His
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (8)..(8)
<223> OTHER INFORMATION: D-Leu

<400> SEQUENCE: 159

Tyr Arg Val Arg Ile Glu Trp Leu
1               5

<210> SEQ ID NO 160
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Trp

<400> SEQUENCE: 160

Tyr His Val Lys Phe Arg His Trp
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Gln
<220> FEATURE:
<221> NAME/KEY: MISC_FEATURE
<222> LOCATION: (7)..(7)
<223> OTHER INFORMATION: D-His
<220> FEATURE:
```

```
<221> NAME/KEY: MISC_FEATURE
<222> LOCATION: (8)..(8)
<223> OTHER INFORMATION: D-Ile

<400> SEQUENCE: 161

Tyr Arg Val Arg Ile Gln His Ile
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Glu
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Val

<400> SEQUENCE: 162

Tyr Arg Ile Arg Leu Glu His Val
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyr
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
```

```
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-Asn
<220> FEATURE:
<221> NAME/KEY: MISC_FEATURE
<222> LOCATION: (7)..(7)
<223> OTHER INFORMATION: D-His
<220> FEATURE:
<221> NAME/KEY: MISC_FEATURE
<222> LOCATION: (8)..(8)
<223> OTHER INFORMATION: D-Leu

<400> SEQUENCE: 163

Tyr Arg Ile Arg Ile Asn His Leu
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Trp
<220> FEATURE:
<221> NAME/KEY: MISC_FEATURE
<222> LOCATION: (7)..(7)
<223> OTHER INFORMATION: D-Trp

<400> SEQUENCE: 164

Arg Leu Arg Ile His Trp Trp
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
```

```
<223> OTHER INFORMATION: D-Lys
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 165

Arg Leu Lys Val Arg Trp
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
<223> OTHER INFORMATION: D-Trp

<400> SEQUENCE: 166

Arg Leu Arg Val Arg Trp
1               5

<210> SEQ ID NO 167
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Thr
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Leu
```

```
<220> FEATURE:
<221> NAME/KEY: MISC_FEATURE
<222> LOCATION: (5)..(5)
<223> OTHER INFORMATION: D-Val
<220> FEATURE:
<221> NAME/KEY: MISC_FEATURE
<222> LOCATION: (6)..(6)
<223> OTHER INFORMATION: D-Trp

<400> SEQUENCE: 167

Thr Ile Lys Leu Val Trp
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Phe, D-Leu, D-Arg, D-Pro, D-Tyr, D-Trp
      or is absent
<220> FEATURE:
<221> NAME/KEY: MISC_FEATURE
<222> LOCATION: (2)..(2)
<223> OTHER INFORMATION: Xaa is D-Arg, D-His, D-Asp, D-Thr, D-Gln,
      D-Glu, D-Leu, D-Phe, D-Trp or D-Lys
<220> FEATURE:
<221> NAME/KEY: MISC_FEATURE
<222> LOCATION: (3)..(3)
<223> OTHER INFORMATION: Xaa is D-Leu, D-Val, D-Ile, D-Phe, D-Lys or
      D-Arg
<220> FEATURE:
<221> NAME/KEY: MISC_FEATURE
<222> LOCATION: (4)..(4)
<223> OTHER INFORMATION: Xaa is D-Leu, D-Val, D-Glu, D-Gln, D-Asp,
      D-Asn, D-Pro, D-His, D-Trp, D-Ile, D-Arg or D-Lys
<220> FEATURE:
<221> NAME/KEY: MISC_FEATURE
<222> LOCATION: (5)..(5)
<223> OTHER INFORMATION: Xaa is D-Ile, D-Val, D-Gly, D-Phe, D-Arg,
      D-Lys, D-Gln or D-Leu
<220> FEATURE:
<221> NAME/KEY: MISC_FEATURE
<222> LOCATION: (6)..(6)
<223> OTHER INFORMATION: Xaa is D-His, D-Lys, D-Trp, D-Glu, D-Gln,
      D-Asn, D-Leu, D-Val or D-Arg
<220> FEATURE:
<221> NAME/KEY: MISC_FEATURE
<222> LOCATION: (7)..(7)
<223> OTHER INFORMATION: Xaa is D-Lys, D-His, D-Glu, D-Leu, D-Val,
      D-Gly, D-Phe, D-Tyr or D-Trp
<220> FEATURE:
<221> NAME/KEY: MISC_FEATURE
<222> LOCATION: (8)..(8)
<223> OTHER INFORMATION: Xaa is D-Trp, D-Leu, D-Ile, D-Val, D-His,
      D-Phe, D-Tyr or is absent

<400> SEQUENCE: 168

Xaa Xaa Xaa Xaa Xaa Xaa Xaa Xaa
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
```

```
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a polar side chain
      or a non-polar side chain or is absent

<400> SEQUENCE: 169

Trp Lys Xaa Xaa Xaa Xaa Xaa Xaa
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
      or a non-polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
```

```
<221> NAME/KEY: MISC_FEATURE
<222> LOCATION: (8)..(8)
<223> OTHER INFORMATION: Xaa is a D amino acid having a polar side chain
      or a non-polar side chain or is absent

<400> SEQUENCE: 170

Trp Arg Xaa Xaa Xaa Xaa Xaa Xaa
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-His
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a non-polar side
      chain or is absent

<400> SEQUENCE: 171

Trp His Xaa Xaa Xaa Xaa Xaa Xaa
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: Xaa is a D amino acid having a non-polar side
      chain
```

```
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
      or a non-polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a polar side chain
      or a non-polar side chain or is absent

<400> SEQUENCE: 172

Phe Arg Xaa Xaa Xaa Xaa Xaa Xaa
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
      or a non-polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a polar side chain
      or a non-polar side chain or is absent

<400> SEQUENCE: 173
```

```
Phe Lys Xaa Xaa Xaa Xaa Xaa Xaa
1               5

<210> SEQ ID NO 174
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: Xaa is a D amino acid having a polar side chain
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a polar side chain
      or a non-polar side chain

<400> SEQUENCE: 174

Leu Xaa Xaa Xaa Xaa Xaa Xaa Xaa
1               5

<210> SEQ ID NO 175
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a D amino acid having a polar side chain
      or a non-polar side chain
<220> FEATURE:
<221> NAME/KEY: MISC_FEATURE
<222> LOCATION: (2)..(2)
<223> OTHER INFORMATION: Xaa is a D amino acid having a polar side chain
      or a non-polar side chain
<220> FEATURE:
<221> NAME/KEY: MISC_FEATURE
<222> LOCATION: (3)..(3)
<223> OTHER INFORMATION: Xaa is a D amino acid having a polar side chain
      or a non-polar side chain
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
```

```
<220> FEATURE:
<221> NAME/KEY: MISC_FEATURE
<222> LOCATION: (5)..(5)
<223> OTHER INFORMATION: Xaa is a D amino acid having a polar side chain
      or a non-polar side chain
<220> FEATURE:
<221> NAME/KEY: MISC_FEATURE
<222> LOCATION: (6)..(6)
<223> OTHER INFORMATION: D-Trp

<400> SEQUENCE: 175

Xaa Xaa Xaa Xaa Xaa Trp
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: Xaa is a D amino acid having a polar side chain
      or a non-polar side chain
<220> FEATURE:
<221> NAME/KEY: MISC_FEATURE
<222> LOCATION: (3)..(3)
<223> OTHER INFORMATION: Xaa is a D amino acid having a non-polar side
      chain
<220> FEATURE:
<221> NAME/KEY: MISC_FEATURE
<222> LOCATION: (4)..(4)
<223> OTHER INFORMATION: Xaa is a D amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D amino acid having a non-polar side
      chain
<220> FEATURE:
<221> NAME/KEY: MISC_FEATURE
<222> LOCATION: (6)..(6)
<223> OTHER INFORMATION: Xaa is a D amino acid having a polar side chain
<220> FEATURE:
<221> NAME/KEY: MISC_FEATURE
<222> LOCATION: (7)..(7)
<223> OTHER INFORMATION: Xaa is a D amino acid having a polar side chain
      or a non-polar side chain
<220> FEATURE:
<221> NAME/KEY: MISC_FEATURE
<222> LOCATION: (8)..(8)
<223> OTHER INFORMATION: Xaa is a D amino acid having a polar side chain
      or a non-polar side chain

<400> SEQUENCE: 176

Phe Xaa Xaa Xaa Xaa Xaa Xaa Xaa
1               5

<210> SEQ ID NO 177
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: May be absent
<220> FEATURE:
<221> NAME/KEY: MISC_FEATURE
```

```
<222> LOCATION: (7)..(7)
<223> OTHER INFORMATION: May be absent
<220> FEATURE:
<221> NAME/KEY: MISC_FEATURE
<222> LOCATION: (8)..(8)
<223> OTHER INFORMATION: May be absent
<220> FEATURE:
<221> NAME/KEY: MISC_FEATURE
<222> LOCATION: (9)..(9)
<223> OTHER INFORMATION: May be absent
<220> FEATURE:
<221> NAME/KEY: MISC_FEATURE
<222> LOCATION: (10)..(10)
<223> OTHER INFORMATION: May be absent
<220> FEATURE:
<221> NAME/KEY: MISC_FEATURE
<222> LOCATION: (11)..(11)
<223> OTHER INFORMATION: May be absent
<220> FEATURE:
<221> NAME/KEY: MISC_FEATURE
<222> LOCATION: (12)..(12)
<223> OTHER INFORMATION: May be absent
<220> FEATURE:
<221> NAME/KEY: MISC_FEATURE
<222> LOCATION: (13)..(13)
<223> OTHER INFORMATION: May be absent
<220> FEATURE:
<221> NAME/KEY: MISC_FEATURE
<222> LOCATION: (14)..(14)
<223> OTHER INFORMATION: May be absent
<220> FEATURE:
<221> NAME/KEY: MISC_FEATURE
<222> LOCATION: (15)..(15)
<223> OTHER INFORMATION: May be absent
<220> FEATURE:
<221> NAME/KEY: MISC_FEATURE
<222> LOCATION: (16)..(16)
<223> OTHER INFORMATION: May be absent

<400> SEQUENCE: 177

Arg Arg Arg Arg Arg Arg Arg Arg Arg Arg Arg Arg Arg Arg Arg Arg
1               5                   10                  15

<210> SEQ ID NO 178
<211> LENGTH: 2
<212> TYPE: PRT
<213> ORGANISM: Artificial Sequence
<220> FEATURE:
<223> OTHER INFORMATION: Synthetic peptide

<400> SEQUENCE: 178

Gly Gly
1

<210> SEQ ID NO 179
<211> LENGTH: 5
<212> TYPE: PRT
<213> ORGANISM: Artificial Sequence
<220> FEATURE:
<223> OTHER INFORMATION: Synthetic peptide

<400> SEQUENCE: 179

Gly Gly Ser Gly Gly
1               5

<210> SEQ ID NO 180
<211> LENGTH: 11
<212> TYPE: PRT
<213> ORGANISM: Artificial Sequence
<220> FEATURE:
<223> OTHER INFORMATION: Synthetic peptide

<400> SEQUENCE: 180
```

```
Tyr Ala Arg Ala Ala Ala Arg Gln Ala Arg Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Synthetic peptide

<400> SEQUENCE: 181

Tyr Gly Arg Lys Lys Arg Arg
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic peptide

<400> SEQUENCE: 182

Tyr Gly Arg Lys Lys Arg Arg Gln Arg Arg
1               5                   10

<210> SEQ ID NO 183
<211> LENGTH: 5
<212> TYPE: PRT
<213> ORGANISM: Artificial Sequence
<220> FEATURE:
<223> OTHER INFORMATION: Synthetic peptide

<400> SEQUENCE: 183

Arg Arg Gln Arg Arg
1               5

<210> SEQ ID NO 184
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Leu
<220> FEATURE:
<221> NAME/KEY: MISC_FEATURE
<222> LOCATION: (17)..(17)
<223> OTHER INFORMATION: D-Glu
<220> FEATURE:
<221> NAME/KEY: MISC_FEATURE
<222> LOCATION: (18)..(18)
<223> OTHER INFORMATION: D-Leu
<220> FEATURE:
<221> NAME/KEY: MISC_FEATURE
<222> LOCATION: (19)..(19)
<223> OTHER INFORMATION: D-Lys
<220> FEATURE:
<221> NAME/KEY: MISC_FEATURE
<222> LOCATION: (20)..(20)
<223> OTHER INFORMATION: D-Ile
<220> FEATURE:
<221> NAME/KEY: MISC_FEATURE
<222> LOCATION: (21)..(21)
<223> OTHER INFORMATION: D-Lys
<220> FEATURE:
<221> NAME/KEY: MISC_FEATURE
<222> LOCATION: (22)..(22)
<223> OTHER INFORMATION: D-Phe
<220> FEATURE:
```

```
<221> NAME/KEY: MISC_FEATURE
<222> LOCATION: (23)..(23)
<223> OTHER INFORMATION: D-Trp

<400> SEQUENCE: 184

Arg Arg Arg Arg Arg Arg Arg Arg Arg Arg Gly Gly Ser Gly Gly Leu
1               5                   10                  15

Glu Leu Lys Ile Lys Phe Trp
            20

<210> SEQ ID NO 185
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Glu
<220> FEATURE:
<221> NAME/KEY: MISC_FEATURE
<222> LOCATION: (17)..(17)
<223> OTHER INFORMATION: D-Leu
<220> FEATURE:
<221> NAME/KEY: MISC_FEATURE
<222> LOCATION: (18)..(18)
<223> OTHER INFORMATION: D-Lys
<220> FEATURE:
<221> NAME/KEY: MISC_FEATURE
<222> LOCATION: (19)..(19)
<223> OTHER INFORMATION: D-Ile
<220> FEATURE:
<221> NAME/KEY: MISC_FEATURE
<222> LOCATION: (20)..(20)
<223> OTHER INFORMATION: D-Val
<220> FEATURE:
<221> NAME/KEY: MISC_FEATURE
<222> LOCATION: (21)..(21)
<223> OTHER INFORMATION: D-Trp

<400> SEQUENCE: 185

Arg Arg Arg Arg Arg Arg Arg Arg Arg Arg Gly Gly Ser Gly Gly Glu
1               5                   10                  15

Leu Lys Ile Val Trp
            20

<210> SEQ ID NO 186
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Thr
<220> FEATURE:
<221> NAME/KEY: MISC_FEATURE
<222> LOCATION: (17)..(17)
<223> OTHER INFORMATION: D-Leu
<220> FEATURE:
<221> NAME/KEY: MISC_FEATURE
<222> LOCATION: (18)..(18)
<223> OTHER INFORMATION: D-Lys
<220> FEATURE:
<221> NAME/KEY: MISC_FEATURE
<222> LOCATION: (19)..(19)
<223> OTHER INFORMATION: D-Ile
<220> FEATURE:
<221> NAME/KEY: MISC_FEATURE
<222> LOCATION: (20)..(20)
<223> OTHER INFORMATION: D-Val
```

<220> FEATURE:
<221> NAME/KEY: MISC_FEATURE
<222> LOCATION: (21)..(21)
<223> OTHER INFORMATION: D-Trp

<400> SEQUENCE: 186

Arg Arg Arg Arg Arg Arg Arg Arg Arg Gly Gly Ser Gly Gly Thr
1               5                   10                  15

Leu Lys Ile Val Trp
            20

<210> SEQ ID NO 187
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Trp
<220> FEATURE:
<221> NAME/KEY: MISC_FEATURE
<222> LOCATION: (17)..(17)
<223> OTHER INFORMATION: D-Lys
<220> FEATURE:
<221> NAME/KEY: MISC_FEATURE
<222> LOCATION: (18)..(18)
<223> OTHER INFORMATION: D-Val
<220> FEATURE:
<221> NAME/KEY: MISC_FEATURE
<222> LOCATION: (19)..(19)
<223> OTHER INFORMATION: D-Gln
<220> FEATURE:
<221> NAME/KEY: MISC_FEATURE
<222> LOCATION: (20)..(20)
<223> OTHER INFORMATION: D-Val
<220> FEATURE:
<221> NAME/KEY: MISC_FEATURE
<222> LOCATION: (21)..(21)
<223> OTHER INFORMATION: D-Arg
<220> FEATURE:
<221> NAME/KEY: MISC_FEATURE
<222> LOCATION: (22)..(22)
<223> OTHER INFORMATION: D-Leu
<220> FEATURE:
<221> NAME/KEY: MISC_FEATURE
<222> LOCATION: (23)..(23)
<223> OTHER INFORMATION: D-Trp

<400> SEQUENCE: 187

Arg Arg Arg Arg Arg Arg Arg Arg Arg Gly Gly Ser Gly Gly Trp
1               5                   10                  15

Lys Val Gln Val Arg Leu Trp
            20

<210> SEQ ID NO 188
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: D-Trp
<220> FEATURE:
<221> NAME/KEY: MISC_FEATURE
<222> LOCATION: (16)..(16)
<223> OTHER INFORMATION: D-Arg
<220> FEATURE:
<221> NAME/KEY: MISC_FEATURE
<222> LOCATION: (17)..(17)

```
<223> OTHER INFORMATION: D-Leu
<220> FEATURE:
<221> NAME/KEY: MISC_FEATURE
<222> LOCATION: (18)..(18)
<223> OTHER INFORMATION: D-Lys
<220> FEATURE:
<221> NAME/KEY: MISC_FEATURE
<222> LOCATION: (19)..(19)
<223> OTHER INFORMATION: D-Val
<220> FEATURE:
<221> NAME/KEY: MISC_FEATURE
<222> LOCATION: (20)..(20)
<223> OTHER INFORMATION: D-Arg
<220> FEATURE:
<221> NAME/KEY: MISC_FEATURE
<222> LOCATION: (21)..(21)
<223> OTHER INFORMATION: D-Trp
<220> FEATURE:
<221> NAME/KEY: MISC_FEATURE
<222> LOCATION: (22)..(22)
<223> OTHER INFORMATION: D-Trp

<400> SEQUENCE: 188

Arg Arg Arg Arg Arg Arg Arg Arg Arg Gly Gly Ser Gly Gly Trp Arg
1               5                   10                  15

Leu Lys Val Arg Trp Trp
            20

<210> SEQ ID NO 189
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Trp
<220> FEATURE:
<221> NAME/KEY: MISC_FEATURE
<222> LOCATION: (17)..(17)
<223> OTHER INFORMATION: D-Arg
<220> FEATURE:
<221> NAME/KEY: MISC_FEATURE
<222> LOCATION: (18)..(18)
<223> OTHER INFORMATION: D-Leu
<220> FEATURE:
<221> NAME/KEY: MISC_FEATURE
<222> LOCATION: (19)..(19)
<223> OTHER INFORMATION: D-Lys
<220> FEATURE:
<221> NAME/KEY: MISC_FEATURE
<222> LOCATION: (20)..(20)
<223> OTHER INFORMATION: D-Val
<220> FEATURE:
<221> NAME/KEY: MISC_FEATURE
<222> LOCATION: (21)..(21)
<223> OTHER INFORMATION: D-Arg
<220> FEATURE:
<221> NAME/KEY: MISC_FEATURE
<222> LOCATION: (22)..(22)
<223> OTHER INFORMATION: D-Trp
<220> FEATURE:
<221> NAME/KEY: MISC_FEATURE
<222> LOCATION: (23)..(23)
<223> OTHER INFORMATION: D-Trp

<400> SEQUENCE: 189

Arg Arg Arg Arg Arg Arg Arg Arg Arg Gly Gly Ser Gly Gly Trp
1               5                   10                  15

Arg Leu Lys Val Arg Trp Trp
            20
```

```
<210> SEQ ID NO 190
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 190

Arg Leu Lys Ile Arg Ile His Tyr
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 191

Trp Arg Leu Arg Ile Met Trp
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 192

Trp Arg Leu Arg Ile His Met
1               5

<210> SEQ ID NO 193
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 193

Leu Lys Ile Arg Ile His Tyr Leu
1               5

<210> SEQ ID NO 194
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 194

Leu Lys Ile Arg Ile Arg Tyr His
1               5

<210> SEQ ID NO 195
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 195

Trp Trp Arg Val Lys Leu Arg Trp
1               5

<210> SEQ ID NO 196
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 196

Val Arg Trp Trp Lys Leu Arg Trp
1               5

<210> SEQ ID NO 197
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 197

Trp Arg Leu Lys Val Arg Trp Leu
1               5

<210> SEQ ID NO 198
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 198

Trp Leu Lys Ile Arg Ile His Tyr
1               5

<210> SEQ ID NO 199
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 199

Leu Lys Val Arg Trp Trp Trp Arg
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 200

Trp Arg Leu Arg Leu Arg Trp
1               5

<210> SEQ ID NO 201
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 201

Lys Val Arg Trp Trp Leu Arg Trp
1               5

<210> SEQ ID NO 202
<211> LENGTH: 8
```

```
<212> TYPE: PRT
<213> ORGANISM: Artificial Sequence
<220> FEATURE:
<223> OTHER INFORMATION: Synthetic Polypeptide

<400> SEQUENCE: 202

Leu Trp Arg Leu Lys Val Arg Trp
1               5

<210> SEQ ID NO 203

<400> SEQUENCE: 203

000

<210> SEQ ID NO 204
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 204

Val Arg Trp Trp Trp Arg Leu Lys
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 205

Thr Trp Arg Leu Lys Val Arg Trp
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 206

Leu Lys Ile Arg Ile Trp Tyr His
1               5

<210> SEQ ID NO 207
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 207

Lys Trp Arg Leu Lys Val Arg Trp
1               5

<210> SEQ ID NO 208
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 208
```

```
Leu Lys Ile Arg Ile Leu Tyr His
1               5

<210> SEQ ID NO 209
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 209

Gly Trp Arg Leu Lys Val Arg Trp
1               5

<210> SEQ ID NO 210
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 210

Leu Arg Leu Lys Val Arg Trp Leu
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 211

Leu Lys Ile Arg Phe His Tyr
1               5

<210> SEQ ID NO 212
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 212

Leu Lys Ile Trp Ile Lys Tyr His
1               5

<210> SEQ ID NO 213
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 213

His Arg Leu Lys Val Arg Trp His
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 214

Leu Lys Ile Arg Ile Phe Tyr His
```

```
<210> SEQ ID NO 215
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 215

Trp Arg Phe Lys Phe Arg Trp
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 216

Leu Lys Phe Arg Ile His Tyr
1               5

<210> SEQ ID NO 217
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 217

Arg Trp Arg Leu Lys Val Arg Trp
1               5

<210> SEQ ID NO 218
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 218

Trp Arg Leu Lys Val Arg Trp Phe
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 219

Leu Lys Ile Arg Ile Met Tyr
1               5

<210> SEQ ID NO 220
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 220

Trp Arg Arg Lys Val Arg Trp Trp
1               5
```

```
<210> SEQ ID NO 221
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 221

Leu Arg Leu Lys Val Arg Trp Trp
1               5

<210> SEQ ID NO 222
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 222

Trp Arg Leu Lys Val Arg Trp His
1               5

<210> SEQ ID NO 223
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 223

Leu Lys Ile Leu Ile His Tyr His
1               5

<210> SEQ ID NO 224
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 224

Arg Leu Lys Val Arg Trp Trp Trp
1               5

<210> SEQ ID NO 225
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 225

Arg Arg Leu Lys Val Arg Trp Trp
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 226

Trp Arg Phe Lys Val Arg Trp
1               5
```

<210> SEQ ID NO 227
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 227

Arg Lys Ile Arg Ile His Tyr His
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 228

Leu Lys Ile Arg Asx His Tyr
1               5

<210> SEQ ID NO 229
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 229

Glu Trp Arg Leu Lys Val Arg Trp
1               5

<210> SEQ ID NO 230
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 230

Trp Arg Leu Lys Val Arg Trp Arg
1               5

<210> SEQ ID NO 231
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 231

Phe Arg Leu Lys Val Arg Trp Trp
1               5

<210> SEQ ID NO 232
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 232

Phe Lys Ile Arg Ile His Tyr Phe
1               5

```
<210> SEQ ID NO 233
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 233

Leu Lys Ile Lys Ile His Tyr
1               5

<210> SEQ ID NO 234
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 234

Trp Trp Arg Leu Lys Val Arg Trp
1               5

<210> SEQ ID NO 235
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 235

Thr Leu Lys Ile Arg Ile His Tyr
1               5

<210> SEQ ID NO 236
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 236

Gly Leu Lys Ile Arg Ile His Tyr
1               5

<210> SEQ ID NO 237
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 237

Leu Lys Ile Trp Ile Tyr Tyr His
1               5

<210> SEQ ID NO 238
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 238

Trp Arg Leu Arg Val Arg Trp Trp
1               5

<210> SEQ ID NO 239
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 239

Leu Arg Ile Arg Ile His Tyr His
1               5

<210> SEQ ID NO 240
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 240

Leu Lys Ile Arg Ile His Leu His
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 241

Trp Arg Leu Lys Glu Arg Trp Trp
1               5

<210> SEQ ID NO 242
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 242

Met Arg Leu Arg Ile His Trp
1               5

<210> SEQ ID NO 243
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 243

Lys Leu Lys Ile Arg Ile His Tyr
1               5

<210> SEQ ID NO 244
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 244

Leu Lys Ile Arg Ile Glx Tyr
1               5

<210> SEQ ID NO 245
<211> LENGTH: 7
```

```
<212> TYPE: PRT
<213> ORGANISM: Artificial Sequence
<220> FEATURE:
<223> OTHER INFORMATION: Synthetic Polypeptide

<400> SEQUENCE: 245

Leu Lys Ile Arg Ile His Tyr
1               5

<210> SEQ ID NO 246
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 246

Trp Arg Met Arg Ile His Trp
1               5

<210> SEQ ID NO 247
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 247

Phe Leu Lys Ile Arg Ile His Tyr
1               5

<210> SEQ ID NO 248
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 248

Trp Arg Leu Lys Val Ala Trp
1               5

<210> SEQ ID NO 249
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 249

Asx Lys Ile Arg Ile His Tyr
1               5

<210> SEQ ID NO 250
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 250

Leu Lys Ile Arg Ile His Tyr Phe
1               5

<210> SEQ ID NO 251

<400> SEQUENCE: 251
```

000

<210> SEQ ID NO 252
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 252

Leu Lys Asx Arg Ile His Tyr
1               5

<210> SEQ ID NO 253
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 253

Glu Leu Lys Ile Arg Ile His Tyr
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 254

Met Arg Leu Lys Val Arg Trp
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 255

Trp Arg Leu Lys Thr Arg Trp
1               5

<210> SEQ ID NO 256
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 256

Tyr Leu Lys Ile Arg Ile His Tyr
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 257

Trp Ala Leu Lys Val Arg Trp 1               5

<210> SEQ ID NO 258

<400> SEQUENCE: 258

000

<210> SEQ ID NO 259
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 259

His Leu Lys Ile Arg Ile His Tyr
1               5

<210> SEQ ID NO 260
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 260

Trp Arg Leu Arg Met His Trp
1               5

<210> SEQ ID NO 261
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 261

Phe Trp Arg Leu Lys Val Arg Trp
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 262

Trp Arg Leu Arg Ile His Thr
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 263

Trp Arg Leu Lys Phe Arg Trp
1               5

<210> SEQ ID NO 264
<211> LENGTH: 8
<212> TYPE: PRT
<213> ORGANISM: Artificial Sequence

```
<220> FEATURE:
<223> OTHER INFORMATION: Synthetic Polypeptide

<400> SEQUENCE: 264

Trp Glu Leu Lys Val Arg Trp Trp
1               5

<210> SEQ ID NO 265
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 265

His Arg Leu Lys Val Arg Trp Trp
1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 266

His Trp Arg Leu Lys Val Arg Trp
1               5

<210> SEQ ID NO 267

<400> SEQUENCE: 267

000

<210> SEQ ID NO 268
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 268

Tyr Trp Arg Leu Lys Val Arg Trp
1               5

<210> SEQ ID NO 269
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 269

Leu Lys Ile Arg Ile His Tyr Ala
1               5

<210> SEQ ID NO 270
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 270

Phe Arg Leu Arg Ile His Trp
1               5
```

<210> SEQ ID NO 271
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 271

Leu Lys Ile Arg Ile Ala Tyr
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 272

Trp Arg Leu Arg Ile Ala Trp
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 273

Trp Gln Leu Lys Val Arg Trp
1               5

<210> SEQ ID NO 274
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 274

Leu Lys Ile Arg Ile His Arg His
1               5

<210> SEQ ID NO 275
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 275

Trp Arg Leu Lys Val Arg Trp Glu
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 276

Trp Arg Thr Lys Val Arg Trp
1               5

<210> SEQ ID NO 277
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 277

Leu Lys Ile Arg Ile Tyr Tyr
1               5

<210> SEQ ID NO 278
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 278

Trp Arg Leu Lys Val Arg Arg Trp
1               5

<210> SEQ ID NO 279

<400> SEQUENCE: 279

000

<210> SEQ ID NO 280
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 280

Trp Arg Leu Gln Val Arg Trp
1               5

<210> SEQ ID NO 281
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 281

Trp Arg Leu Lys Val Gln Trp
1               5

<210> SEQ ID NO 282

<400> SEQUENCE: 282

000

<210> SEQ ID NO 283
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 283

Thr Lys Ile Arg Ile His Tyr
1               5

```
<210> SEQ ID NO 284
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 284

Trp Arg Leu Lys Val Arg Glu Trp
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 285

Leu Lys Ile Gln Ile His Tyr
1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 286

Trp Arg Asx Lys Val Arg Trp
1               5

<210> SEQ ID NO 287

<400> SEQUENCE: 287

000

<210> SEQ ID NO 288
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 288

Trp Arg Leu Glu Val Arg Trp Trp
1               5

<210> SEQ ID NO 289
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 289

Trp Arg Leu Lys Val Arg Trp
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic Polypeptide
```

<400> SEQUENCE: 290

Arg Arg Leu Arg Ile His Trp
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 291

Leu Lys Ile Arg Ile His Tyr Arg
1               5

<210> SEQ ID NO 292
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 292

Trp Arg Leu His Val Arg Trp Trp
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 293

Asx Arg Leu Lys Val Arg Trp
1               5

<210> SEQ ID NO 294
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 294

Trp Asn Leu Lys Val Arg Trp
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 295

Leu Lys Ile His Ile His Tyr His
1               5

<210> SEQ ID NO 296
<211> LENGTH: 7
<212> TYPE: PRT
<213> ORGANISM: Artificial Sequence
<220> FEATURE:
<223> OTHER INFORMATION: Synthetic Polypeptide

```
<400> SEQUENCE: 296

Trp Arg Leu Lys Val Asn Trp
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 297

Leu Lys Ile Arg Ile Xaa Tyr
1               5

<210> SEQ ID NO 298
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 298

Arg Leu Lys Val Arg Trp Trp
1               5

<210> SEQ ID NO 299
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 299

Leu Lys Ile Trp Ile His Tyr His
1               5

<210> SEQ ID NO 300
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 300

His Tyr His Ile Arg Ile Lys Leu
1               5

<210> SEQ ID NO 301
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 301

Trp Arg Leu Ala Val Arg Trp
1               5

<210> SEQ ID NO 302
<211> LENGTH: 8
<212> TYPE: PRT
<213> ORGANISM: Artificial Sequence
```

```
<220> FEATURE:
<223> OTHER INFORMATION: Synthetic Polypeptide

<400> SEQUENCE: 302

Leu Lys Ile Phe Ile Tyr Tyr His
1               5

<210> SEQ ID NO 303
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 303

Leu Lys Ile Arg Ile Ala Tyr His
1               5

<210> SEQ ID NO 304
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 304

Trp Met Leu Arg Ile His Trp
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 305

Trp Thr Leu Arg Ile His Trp
1               5

<210> SEQ ID NO 306
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 306

Trp Arg Leu Asn Val Arg Trp
1               5

<210> SEQ ID NO 307
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 307

Trp Arg Leu Lys Asx Arg Trp
1               5

<210> SEQ ID NO 308

<400> SEQUENCE: 308

000
```

<210> SEQ ID NO 309
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 309

Leu Ala Ile Arg Ile His Tyr His
1               5

<210> SEQ ID NO 310
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 310

Trp Arg Leu Trp Val Arg Trp Trp
1               5

<210> SEQ ID NO 311
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 311

Arg Ile Arg Trp Tyr Trp Lys
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 312

Ala Arg Leu Arg Ile His Trp
1               5

<210> SEQ ID NO 313
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 313

Trp Arg Leu Lys Val Glu Trp Trp
1               5

<210> SEQ ID NO 314
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 314

Trp Arg Leu Arg Ile Thr Trp
1               5

<210> SEQ ID NO 315
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 315

Trp Arg Leu Glu Val Arg Trp
1               5

<210> SEQ ID NO 316
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 316

Leu Glu Ile Arg Ile His Tyr
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 317

Leu Lys Ile Met Ile His Tyr
1               5

<210> SEQ ID NO 318
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 318

Leu Lys Ile Arg Ile His Glu His
1               5

<210> SEQ ID NO 319
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 319

Trp Gln Leu Lys Val Gln Trp
1               5

<210> SEQ ID NO 320
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 320

Leu Lys Ile Glx Ile His Tyr
1               5

<210> SEQ ID NO 321

<400> SEQUENCE: 321

000

<210> SEQ ID NO 322
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 322

Trp Glu Leu Arg Ile His Trp
1               5

<210> SEQ ID NO 323
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 323

Trp Arg Leu Lys Val Arg Ala
1               5

<210> SEQ ID NO 324
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 324

Leu Lys Ile Arg Ile Glu Tyr
1               5

<210> SEQ ID NO 325
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 325

Trp Arg Leu Ala Ile His Trp
1               5

<210> SEQ ID NO 326
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 326

His Trp Arg Trp Arg Trp Arg
1               5

<210> SEQ ID NO 327
<211> LENGTH: 7
<212> TYPE: PRT
<213> ORGANISM: Artificial Sequence
<220> FEATURE:
<223> OTHER INFORMATION: Synthetic Polypeptide

```
<400> SEQUENCE: 327

Thr Arg Leu Arg Ile His Trp
1               5

<210> SEQ ID NO 328
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 328

Trp Arg Leu Lys Val Asp Trp
1               5

<210> SEQ ID NO 329
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 329

Phe Lys Ile Arg Ile His Tyr His
1               5

<210> SEQ ID NO 330
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 330

Trp Arg Leu Thr Ile His Trp
1               5

<210> SEQ ID NO 331
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 331

Trp Asp Leu Lys Val Arg Trp
1               5

<210> SEQ ID NO 332
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 332

Trp Arg Leu Arg Ile Phe Trp
1               5

<210> SEQ ID NO 333
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

```
<222> LOCATION: (4)..(4)
<223> OTHER INFORMATION: Xaa can be any naturally occurring amino acid

<400> SEQUENCE: 333

Leu Lys Ile Xaa Ile His Tyr
1               5

<210> SEQ ID NO 334
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 334

Leu Lys Ile Arg Ile His Ala
1               5

<210> SEQ ID NO 335
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 335

Leu Lys Ile Tyr Ile His Tyr
1               5

<210> SEQ ID NO 336
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 336

Leu Lys Ile Ala Ile His Tyr
1               5

<210> SEQ ID NO 337
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 337

Trp Arg Ile Arg Ile Arg Trp
1               5

<210> SEQ ID NO 338
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 338

Glu Arg Leu Lys Val Arg Trp
1               5

<210> SEQ ID NO 339
<211> LENGTH: 7
<212> TYPE: PRT
<213> ORGANISM: Artificial Sequence
<220> FEATURE:
```

<223> OTHER INFORMATION: Synthetic Polypeptide

<400> SEQUENCE: 339

Trp Arg Leu Asp Val Arg Trp
1               5

<210> SEQ ID NO 340
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 340

Leu Lys Ile Trp Ile Trp Tyr His
1               5

<210> SEQ ID NO 341
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 341

Leu Lys Ile Arg Arg His Tyr His
1               5

<210> SEQ ID NO 342
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 342

Ala Arg Leu Lys Val Arg Trp
1               5

<210> SEQ ID NO 343
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 343

Trp Arg Ala Lys Val Arg Trp
1               5

<210> SEQ ID NO 344
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 344

Trp Arg Leu Lys Ala Arg Trp
1               5

<210> SEQ ID NO 345
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 345

Trp Ala Leu Arg Ile His Trp
1               5

<210> SEQ ID NO 346
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 346

Trp Arg Leu Arg Ala His Trp
1               5

<210> SEQ ID NO 347
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 347

Trp Arg Leu Arg Ile His Ala
1               5

<210> SEQ ID NO 348
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 348

Trp Arg Leu Glu Ile His Trp
1               5

<210> SEQ ID NO 349
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 349

Trp Arg Leu Arg Ile Glu Trp
1               5

<210> SEQ ID NO 350
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 350

Trp Arg Leu Met Ile His Trp
1               5

<210> SEQ ID NO 351
<211> LENGTH: 7
<212> TYPE: PRT
<213> ORGANISM: Artificial Sequence
<220> FEATURE:
<223> OTHER INFORMATION: Synthetic Polypeptide

```
<400> SEQUENCE: 351

Trp Arg Thr Arg Ile His Trp
1               5

<210> SEQ ID NO 352
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 352

Trp Arg Leu Asn Val Asn Trp
1               5

<210> SEQ ID NO 353
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 353

Leu Lys Ile Arg Ile His Tyr Glu
1               5

<210> SEQ ID NO 354
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 354

Leu Lys Ile Glu Ile His Tyr
1               5

<210> SEQ ID NO 355
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 355

Trp Arg Ala Arg Ile His Trp
1               5

<210> SEQ ID NO 356
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 356

Trp Arg Leu Arg Thr His Trp
1               5

<210> SEQ ID NO 357
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 357
```

```
Trp Asn Leu Asn Val Arg Trp
1               5

<210> SEQ ID NO 358
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 358

Leu Lys Ile Phe Ile Trp Tyr His
1               5

<210> SEQ ID NO 359
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 359

Glu Arg Leu Lys Val Arg Trp Trp
1               5

<210> SEQ ID NO 360
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 360

Ala Lys Ile Arg Ile His Tyr His
1               5

<210> SEQ ID NO 361
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 361

Lys Trp Arg Trp Tyr Arg Arg
1               5

<210> SEQ ID NO 362
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 362

Arg Ile His Tyr His Ile Lys Leu
1               5

<210> SEQ ID NO 363
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 363
```

```
Leu Lys Ile Glu Ile His Tyr His
1               5

<210> SEQ ID NO 364
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 364

Lys Val Arg Trp Trp Trp Arg Leu
1               5

<210> SEQ ID NO 365
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 365

His Lys Ile Arg Ile His Tyr His
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 366

Leu Ala Ile Arg Ile His Tyr
1               5

<210> SEQ ID NO 367
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 367

Leu Glu Ile Arg Ile His Tyr His
1               5

<210> SEQ ID NO 368
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 368

Lys Leu Lys Trp Leu Trp
1               5

<210> SEQ ID NO 369
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 369

Leu Lys Ile Phe Ile His Tyr His
```

```
1               5

<210> SEQ ID NO 370
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 370

Lys Ile Arg Ile His Tyr His Leu
1               5

<210> SEQ ID NO 371
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 371

Tyr Arg Leu Lys Val Arg Trp
1               5

<210> SEQ ID NO 372
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 372

Trp Asn Leu Lys Val Asn Trp
1               5

<210> SEQ ID NO 373
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 373

Lys Ile Arg Ile His Tyr His
1               5

<210> SEQ ID NO 374
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 374

Leu Lys Ile Arg Ile His
1               5

<210> SEQ ID NO 375
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 375

Ile His Tyr His Arg Ile Lys Leu
1               5
```

```
<210> SEQ ID NO 376
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 376

Trp Arg His Lys Val Arg Trp
1               5

<210> SEQ ID NO 377
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 377

Glu Lys Ile Arg Ile His Tyr
1               5

<210> SEQ ID NO 378
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 378

Trp Arg Leu Lys His Arg Trp
1               5

<210> SEQ ID NO 379
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 379

Leu Lys Ile Arg Ile His Ala His
1               5

<210> SEQ ID NO 380
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 380

Trp Arg Leu Leu Val Arg Trp Trp
1               5

<210> SEQ ID NO 381
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 381

Leu Lys Val Arg Trp Trp
1               5
```

```
<210> SEQ ID NO 382
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 382

Trp Gln Leu Gln Val Arg Trp
1               5

<210> SEQ ID NO 383
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 383

Arg Ile His Tyr His Leu Lys Ile
1               5

<210> SEQ ID NO 384
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 384

Trp Arg Leu Lys Val Glu Trp
1               5

<210> SEQ ID NO 385

<400> SEQUENCE: 385

000

<210> SEQ ID NO 386
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 386

Ile Arg Ile His Tyr His Leu Lys
1               5

<210> SEQ ID NO 387
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 387

Glu Lys Ile Arg Ile His Tyr His
1               5

<210> SEQ ID NO 388
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 388

Trp Glu Leu Lys Val Arg Trp
1               5

<210> SEQ ID NO 389
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 389

Leu Lys Ile Arg Ile Glu Tyr His
1               5

<210> SEQ ID NO 390
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 390

Ala Trp Ala Lys Val Arg Trp
1               5

<210> SEQ ID NO 391
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 391

Trp Phe Leu Arg Ile His Trp
1               5

<210> SEQ ID NO 392
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 392

Trp Arg Thr Lys Thr Arg Trp
1               5

<210> SEQ ID NO 393
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 393

Trp Arg Asx Lys Asx Arg Trp
1               5

<210> SEQ ID NO 394
<211> LENGTH: 8
<212> TYPE: PRT
<213> ORGANISM: Artificial Sequence
<220> FEATURE:
<223> OTHER INFORMATION: Synthetic Polypeptide
```

```
<400> SEQUENCE: 394

Ile His Tyr His Leu Lys Ile Arg
1               5

<210> SEQ ID NO 395
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 395

Glu Arg Leu Arg Ile His Trp
1               5

<210> SEQ ID NO 396
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 396

Trp Arg Leu Arg Ile His Glu
1               5

<210> SEQ ID NO 397
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 397

Trp Glu Leu Lys Val Glu Trp
1               5

<210> SEQ ID NO 398
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 398

Leu Lys Ala Arg Ile His Tyr His
1               5

<210> SEQ ID NO 399
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 399

Ala Arg Leu Lys Ala Arg Trp
1               5

<210> SEQ ID NO 400
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 400
```

```
Leu Lys Thr Arg Ile His Tyr
1               5

<210> SEQ ID NO 401
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 401

Ala Arg Ala Arg Ile His Trp
1               5

<210> SEQ ID NO 402
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 402

Trp Arg Ala Lys Ala Arg Trp
1               5

<210> SEQ ID NO 403
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 403

Trp Asp Leu Asp Val Arg Trp
1               5

<210> SEQ ID NO 404
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 404

Trp Arg Leu Lys Val
1               5

<210> SEQ ID NO 405
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 405

Leu Lys Arg Arg Ile His Tyr His
1               5

<210> SEQ ID NO 406
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 406
```

```
Trp Arg Leu Lys Val Arg
1               5

<210> SEQ ID NO 407
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 407

Trp Arg His Lys His Arg Trp
1               5

<210> SEQ ID NO 408
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 408

Trp Arg Glu Lys Val Arg Trp Trp
1               5

<210> SEQ ID NO 409
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 409

Leu Lys Ile Ala Ile His Tyr His
1               5

<210> SEQ ID NO 410
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 410

Leu His Leu Lys Ile Arg Tyr His
1               5

<210> SEQ ID NO 411
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 411

Phe Lys Leu Glu Ile Arg Tyr His
1               5

<210> SEQ ID NO 412
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 412

Phe Glu Ile Arg Leu Trp His His
```

```
1               5

<210> SEQ ID NO 413
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 413

Phe Lys Leu Lys Leu Arg Trp
1               5

<210> SEQ ID NO 414
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 414

Leu Lys Ile Arg Ile Arg Phe His
1               5

<210> SEQ ID NO 415
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 415

Leu Lys Leu Arg Ile Arg His His
1               5

<210> SEQ ID NO 416
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 416

Trp Leu Arg Val Gln Val Lys Leu Trp
1               5

<210> SEQ ID NO 417
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 417

Phe Arg Leu Trp Ile His Trp
1               5

<210> SEQ ID NO 418
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 418

Phe Lys Ile Glu Ile Glu Tyr His
1               5
```

```
<210> SEQ ID NO 419
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 419

Val Lys Val Trp Gly Arg Leu Trp
1               5

<210> SEQ ID NO 420
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 420

Leu Arg Ile Arg Leu His Tyr His
1               5

<210> SEQ ID NO 421
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 421

Leu Arg Ile Lys Ile Arg Phe His
1               5

<210> SEQ ID NO 422
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 422

Leu Asp Leu Arg Phe Lys Leu Tyr
1               5

<210> SEQ ID NO 423
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 423

Phe Arg Leu Arg Ile Trp Trp
1               5

<210> SEQ ID NO 424
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 424

Trp His Val Lys Phe Glu Leu Phe
1               5
```

<210> SEQ ID NO 425
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 425

Trp Trp Leu Arg Ile His Trp
1               5

<210> SEQ ID NO 426
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 426

Phe Arg Leu Lys Leu Arg Phe His
1               5

<210> SEQ ID NO 427
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 427

Phe His Leu Glu Ile Arg His Trp
1               5

<210> SEQ ID NO 428
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 428

Trp Arg Leu Trp Ile His Trp
1               5

<210> SEQ ID NO 429
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 429

Leu Lys Leu Glu Ile Arg Trp His
1               5

<210> SEQ ID NO 430
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 430

Phe Glu Ile Arg Leu His His Trp
1               5

```
<210> SEQ ID NO 431
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 431

Phe His Ile Glu Ile Arg His Phe
1               5

<210> SEQ ID NO 432
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 432

Arg Leu Lys Trp Arg Trp
1               5

<210> SEQ ID NO 433
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 433

Trp Trp Leu Lys Leu Arg Trp
1               5

<210> SEQ ID NO 434
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 434

Leu Lys Leu His Leu His Phe His
1               5

<210> SEQ ID NO 435
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 435

Trp Glu Val Gln Val Glu Trp
1               5

<210> SEQ ID NO 436
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 436

Arg Leu Lys Val Trp Trp
1               5

<210> SEQ ID NO 437
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 437

Phe His Ile His Ile Lys Phe His
1               5

<210> SEQ ID NO 438
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 438

Lys Leu Lys Leu Arg Trp Phe
1               5

<210> SEQ ID NO 439
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 439

Arg Arg Leu Lys Val Arg Trp Arg
1               5

<210> SEQ ID NO 440
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 440

Tyr His Leu Lys Leu His Tyr Trp
1               5

<210> SEQ ID NO 441
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 441

Leu Arg Val Gln Val Arg Leu
1               5

<210> SEQ ID NO 442
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 442

Phe Glu Ile Arg Ile His Tyr His
1               5

<210> SEQ ID NO 443
<211> LENGTH: 8
```

```
<212> TYPE: PRT
<213> ORGANISM: Artificial Sequence
<220> FEATURE:
<223> OTHER INFORMATION: Synthetic Polypeptide

<400> SEQUENCE: 443

Phe His Leu His Leu Lys His Trp
1               5

<210> SEQ ID NO 444
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 444

Arg Trp Lys Val Arg Trp
1               5

<210> SEQ ID NO 445
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 445

His Arg Phe Lys Val Gln Leu Tyr
1               5

<210> SEQ ID NO 446
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 446

Arg Leu Arg Ile His Trp Phe
1               5

<210> SEQ ID NO 447
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 447

Leu Glu Phe Glu Leu Lys Tyr Trp
1               5

<210> SEQ ID NO 448
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 448

Lys Leu Lys Leu Arg Trp Trp
1               5

<210> SEQ ID NO 449
<211> LENGTH: 8
<212> TYPE: PRT
```

```
<213> ORGANISM: Artificial Sequence
<220> FEATURE:
<223> OTHER INFORMATION: Synthetic Polypeptide

<400> SEQUENCE: 449

Trp Lys Val Gln Val Arg Tyr Trp
1               5

<210> SEQ ID NO 450
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 450

Arg Leu Arg Leu Lys Trp
1               5

<210> SEQ ID NO 451
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 451

Arg Leu Lys Ile Arg Ile His Tyr
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 452

Trp Arg Leu Arg Ile Met Trp
1               5

<210> SEQ ID NO 453
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 453

Trp Arg Leu Arg Ile His Met
1               5

<210> SEQ ID NO 454
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 454

Arg Arg Arg Arg Arg Arg Arg Arg Gly Gly Ser Gly Gly Arg Leu
1               5                   10                  15

Lys Val Arg Trp
            20

<210> SEQ ID NO 455
```

```
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 455

Arg Arg Arg Arg Arg Arg Arg Arg Arg Gly Gly Ser Gly Gly Arg Leu
1               5                   10                  15

Lys Val Arg Trp
            20

<210> SEQ ID NO 456
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 456

Tyr Gly Arg Lys Lys Arg Arg Gln Arg Arg Gly Gly Ser Gly Gly
1               5                   10                  15

Arg Leu Lys Val Arg Trp
            20

<210> SEQ ID NO 457
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 457

Tyr Gly Arg Lys Lys Arg Arg Gln Arg Arg Gly Gly Ser Gly Gly
1               5                   10                  15

Arg Leu Lys Val Arg Trp
            20

<210> SEQ ID NO 458
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 458

Arg Arg Arg Arg Arg Arg Arg Arg Arg Gly Gly Ser Gly Gly Leu
1               5                   10                  15

Glu Leu Lys Ile Lys Phe Trp
            20

<210> SEQ ID NO 459
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (1)..(1)
<223> OTHER INFORMATION: Tam

<400> SEQUENCE: 459

Arg Arg Arg Arg Arg Arg Arg Arg Arg Gly Gly Ser Gly Gly Glu
1               5                   10                  15

Leu Lys Ile Val Trp
            20

<210> SEQ ID NO 460
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 460

Arg Arg Arg Arg Arg Arg Arg Arg Arg Gly Gly Ser Gly Gly Thr
1               5                   10                  15

Leu Lys Ile Val Trp
            20

<210> SEQ ID NO 461
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 461

Arg Arg Arg Arg Arg Arg Arg Arg Arg Gly Gly Ser Gly Gly Trp
1               5                   10                  15

Lys Val Gln Val Arg Leu Trp
            20

<210> SEQ ID NO 462
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 462

Arg Arg Arg Arg Arg Arg Arg Arg Gly Gly Ser Gly Gly Trp Arg
1               5                   10                  15

Leu Lys Val Arg Trp Trp
            20

<210> SEQ ID NO 463
<211> LENGTH: 23
<212> TYPE: PRT
<213> ORGANISM: Artificial Sequence
<220> FEATURE:
<223> OTHER INFORMATION: Synthetic Polypeptide
```

```
<400> SEQUENCE: 463

Arg Arg Arg Arg Arg Arg Arg Arg Arg Gly Gly Ser Gly Gly Trp
1               5                   10                  15

Arg Leu Lys Val Arg Trp Trp
            20

<210> SEQ ID NO 464
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 464

Tyr Gly Arg Lys Lys Arg Arg Gln Arg Arg Gly Gly Ser Gly Gly
1               5                   10                  15

Trp Arg Leu Lys Val Arg Trp Trp
            20

<210> SEQ ID NO 465
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 465

Arg Arg Arg Arg Arg Arg Arg Arg Gly Gly Ser Gly Gly Trp Arg
1               5                   10                  15

Leu Lys Val Arg Trp Trp
            20

<210> SEQ ID NO 466
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 466

Arg Arg Arg Arg Arg Arg Arg Arg Arg Gly Gly Ser Gly Gly Trp
1               5                   10                  15

Lys Val Gln Val Arg Leu Trp
            20

<210> SEQ ID NO 467
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Tam

<400> SEQUENCE: 467

Arg Arg Arg Arg Arg Arg Arg Arg Pro Ile Lys Phe Arg Phe Tyr
1               5                   10                  15

His Arg
```

-continued

<210> SEQ ID NO 468
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 468

Arg Arg Arg Arg Arg Arg Arg Arg Arg Gly Gly Ser Gly Gly Glu
1               5                   10                  15

Leu Lys Ile Val Trp
            20

<210> SEQ ID NO 469
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 469

Tyr Gly Arg Lys Lys Arg Arg Gln Arg Arg Gly Gly Ser Gly Gly
1               5                   10                  15

Trp Arg Leu Lys Val Arg Trp Trp
            20

<210> SEQ ID NO 470
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 470

Arg Arg Arg Arg Arg Arg Arg Arg Arg Pro Ile Lys Phe Arg Phe Tyr
1               5                   10                  15

His Arg

<210> SEQ ID NO 471
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 471

Arg Arg Arg Arg Arg Arg Arg Arg Arg Gly Gly Ser Gly Gly Trp Arg
1               5                   10                  15

Ile Trp Ile Arg Tyr Trp
            20

<210> SEQ ID NO 472
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 472

Arg Arg Arg Arg Arg Arg Arg Arg Arg Gly Gly Ser Gly Gly Thr
1               5                   10                  15

Leu Lys Ile Val Trp
            20

```
<210> SEQ ID NO 473
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent, D-Lys, D-Thr, D-Gly, D-Glu,
      D-His, D-Met, D-Ala, D-Ile, D-Phe, D-Arg, D-Leu, D-Tyr, D-Pro or
      D-Trp
<220> FEATURE:
<221> NAME/KEY: MISC_FEATURE
<222> LOCATION: (2)..(2)
<223> OTHER INFORMATION: Xaa is absent, D-Met, D-Arg, D-His, D-Thr,
      D-Gln, D-Glu, D-Ala, D-Ile, D-Asp, D-Leu, D-Phe, D-Pro, D-Trp, or
      D-Lys
<220> FEATURE:
<221> NAME/KEY: MISC_FEATURE
<222> LOCATION: (3)..(3)
<223> OTHER INFORMATION: Xaa is absent, D-Nle, D-Cha, D-Thr, D-Ala,
      D-His, D-Met, D-Leu, D-Val, D-Ile, D-Phe, D-Lys, D-Arg or D-Trp
<220> FEATURE:
<221> NAME/KEY: MISC_FEATURE
<222> LOCATION: (4)..(4)
<223> OTHER INFORMATION: Xaa is D-Thr, D-Ala, D-Met, D-Tyr, D-Met(O),
      D-Cit, D-Nle, D-Cha, D-Tyr, D-Phe, D-Leu, D-Glu, D-Gln, D-Gly,
      D-Val, D-Asp, D-Asn, D-Pro, D-His, D-Trp, D-Ile, D-Arg, or D-Lys
<220> FEATURE:
<221> NAME/KEY: MISC_FEATURE
<222> LOCATION: (5)..(5)
<223> OTHER INFORMATION: Xaa is D-Nle, D-Cha, D-Met, D-Thr, D-His,
      D-Ile, D-Val, D-Ala, D-Gly, D-Phe, D-Gln, D-Glu, D-Arg, D-Lys,
      D-Leu or D-Trp
<220> FEATURE:
<221> NAME/KEY: MISC_FEATURE
<222> LOCATION: (6)..(6)
<223> OTHER INFORMATION: Xaa is absent, D-Asp, D-Cha, D-Met, D-Thr,
      D-Phe, D-Nle, D-Tyr, D-Ile, D-His, D-Lys, D-Trp, D-Gln, D-Asn,
      D-Glu, D-Leu, D-Ala, D-Val or D-Arg
<220> FEATURE:
<221> NAME/KEY: MISC_FEATURE
<222> LOCATION: (7)..(7)
<223> OTHER INFORMATION: Xaa is absent, D-Ala, D-Arg, D-His, D-Leu,
      D-Lys, D-Glu, D-Met, D-Val, D-Gly, D-Tyr, D-Phe, D-Thr or D-Trp
<220> FEATURE:
<221> NAME/KEY: MISC_FEATURE
<222> LOCATION: (8)..(8)
<223> OTHER INFORMATION: Xaa is absent, D-Ala, D-Lys, D-Arg, D-Trp,
      D-Leu, D-Ile, D-Val, D-His, D-Phe, or D-Tyr

<400> SEQUENCE: 473

Xaa Xaa Xaa Xaa Xaa Xaa Xaa Xaa
1               5

<210> SEQ ID NO 474
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
```

```
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: Xaa is a D-amino acid having a polar side chain
      or a non-polar side chain
<220> FEATURE:
<221> NAME/KEY: MISC_FEATURE
<222> LOCATION: (6)..(6)
<223> OTHER INFORMATION: Xaa  is a D-amino acid having a polar side
      chain or a non-polar side chain
<220> FEATURE:
<221> NAME/KEY: MISC_FEATURE
<222> LOCATION: (7)..(7)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (8)..(8)
<223> OTHER INFORMATION: Xaa is absent or is a D-amino acid having a
      non-polar side chain

<400> SEQUENCE: 474

Trp Arg Leu Arg Xaa Xaa Xaa Xaa
1               5

<210> SEQ ID NO 475
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: D-Trp
<220> FEATURE:
<221> NAME/KEY: MISC_FEATURE
<222> LOCATION: (2)..(2)
<223> OTHER INFORMATION: D-Arg
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: Xaa is a D-amino acid having a polar side chain
      or a non-polar side chain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: ; Xaa72 is absent or is a D-amino acid having a
      polar side chain or a non-polar side chain
<220> FEATURE:
<221> NAME/KEY: MISC_FEATURE
<222> LOCATION: (7)..(7)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (8)..(8)
<223> OTHER INFORMATION: Xaa is absent or is a D-amino acid having a
      non-polar side chain

<400> SEQUENCE: 475

Trp Arg Leu Xaa Xaa Xaa Xaa Xaa
1               5

<210> SEQ ID NO 476
```

```
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: Xaa is a D-amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is a D-amino acid having a polar side chain
      or a non-polar side chain
<220> FEATURE:
<221> NAME/KEY: MISC_FEATURE
<222> LOCATION: (6)..(6)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (7)..(7)
<223> OTHER INFORMATION: Xaa is D-amino acid having a polar side chain
<220> FEATURE:
<221> NAME/KEY: MISC_FEATURE
<222> LOCATION: (8)..(8)
<223> OTHER INFORMATION: Xaa is absent or is a D-amino acid having a
      non-polar side chain

<400> SEQUENCE: 476

Leu Lys Ile Xaa Xaa Xaa Xaa Xaa
1               5

<210> SEQ ID NO 477
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (2)..(2)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (5)..(5)
<223> OTHER INFORMATION: D-Arg
<220> FEATURE:
<221> NAME/KEY: MISC_FEATURE
<222> LOCATION: (6)..(6)
```

```
<223> OTHER INFORMATION: D-Ile
<220> FEATURE:
<221> NAME/KEY: MISC_FEATURE
<222> LOCATION: (7)..(7)
<223> OTHER INFORMATION: Xaa is absent or is a D-amino acid having a
      polar side chain or a non-polar side chain
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (9)..(9)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (10)..(10)
<223> OTHER INFORMATION: Xaa is absent or is a D-amino acid having a
      non-polar side chain

<400> SEQUENCE: 477

Xaa Xaa Lys Ile Arg Ile Xaa Xaa Xaa Xaa
1               5                   10

<210> SEQ ID NO 478
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (2)..(2)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (3)..(3)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (4)..(4)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (7)..(7)
<223> OTHER INFORMATION: D-Arg
<220> FEATURE:
<221> NAME/KEY: MISC_FEATURE
<222> LOCATION: (8)..(8)
<223> OTHER INFORMATION: D-Trp
<220> FEATURE:
<221> NAME/KEY: MISC_FEATURE
<222> LOCATION: (9)..(9)
<223> OTHER INFORMATION: Xaa is absent or is a D-amino acid having a
      non-polar side chain
```

<400> SEQUENCE: 478

Xaa Xaa Xaa Xaa Lys Val Arg Trp Xaa
1               5

<210> SEQ ID NO 479
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (2)..(2)
<223> OTHER INFORMATION: Xaa is absent or a D-amino acid having a polar
      side chain or a non-polar side chain
<220> FEATURE:
<221> NAME/KEY: MISC_FEATURE
<222> LOCATION: (3)..(3)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (4)..(4)
<223> OTHER INFORMATION: Xaa is a D-amino acid having a polar side chain
      or a non-polar side chain
<220> FEATURE:
<221> NAME/KEY: MISC_FEATURE
<222> LOCATION: (5)..(5)
<223> OTHER INFORMATION: Xaa is absent or is a D-amino acid having a
      polar side chain or a non-polar side chain
<220> FEATURE:
<221> NAME/KEY: MISC_FEATURE
<222> LOCATION: (6)..(8)
<223> OTHER INFORMATION: D-Trp
<220> FEATURE:
<221> NAME/KEY: MISC_FEATURE
<222> LOCATION: (9)..(9)
<223> OTHER INFORMATION: Xaa is absent or is a D-amino acid having a
      polar side chain
<220> FEATURE:
<221> NAME/KEY: MISC_FEATURE
<222> LOCATION: (10)..(10)
<223> OTHER INFORMATION: Xaa is absent or is a D-amino acid having a
      non-polar side chain
<220> FEATURE:
<221> NAME/KEY: MISC_FEATURE
<222> LOCATION: (11)..(11)
<223> OTHER INFORMATION: Xaa is absent or is a D-amino acid having a
      polar side chain

<400> SEQUENCE: 479

Xaa Xaa Xaa Xaa Xaa Trp Trp Trp Xaa Xaa Xaa
1               5                   10

<210> SEQ ID NO 480
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is a D-amino acid having a polar side chain
      or a non-polar side chain
<220> FEATURE:
<221> NAME/KEY: MISC_FEATURE
<222> LOCATION: (2)..(2)
<223> OTHER INFORMATION: Xaa is a D-amino acid having a polar side chain

```
        or a non-polar side chain
<220> FEATURE:
<221> NAME/KEY: MISC_FEATURE
<222> LOCATION: (3)..(3)
<223> OTHER INFORMATION: Xaa is a D-amino acid having a polar side chain
        or a non-polar side chain
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Trp

<400> SEQUENCE: 480

Xaa Xaa Xaa Arg Ile His Trp
1               5

<210> SEQ ID NO 481
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent or a D-amino acid having a
        non-polar side chain
<220> FEATURE:
<221> NAME/KEY: MISC_FEATURE
<222> LOCATION: (2)..(2)
<223> OTHER INFORMATION: Xaa is absent or a D-amino acid having a polar
        side chain or a non-polar side chain
<220> FEATURE:
<221> NAME/KEY: MISC_FEATURE
<222> LOCATION: (3)..(3)
<223> OTHER INFORMATION: Xaa is absent or is a D-amino acid having a
        polar side chain or a non-polar side chain
<220> FEATURE:
<221> NAME/KEY: MISC_FEATURE
<222> LOCATION: (4)..(4)
<223> OTHER INFORMATION: D-Arg
<220> FEATURE:
<221> NAME/KEY: MISC_FEATURE
<222> LOCATION: (5)..(5)
<223> OTHER INFORMATION: D-Ile
<220> FEATURE:
<221> NAME/KEY: MISC_FEATURE
<222> LOCATION: (6)..(6)
<223> OTHER INFORMATION: D-His
<220> FEATURE:
<221> NAME/KEY: MISC_FEATURE
<222> LOCATION: (7)..(7)
<223> OTHER INFORMATION: D-Tyr
<220> FEATURE:
<221> NAME/KEY: MISC_FEATURE
<222> LOCATION: (8)..(8)
<223> OTHER INFORMATION: Xaa is absent, a D-amino acid having a polar
        side chain, -D-His-D-Leu-D-Lys, -D-His-D-Leu-D-Lys-D-Ile, or
        -D-His-D-Ile-D-Lys-D-Leu

<400> SEQUENCE: 481

Xaa Xaa Xaa Arg Ile His Tyr Xaa
1               5
```